United States Patent
Hermann et al.

(10) Patent No.: US 7,220,561 B2
(45) Date of Patent: May 22, 2007

(54) PROCESSES FOR ENHANCED PRODUCTION OF PANTOTHENATE

(75) Inventors: Theron Hermann, Kinnelon, NJ (US); Thomas A. Patterson, North Attleboro, MA (US); Janice G. Pero, Lexington, MA (US); R. Roger Yocum, Lexington, MA (US); Kai-Uwe Baldenius, Ludwigshafen (DE); Christine Beck, Mannheim (DE)

(73) Assignee: BASF Aktiengesellschaft (DE)

( * ) Notice: Subject to any disclaimer, the term of this patent is extended or adjusted under 35 U.S.C. 154(b) by 155 days.

(21) Appl. No.: 10/466,717

(22) PCT Filed: Jan. 19, 2002

(86) PCT No.: PCT/US02/01842

§ 371 (c)(1),
(2), (4) Date: Jul. 18, 2003

(87) PCT Pub. No.: WO02/057474

PCT Pub. Date: Jul. 25, 2002

(65) Prior Publication Data

US 2004/0086982 A1    May 6, 2004

Related U.S. Application Data

(60) Provisional application No. 60/262,995, filed on Jan. 19, 2001.

(51) Int. Cl.
*C12P 13/04* (2006.01)
*C12P 13/00* (2006.01)
*C12N 1/21* (2006.01)

(52) U.S. Cl. .................. 435/128; 435/252.3; 435/116; 435/106; 435/320.1; 536/23.2

(58) Field of Classification Search .................. 435/41, 435/252, 243
See application file for complete search history.

(56) References Cited

U.S. PATENT DOCUMENTS

| | | | | |
|---|---|---|---|---|
| 5,518,906 | A | * | 5/1996 | Hikichi et al. .............. 435/116 |
| 6,171,845 | B1 | * | 1/2001 | Elischweski et al. .. 435/252.33 |
| 6,184,006 | B1 | * | 2/2001 | Rieping et al. ............. 435/128 |
| 6,689,592 | B2 | * | 2/2004 | Rieping et al. ............. 435/146 |

FOREIGN PATENT DOCUMENTS

| | | |
|---|---|---|
| EP | 1006189 A2 | 6/2000 |
| WO | WO 01/21722 A2 | 3/2001 |
| WO | WO 02/061108 A2 | 8/2002 |

OTHER PUBLICATIONS

Sigma Catalog Catalog No. p2250, P3161 and p2375.*
Baigori et al. J. Bactr. 1991, 4240-4242.*
Vallari et al. J. Bactr. 1988, 3961-3966.*
Elischweski et al J. Biotech, 1999, 75, pp. 135-146.*
Primerano D.A. et al., "Role of Acetohydroxy Acid Isomoreroreductase in Biosynthesis of Pantothenic Acid in *Salmonella typhimurium*", Journal of Bacteriology, Washington, DC, US, vol. 153, No. 1, 1983, pp. 259-269, ISSN: 0021-9193.
Kunst F. et al., "The Complete Genome Sequence of the Gram-Positive Bacterium *Bacillus subtilis*" Nature, Macmillan Journals Ltd., London, GB, vol. 390, Nov. 20, 1997, pp. 249-266, ISSN: 0028-0836.

* cited by examiner

*Primary Examiner*—Rebecca E. Prouty
*Assistant Examiner*—Md. Younus Meah
(74) *Attorney, Agent, or Firm*—Lahive & Cockfield, LLP

(57) ABSTRACT

The present invention features improved methods for producing pantoate and pantothenate utilizing microorganisms having modified pantothenate biosynthetic enzyme activities. In particular, the invention features methods for reducing byproduct formation and increasing yields and purity of desired product. Recombinant microorganisms and conditions for culturing same are also are featured. Also featured are compositions produced by such microorganisms.

13 Claims, 10 Drawing Sheets

Figure 2. Proposed pathway for biosynthesis of HMBPA.

[R]-3-(2-hydroxy-3-methyl-butyrylamino)-propionic acid ("HMBPA")

HPLC - analysis of Fermentation broth

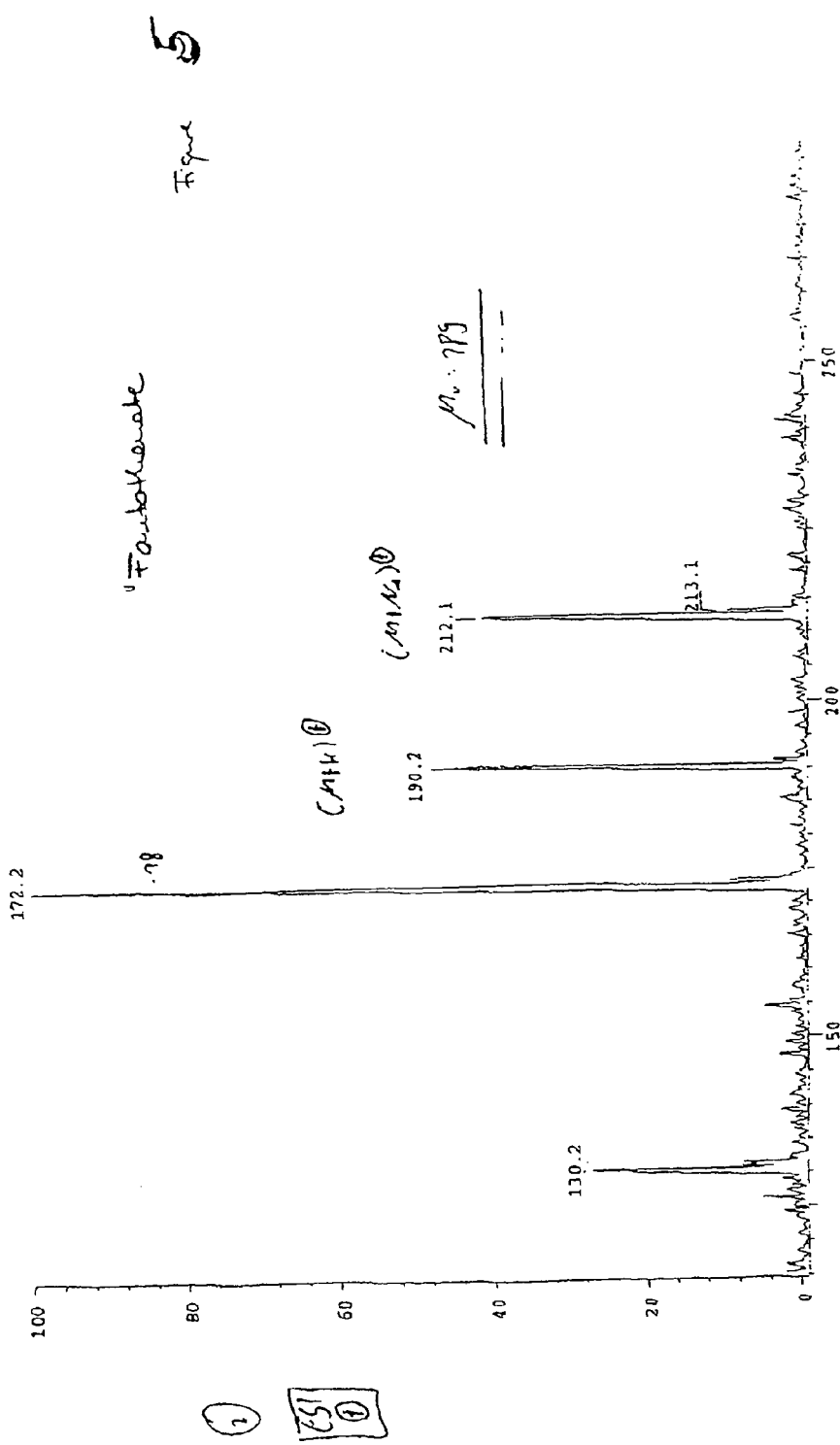

Figure 6. An alignment of the C-terminal amino acids from all known or suspected PanB proteins.

```
                      1        2      3
                      ⇓        ⇓      ⇓
CAA10222.1      AYVA EV KGVT FP GA- EHGF SA
APE0676         RYAE DV RNGR FP GE- EHWH --AKEPLEDIS
RYP04152        LYIE EV DGGI YP AE- EHFQ
REC04341        QYMA EV ESGV YP GE- EHSF H
sp|Q09672       RYIY EV EQGL YP AE- EHSF Q
RNG01188        AYVA EV KAKT FP AA- EHIF AD
RNM00107        AYVA EV KAKT FP AA- EHIF AD
RPA02174        AYVR AV KDVS FP AA- EHGF NA
RCA00999        SYAK EV REGT FP DE- AHSF K- IDQSIIDEITK
REF01843        KYIE EV KDGV FP GP- EHGF K- ISDDVLEKLY
RCJ02253        KVRD EV KSGI FP SQ- EHSF DYIDDELLDKLY
RBS02239        GYVQ DV RHRA FP EQ- KHSF Q- MNQTVLDGLYGGK
RDR03436        HYAA EV RARE FP SK- DNSF V- MKDEVLDKLY
RCY14036        KFSG EV RQRQ FP RR- G
RPA08114        RFAE DV RERR FP EA- RHCF AMRE
RRC02991        AYAA EV RSPA FP AP- EFSF DEVKK
SCC75A.02       AYAE DV WGGI FP AD- EHSV H
CAA65397.1      AYIA DI HAGI FP GE- AESF
CAB56202.1      EWVA AE KLN-
RMT01063        QYAQ EV AGGV FP AD- EHSF
sp|Q10505       QYAQ EV AGGV FP AD- EHSF
RML00370        QYAE EV ASAV FP AE- EHCF
RML00622        QYAE EV ASAV FP AE- EHCF
RAA01082        NFKI DV EGGN FP SE- EESY G
RHP00462        QYAD DV KKGN FP NE- LESY H
RPG00121        HYIA DV KSND FP NK- DEDY
RPH00184        TFRE EV KEGK FP GR- EHW EFQDKEEFKRIKDNVMKKLNL
RPF00767        EFRK EV KEGK FP GK- EHW EYQDKEIFNRIEDNVMRKLRL
TM1728          EFRR EV KKG  FP TE- EHSF TDKSKGGVSS
PABCS70         EFKK DV KGGK FP GR- EHW EFQDKEEFKRIKESVLRKVD
PSCC3568        EYIA SV EDKT FP ERG THIF KVKEDLWNEFLSSINEK
AAD37248.1      QYRE EV KSRA YP AE- QHIY PIPKEFLVEFQKAVDELPEK
T3F17.24        EKCE EJ SKAV FP GP- SHSP YKITASELDGFLIELQKLGFDKAASAAALAAENMEPSK
```

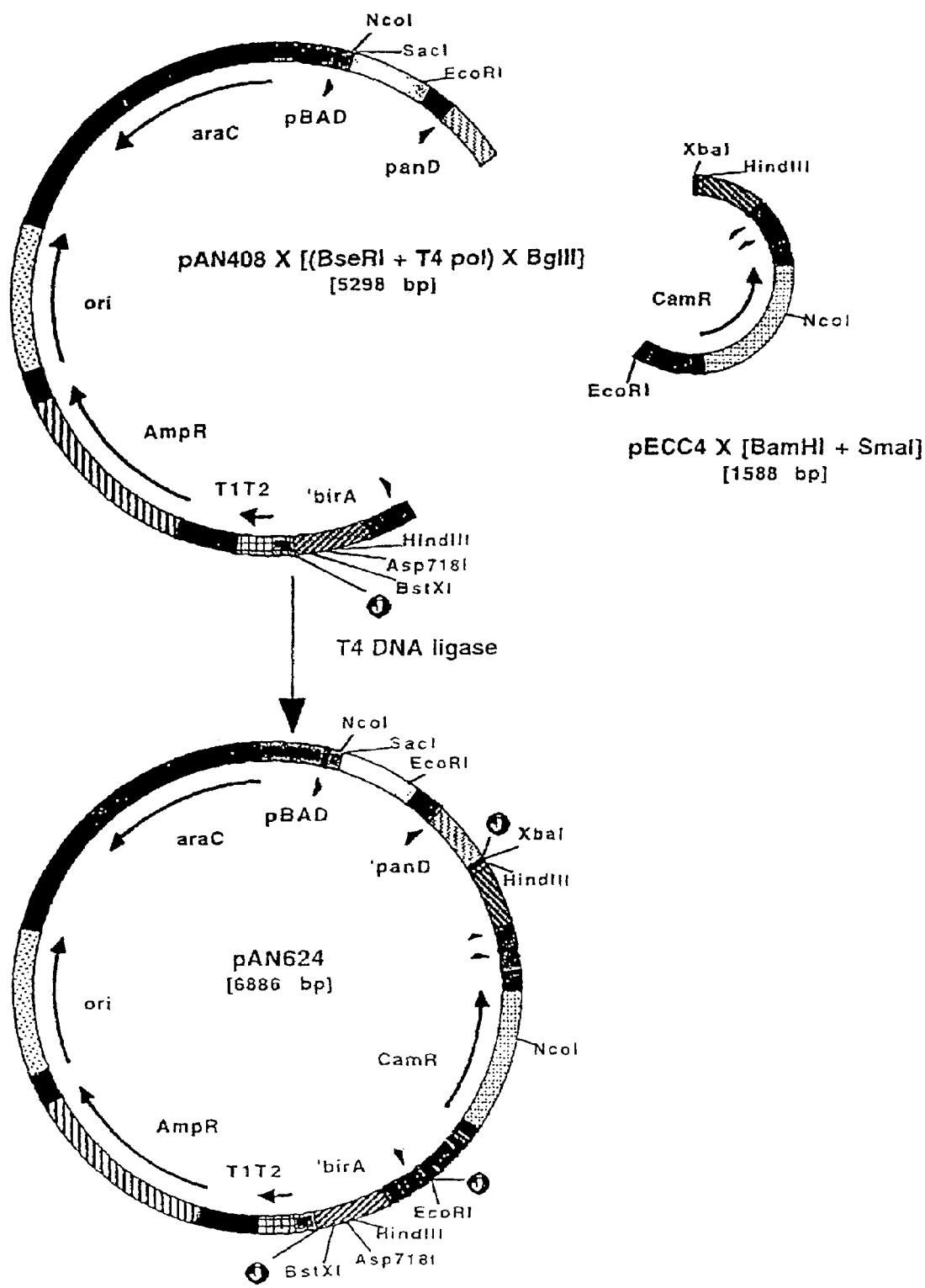
Figure 7. Construction of pAN624.

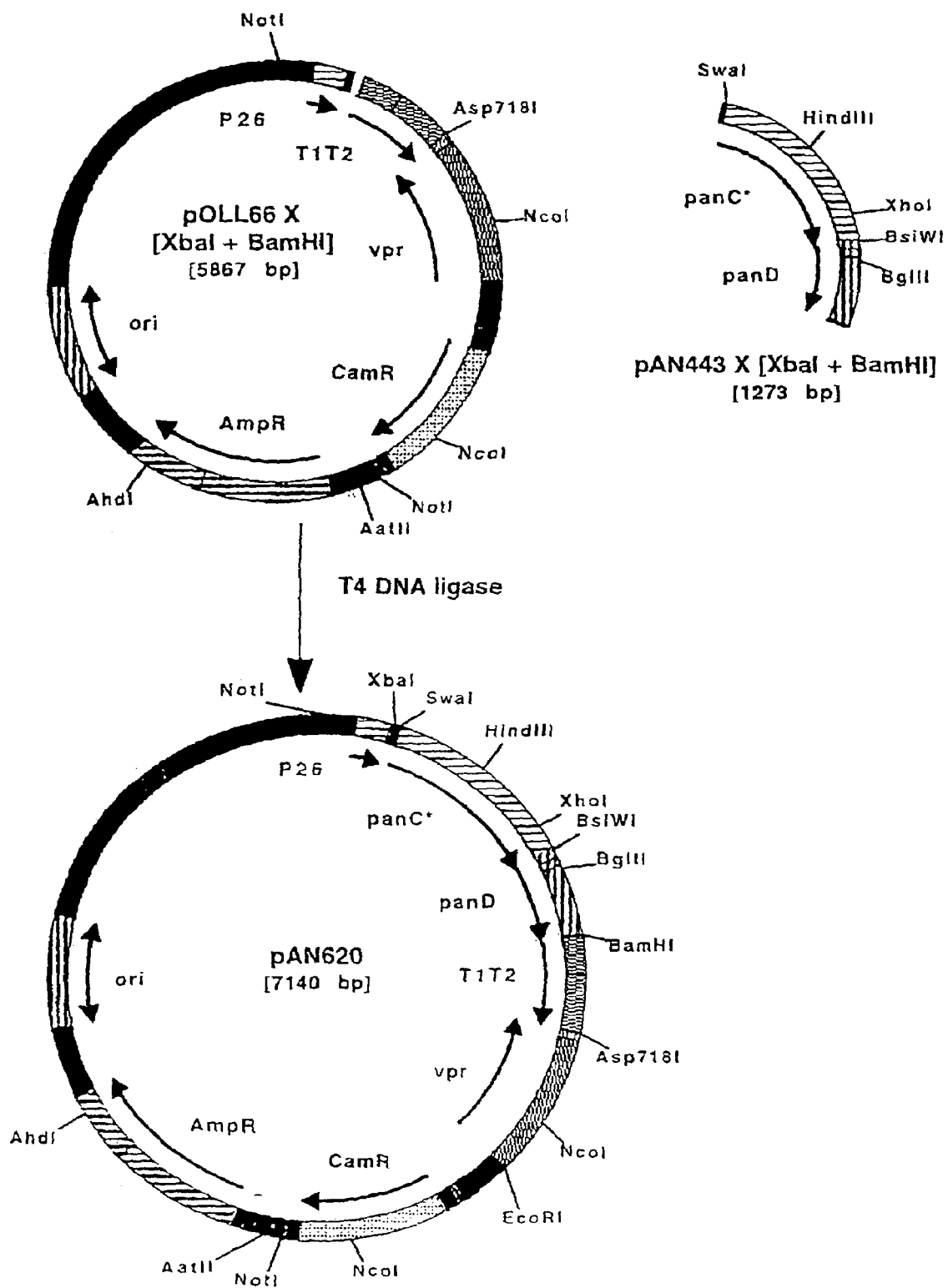
Figure 8. Construction of pAN620.

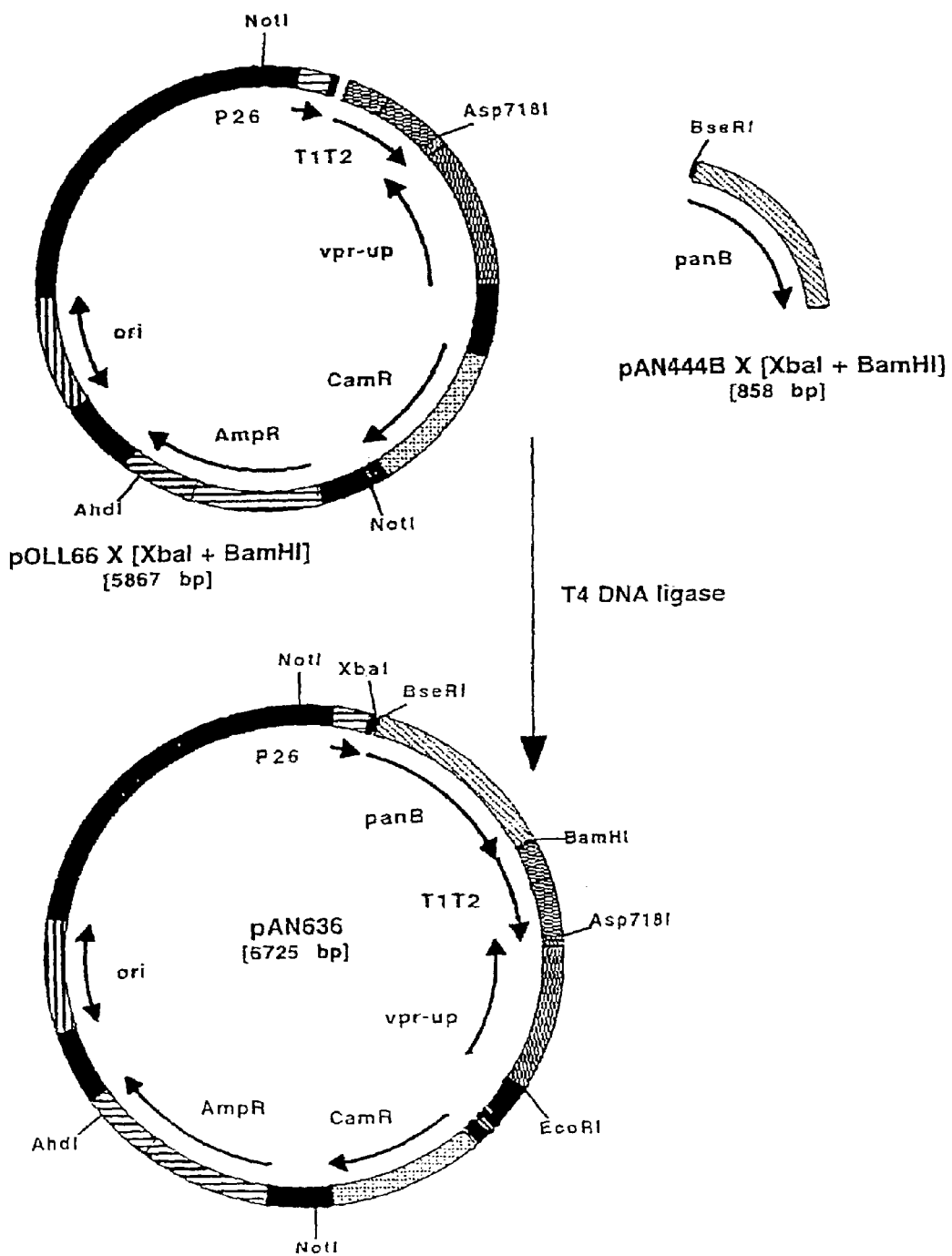

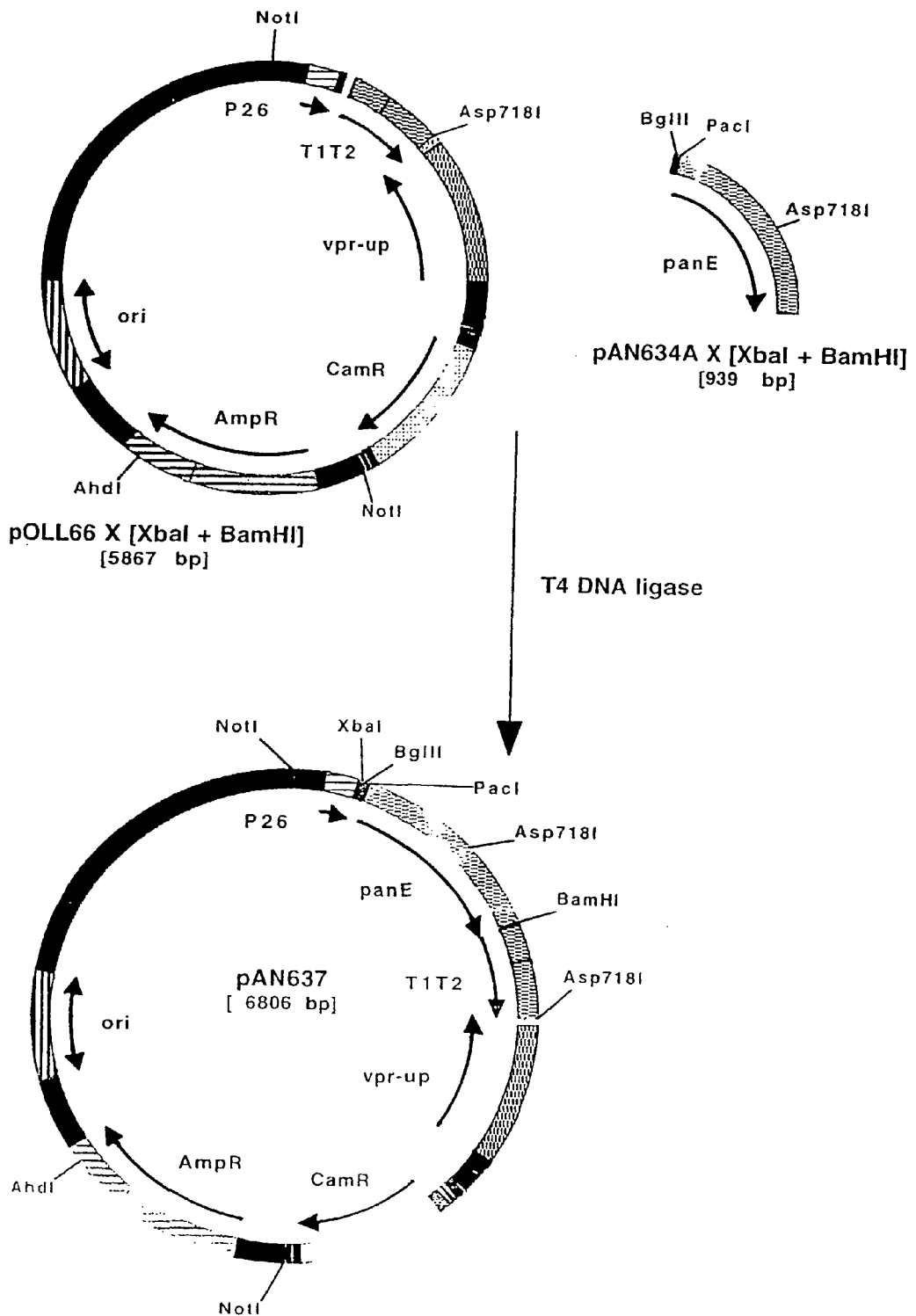
Figure 10. Construction of pAN637.

SEQUENCE LISTING

<160> NUMBER OF SEQ ID NOS: 27

<210> SEQ ID NO 1
<211> LENGTH: 194
<212> TYPE: DNA
<213> ORGANISM: Artificial Sequence
<220> FEATURE:
<223> OTHER INFORMATION: Description of Artificial Sequence:promoter sequence

```
<220> FEATURE:
<221> NAME/KEY: -35_signal
<222> LOCATION: (136)..(141)
<220> FEATURE:
<221> NAME/KEY: -10_signal
<222> LOCATION: (159)..(164)

<400> SEQUENCE: 1
gctattgacg acagctatgg ttcactgtcc accaaccaaa actgtgctca gtaccgccaa      60
tatttctccc ttgaggggta caaagaggtg tccctagaag agatccacgc tgtgtaaaaa     120
ttttacaaaa aggtattgac tttccctaca gggtgtgtaa taatttaatt acaggcgggg     180
gcaaccccgc ctgt                                                      194

<210> SEQ ID NO 2
<211> LENGTH: 163
<212> TYPE: DNA
<213> ORGANISM: Artificial Sequence
<220> FEATURE:
<223> OTHER INFORMATION: Description of Artificial Sequence:promoter
      sequence
<220> FEATURE:
<221> NAME/KEY: -35_signal
<222> LOCATION: (113)..(118)
<220> FEATURE:
<221> NAME/KEY: -10_signal
<222> LOCATION: (136)..(141)

<400> SEQUENCE: 2
gcctacctag cttccaagaa agatatccta acagcacaag agcggaaaga tgttttgttc      60
tacatccaga acaacctctg ctaaaattcc tgaaaaattt tgcaaaaagt tgttgacttt     120
atctacaagg tgtggtataa taatcttaac aacagcagga cgc                      163

<210> SEQ ID NO 3
<211> LENGTH: 127
<212> TYPE: DNA
<213> ORGANISM: Artificial Sequence
<220> FEATURE:
<223> OTHER INFORMATION: Description of Artificial Sequence:promoter
      sequence
<220> FEATURE:
<221> NAME/KEY: -35_signal
<222> LOCATION: (34)..(39)
<220> FEATURE:
<221> NAME/KEY: -10_signal
<222> LOCATION: (58)..(63)
<220> FEATURE:
<221> NAME/KEY: -35_signal
<222> LOCATION: (75)..(80)
<220> FEATURE:
<221> NAME/KEY: -10_signal
<222> LOCATION: (98)..(103)

<400> SEQUENCE: 3
gaggaatcat agaattttgt caaataatt ttattgacaa cgtcttatta acgttgatat       60
aatttaaatt ttatttgaca aaaatgggct cgtgttgtac aataaatgta gtgaggtgga     120
tgcaatg                                                              127

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 4
```

```
taaacatgag gaggagaaaa catg                                          24

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 5
attcgagaaa tggagagaat ataatatg                                      28

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 6
agaaaggagg tga                                                      13

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:ribosome
      binding site
<220> FEATURE:
<223> OTHER INFORMATION: All occurrences of n = any nucleotide

<400> SEQUENCE: 7
ttaagaaagg aggtgannnn atg                                           23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:ribosome
      binding site
<220> FEATURE:
<223> OTHER INFORMATION: All occurrences of n = any nucleotide

<400> SEQUENCE: 8
ttagaaagga ggtgannnnn atg                                           23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:ribosome
      binding site
<220> FEATURE:
<223> OTHER INFORMATION: All occurrences of n = any nucleotide

<400> SEQUENCE: 9
agaaaggagg tgannnnnnn atg                                           23

<210> SEQ ID NO 10
<211> LENGTH: 22
<212> TYPE: DNA
<213> ORGANISM: Artificial Sequence
```

```
<220> FEATURE:
<223> OTHER INFORMATION: Description of Artificial Sequence:ribosome
      binding site
<220> FEATURE:
<223> OTHER INFORMATION: All occurrences of n = any nucleotide

<400> SEQUENCE: 10
agaaaggagg tgannnnnna tg                                               22

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 11
ccctctagaa ggaggagaaa acatg                                            25

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 12
ccctctagag gaggagaaaa catg                                             24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 13
ttagaaagga ggatttaaat atg                                              23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 14
ttagaaagga ggtttaatta atg                                              23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 15
ttagaaagga ggtgatttaa atg                                              23

<210> SEQ ID NO 16
<211> LENGTH: 23
<212> TYPE: DNA
```

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:ribosome binding site

<400> SEQUENCE: 16
ttagaaagga ggtgtttaaa atg          23

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence:ribosome binding site

<400> SEQUENCE: 17
attcgagaaa ggaggtgaat ataatatg          28

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence:ribosome binding site

<400> SEQUENCE: 18
attcgagaaa ggaggtgaat aataatg          27

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence:ribosome binding site

<400> SEQUENCE: 19
attcgtagaa aggaggtgaa ttaatatg          28

<210> SEQ ID NO 20
<211> LENGTH: 6886
<212> TYPE: DNA
<213> ORGANISM: Artificial Sequence
<220> FEATURE:
<223> OTHER INFORMATION: Description of Artificial Sequence: vector
<220> FEATURE:
<223> OTHER INFORMATION: pAN624

<400> SEQUENCE: 20
aagaaaccaa ttgtccatat tgcatcagac attgccgtca ctgcgtcttt tactggctct          60
tctcgctaac caaaccggta accccgctta ttaaaagcat tctgtaacaa agcgggacca          120
aagccatgac aaaaacgcgt aacaaaagtg tctataatca cggcagaaaa gtccacattg          180
attatttgca cggcgtcaca ctttgctatg ccatagcatt tttatccata agattagcgg          240
atcctacctg acgcttttta tcgcaactct ctactgtttc tccatacccg tttttttggg          300
ctaacaggag gaattaacca tggatccgag ctcgacagta tcaagcactt cacaatctgg          360
gagctgaaag cccgccttat gtagctcata cttgacaaat ccaaggtcaa atggatatt          420 gtgggcgaca aaataagcgc cgtcaagcaa ttggaatact cttcagcaa ctgcttcaaa          480 tggctgttca ttctcgacca tttgattaga gattccagta agctgctcaa taaaagcagg          540
gattgattta tttggattaa tgtatttttga aaaccgctca gtaatttgtc cattttcgat          600

```
tacaaccgct gcgatttgta tgattttatc gcctttcttc ggcgaattcc ctgttgtctc    660
tacatctata acaacgaacc gttgcttatt cattaaaatg dacacctcaa ttcttgcata    720
cgacaaaagt gtaacacgtt ttgtacggaa atggagcggc aaaaccgttt tactctcaaa    780
atcttaaaag aaaaccccg ataaagggg cttttcttct acaaaattgt acgggctggt    840
tcgttcccca gcatttgttc aattttgttt tgatcattca gaacagccac tttcggctca    900
tggcttgccg cttcttgatc agacatcatt ttgtaggaaa aataatgac cttatctcct    960 tcctgcacaa ggcgtgcggc tgcaccgttt aagcatatga cgccgcttcc ccgtttacca   1020
ggaataatat acgtttcaag acgtgctcca ttattattat tcacaatttg tacttttca   1080 ttaggaagca ttcccacagc atcaatgaga tcctctagag tcgacctgca ggcatgcaag   1140
cttccgtcga cgctctccct tatgcgactc ctgcattagg aagcagccca gtagtaggtt   1200
gaggccgttg agcaccgccg ccgcaaggaa tggtgcatgc aaggagatgg cgcccaacag   1260
tcccccggcc acgggcctg ccaccatacc cacgccgaaa caagcgctca tgagcccgaa   1320
gtggcgagcc cgatcttccc catcggtgat gtcggcgata taggcgccag caaccgcacc   1380
tgtggcgccg gtgatgccgg ccacgatgcg tccggcgtag aggatcaatc ttcatccatt   1440
ccaaggtaaa tccccttcg ccgtttctgt taccattata cacctttga accttaacgt   1500 aaacgttaag ttttaaaaaa caataaaaaa gacgagcagc atacagcacc cgtctttcac   1560
tttcctgttt aagctaaact tccccgccact gacagagact cttttgaag ctttcagaa   1620 agcactcgat acgcgatctg gagctgtaat ataaaacct tcttcaacta acggggcagg   1680
ttagtgacat tagaaaaccg actgtaaaaa gtacagtcgg cattatctca tattataaaa   1740
gccagtcatt aggcctatct gacaattcct gaatagagtt cataaacaat cctgcatgat   1800
aaccatcaca aacagaatga tgtacctgta aagatagcgg taaatatatt gaattacctt   1860
tattaatgaa ttttcctgct gtaataatgg gtagaagta attactatta ttattgatat   1920
ttaagttaaa cccagtaaat gaagtccatg gaataataga aagagaaaaa gcattttcag   1980
gtataggtgt tttgggaaac aatttccccg aaccattata tttctctaca tcagaaaggt   2040
ataaatcata aaactctttg aagtcattct ttacaggagt ccaaatacca gagaatgttt   2100
tagatacacc atcaaaaatt gtataaagtg gctctaactt atcccaataa cctaactctc   2160
cgtcgctatt gtaaccagtt ctaaaagctg tatttgagtt tatcacccctt gtcactaaga   2220 aaataaatgc agggtaaaat ttatatcctt cttgttttat gtttcggtat aaaacactaa   2280
tatcaatttc tgtggttata ctaaaagtcg tttgttggtt caaataatga ttaaatatct   2340
cttttctctt ccaattgtct aaatcaattt tattaaagtt catttgatat gcctcctaaa   2400
tttttatcta aagtgaattt aggaggctta cttgtctgct ttcttcatta gaatcaatcc   2460 tttttaaaa gtcaatatta ctgtaacata aatatatatt ttaaaatat cccactttat   2520 ccaattttcg tttgttgaac taatgggtgc tttagttgaa gaataaagac cacattaaaa   2580
aatgtggtct tttgtgttt tttaaaggat ttgagcgtag cgaaaaatcc ttttctttct   2640
tatcttgata ataagggtaa ctattgcatg ataagctgtc aaacatgaga attcccgttt   2700
tcttctgcaa gccaaaaaac cttccgttac aacgagaagg attcttcact ttctaaagtt   2760
cggcgagttt catccctctg tcccagtcct tttttggatc aaggcagact gctgcaatgt   2820
ctatctattt taataatagg tgcagttcgc aggcgatact gcccaatgga agtataccaa   2880
aatcaacggg cttgtaccaa cacattagcc caattcgata tcggcagaat agattttttt   2940
```

```
aatgccttcg ttcgtttcta aaagcagaac gccttcatca tctataccta acgccttacc   3000
gtaaaaggtt ccgtttaacg ttctggctct catattagtg ccaataccga gcgcatagct   3060
ttcccataaa agcttaatcg gcgtaaatcc gtgcgtcata taatcccggt accgtttctc   3120
aaagcatagt aaaatatgct ggatgacgcc ggcccgatca attttttccc cagcagcttg   3180
gctgaggctt gtcgcgatgt ccttcaattc atctggaaaa tcattaggct gctggttaaa   3240
cggtctccag cttggctgtt ttggcggatg agagaagatt ttcagcctga tacagattaa   3300
atcagaacgc agaagcggtc tgataaaaca gaatttgcct ggcggcagta gcgcggtggt   3360
cccacctgac cccatgccga actcagaagt gaaacgccgt agcgccgatg gtagtgtggg   3420
gtctccccat gcgagagtag ggaactgcca ggcatcaaat aaaacgaaag gctcagtcga   3480
aagactgggc ctttcgtttt atctgttgtt tgtcggtgaa cgctctcctg agtaggacaa   3540
atccgccggg agcggatttg aacgttgcga agcaacggcc cggagggtgg cgggcaggac   3600
gcccgccata aactgccagg catcaaatta agcagaaggc catcctgacg gatggccttt   3660
ttgcgtttct acaaactctt tttgtttatt tttctaaata cattcaaata tgtatccgct   3720
catgagacaa taaccctgat aaatgcttca ataatattga aaaggaaga gtatgagtat   3780
tcaacatttc cgtgtcgccc ttattccctt ttttgcggca ttttgccttc ctgtttttgc   3840
tcacccagaa acgctggtga agtaaaaga tgctgaagat cagttgggtg cacgagtggg   3900
ttacatcgaa ctggatctca acagcggtaa gatccttgag agttttcgcc ccgaagaacg   3960
ttttccaatg atgagcactt ttaaagttct gctatgtggc gcggtattat cccgtgttga   4020
cgccgggcaa gagcaactcg gtcgccgcat acactattct cagaatgact tggttgagta   4080
ctcaccagtc acagaaaagc atcttacgga tggcatgaca gtaagagaat tatgcagtgc   4140
tgccataacc atgagtgata acactgcggc caacttactt ctgacaacga tcggaggacc   4200
gaaggagcta accgcttttt tgcacaacat gggggatcat gtaactcgcc ttgatcgttg   4260
ggaaccggag ctgaatgaag ccataccaaa cgacgagcgt gacaccacga tgcctgtagc   4320
aatggcaaca acgttgcgca aactattaac tggcgaacta cttactctag cttcccggca   4380
acaattaata gactggatgg aggcggataa agttgcagga ccacttctgc gctcggccct   4440
tccggctggc tggtttattg ctgataaatc tggagccggt gagcgtgggt ctcgcggtat   4500
cattgcagca ctggggccag atggtaagcc ctcccgtatc gtagttatct acacgacggg   4560
gagtcaggca actatggatg aacgaaatag acagatcgct gagataggtg cctcactgat   4620
taagcattgg taactgtcag accaagttta ctcatatata ctttagattg atttaaaact   4680
tcatttttaa tttaaaagga tctaggtgaa gatcctttt gataatctca tgaccaaaat   4740
cccttaacgt gagttttcgt tccactgagc gtcagacccc gtagaaaaga tcaaaggatc   4800
ttcttgagat cctttttttc tgcgcgtaat ctgctgcttg caaacaaaaa aaccaccgct   4860
accagcggtg gtttgtttgc cggatcaaga gctaccaact cttttccga aggtaactgg   4920
cttcagcaga gcgcagatac caaatactgt ccttctagtg tagccgtagt taggccacca   4980
cttcaagaac tctgtagcac cgcctacata cctcgctctg ctaatcctgt taccagtggc   5040
tgctgccagt ggcgataagt cgtgtcttac cgggttggac tcaagacgat agttaccgga   5100
taaggcgcag cggtcgggct gaacggggg ttcgtgcaca cagcccagct tggagcgaac   5160
gacctacacc gaactgagat acctacagcg tgagctatga gaaagcgcca cgcttcccga   5220
agggagaaag gcggacaggt atccggtaag cggcagggtc ggaacaggag agcgcacgag   5280
ggagcttcca gggggaaacg cctggtatct ttatagtcct gtcgggtttc gccacctctg   5340
```

-continued

| | |
|---|---|
| acttgagcgt cgattttttgt gatgctcgtc aggggggcgg agcctatgga aaaacgccag | 5400 |
| caacgcggcc ttttttacggt tcctggcctt ttgctggcct tttgctcaca tgttctttcc | 5460 |
| tgcgttatcc cctgattctg tggataaccg tattaccgcc tttgagtgag ctgataccgc | 5520 |
| tcgccgcagc cgaacgaccg agcgcagcga gtcagtgagc gaggaagcgg aagagcgcct | 5580 |
| gatgcggtat tttctcctta cgcatctgtg cggtatttca caccgcatat ggtgcactct | 5640 |
| cagtacaatc tgctctgatg ccgcatagtt aagccagtat acactccgct atcgctacgt | 5700 |
| gactgggtca tggctgcgcc ccgacacccg ccaacacccg ctgacgcgcc ctgacgggct | 5760 |
| tgtctgctcc cggcatccgc ttacagacaa gctgtgaccg tctccgggag ctgcatgtgt | 5820 |
| cagaggtttt caccgtcatc accgaaacgc gcgaggcagc agatcaattc gcgcgcgaag | 5880 |
| gcgaagcggc atgcataatg tgcctgtcaa atggacgaag cagggattct gcaaacccta | 5940 |
| tgctactccg tcaagccgtc aattgtctga ttcgttacca attatgacaa cttgacggct | 6000 |
| acatcattca ctttttcttc acaaccggca cggaactcgc tcgggctggc cccggtgcat | 6060 |
| ttttttaaata cccgcgagaa atagagttga tcgtcaaaac caacattgcg accgacggtg | 6120 |
| gcgataggca tccgggtggt gctcaaaagc agcttcgcct ggctgatacg ttggtcctcg | 6180 |
| cgccagctta agacgctaat ccctaactgc tggcggaaaa gatgtgacag acgcgacggc | 6240 |
| gacaagcaaa catgctgtgc gacgctggcg atatcaaaat tgctgtctgc caggtgatcg | 6300 |
| ctgatgtact gacaagcctc gcgtacccga ttatccatcg gtggatggag cgactcgtta | 6360 |
| atcgcttcca tgcgccgcag taacaattgc tcaagcagat ttatcgccag cagctccgaa | 6420 |
| tagcgccctt ccccttgccc ggcgttaatg atttgcccaa acaggtcgct gaaatgcggc | 6480 |
| tggtgcgctt catccgggcg aaagaacccc gtattgcaa atattgacgg ccagttaagc | 6540 |
| cattcatgcc agtaggcgcg cggacgaaag taaacccact ggtgatacca ttcgcgagcc | 6600 |
| tccgatgac gaccgtagtg atgaatctct cctggcggga acagcaaaat atcacccggt | 6660 |
| cggcaaacaa attctcgtcc ctgattttc accaccccct gaccgcgaat ggtgagattg | 6720 |
| agaatataac ctttcattcc cagcggtcgg tcgataaaaa aatcgagata accgttggcc | 6780 |
| tcaatcggcg ttaaacccgc caccagatgg gcattaaacg agtatcccgg cagcagggga | 6840 |
| tcattttgcg cttcagccat acttttcata ctcccgccat tcagag | 6886 |

<210> SEQ ID NO 21
<211> LENGTH: 7140
<212> TYPE: DNA
<213> ORGANISM: Artificial Sequence
<220> FEATURE:
<223> OTHER INFORMATION: Description of Artificial Sequence: vector
<220> FEATURE:
<223> OTHER INFORMATION: pAN620

<400> SEQUENCE: 21

| | |
|---|---|
| tcggcggccg cttcgtcgac cgaaacagca gttataaggc atgaagctgt ccggtttttg | 60 |
| caaaagtggc tgtgactgta aaagaaatc gaaaaagacc gttttgtgtg aaaacggtct | 120 |
| ttttgtttcc ttttaaccaa ctgccataac tcgaggccta cctagcttcc aagaaagata | 180 |
| tcctaacagc acaagagcgg aaagatgttt tgttctacat ccagaacaac ctctgctaaa | 240 |
| attcctgaaa aattttgcaa aaagttgttg actttatcta caaggtgtgg tataataatc | 300 |
| ttaacaacag caggacgctc tagattagaa aggaggattt aaatatgaga cagattactg | 360 |
| atatttcaca gctgaaagaa gccataaaac aataccattg agagggcaag tcaatcggat | 420 |

-continued

```
ttgttccgac gatggggttt ctgcatgagg ggcatttaac cttagcagac aaagcaagac    480
aagaaaacga cgccgttatt atgagtattt ttgtgaatcc tgcacaattc ggccctaatg    540
aagattttga agcatatccg cgcgatattg agcgggatgc agctcttgca gaaaacgccg    600
gagtcgatat tcttttacg ccagatgctc atgatatgta tcccggtgaa aagaatgtca    660
cgattcatgt agaaagacgc acagacgtgt tatgcgggcg ctcaagagaa ggacattttg    720
acggggtcgc gatcgtactg acgaagcttt tcaatctagt caagccgact cgtgcctatt    780
tcggtttaaa agatgcgcag caggtagctg ttgttgatgg gttaatcagc gacttcttca    840
tggatattga attggttcct gtcgatacga tcagagagga agacggctta gccaaaagct    900
ctcgcaatgt atacttaaca gctgaggaaa gaaagaagc gcctaagctg tatcgggccc    960
ttcaaacaag tgcggaactt gtccaagccg gtgaaagaga tcctgaagcg gtgataaaag   1020
ctgcaaaaga tatcattgaa acgactagcg gaaccataga ctatgtagag ctttattcct   1080
atccggaact cgagcctgtg aatgaaattg ctggaaagat gattctcgct gttgcagttg   1140
ctttttcaaa agcgcgttta atagataata tcattattga tattcgtaga aaggaggtga   1200
attaatatgt atcgtacgat gatgagcggc aaacttcaca gggcaactgt tacgaagca   1260 aacctgaact atgtgggaag cattacaatt gatgaagatc tcattgatgc tgtgggaatg   1320
cttcctaatg aaaaagtaca aattgtgaat aataataatg gagcacgtct tgaaacgtat   1380
attattcctg gtaaacgggg aagcggcgtc atatgcttaa acggtgcagc cgcacgcctt   1440
gtgcaggaag gagataaggt cattattatt tcctacaaaa tgatgtctga tcaagaagcg   1500
gcaagccatg agccgaaagt ggctgttctg aatgatcaaa acaaaattga acaaatgctg   1560
gggaacgaac cagcccgtac aattttgtaa aggatcctgt tttggcggat gagagaagat   1620
tttcagcctg atacagatta aatcagaacg cagaagcggt ctgataaaac agaatttgcc   1680
tggcggcagt agcgcggtgg tcccacctga ccccatgccg aactcagaag tgaaacgccg   1740
tagcgccgat ggtagtgtgg ggtctcccca tgcgagagta gggaactgcc aggcatcaaa   1800
taaaacgaaa ggctcagtcg aaagactggg cctttcgttt tatctgttgt ttgtcggtga   1860
acgctctcct gagtaggaca aatccgccgg gagcggattt gaacgttgcg aagcaacggc   1920
ccggagggtg gcgggcagga cgcccgccat aaactgccag gcatcaaatt aagcagaagg   1980
ccatcctgac ggatggcctt tttgcgtttc tacaaactct tggtaccgag acgatcgtcc   2040
tctttgttgt agcccatcac ttttgctgaa gagtaggagc cgaaagtgac ggcgtattca   2100
ttgagcggca gctgagtcgc accgacagaa atcgcttctc ttgatgtgcc cggcgatccg   2160
actgtccagc cgttcggtcc gctgttgccg tttgaggtaa cagcgacaac gccttctgac   2220
atggcccagt caagcgctgt gcttgtcgcc cagtccgggt tgtttaaaga gtttccgaga   2280
gacaggttca tcacatctgc cccgtcctgc actgcacgtt ccacgcccgc gatgacgttt   2340
tccgttgtgc cgcttccgcc aggccctaac acacgataag caagaagtgt ggcatcaggc   2400
gctacgcctt taatcgttcc gtttgcagcc acagttccgg ctacgtgtgt gccatggtca   2460
gttgcctcgc ccctcggatc gccggttggt gttttctttg gatcgtaatc attgtccaca   2520
aaatcgtatc ctttatattg tccaaagttt ttcttcagat ctgggtgatt gtattcaacc   2580
ccagtgtcaa taatcgccac cttgatgcct tttcctgtgt agcctaaatc ccatgcatcg   2640
tttgctccga tataaggcgc actgtcatcc atttgcggag atacggcgtc ttcggagatt   2700
gtggggaatt ctcatgtttg acagcttatc atgcaatagt tacccttatt atcaagataa   2760
gaaagaaaag gattttttcgc tacgctcaaa tcctttaaaa aaacacaaaa gaccacatt   2820
```

```
tttaatgtgg tctttattct tcaactaaag cacccattag ttcaacaaac gaaaattgga    2880
taaagtggga tattttaaa atatatattt atgttacagt aatattgact tttaaaaaag     2940
gattgattct aatgaagaaa gcagacaagt aagcctccta aattcacttt agataaaaat   3000
ttaggaggca tatcaaatga actttaataa aattgattta gacaattgga agagaaaaga  3060
gatatttaat cattatttga accaacaaac gactttagt ataaccacag aaattgatat    3120
tagtgtttta taccgaaaca taaaacaaga aggatataaa ttttaccctg catttatttt  3180
cttagtgaca agggtgataa actcaaatac agcttttaga actggttaca atagcgacgg  3240
agagttaggt tattgggata agttagagcc actttataca attttgatg gtgtatctaa   3300
aacattctct ggtatttgga ctcctgtaaa gaatgacttc aaagagtttt atgatttata  3360
cctttctgat gtagagaaat ataatggttc ggggaaattg tttcccaaaa cacctatacc  3420
tgaaaatgct ttttctcttt ctattattcc atggacttca tttactgggt ttaacttaaa  3480
tatcaataat aatagtaatt accttctacc cattattaca gcaggaaaat tcattaataa  3540
aggtaattca atatatttac cgctatcttt acaggtacat cattctgttt gtgatggtta  3600
tcatgcagga ttgtttatga actctattca ggaattgtca gataggccta atgactggct  3660
tttataatat gagataatgc cgactgtact ttttacagtc ggttttctaa tgtcactaac  3720
ctgccccgtt agttgaagaa cgaagcggcc gcaattcttg aagacgaaag ggcctcgtga  3780
tacgcctatt tttataggtt aatgtcatga taataatggt ttcttagacg tcaggtggca  3840
cttttcgggg aaatgtgcgc ggaacccta tttgtttatt tttctaaata cattcaaata   3900
tgtatccgct catgagacaa taaccctgat aaatgcttca ataatattga aaaggaaga   3960
gtatgagtat tcaacatttc cgtgtcgccc ttattccctt ttttgcggca ttttgccttc  4020
ctgttttgc tcacccagaa acgctggtga agtaaaaga tgctgaagat cagttgggtg   4080
cacgagtggg ttacatcgaa ctggatctca acagcggtaa gatccttgag agttttcgcc  4140
ccgaagaacg ttttccaatg atgagcactt ttaaagttct gctatgtggc gcggtattat  4200
cccgtattga cgccgggcaa gagcaactcg gtcgccgcat acactattct cagaatgact  4260
tggttgagta ctcaccagtc acagaaaagc atcttacgga tggcatgaca gtaagagaat  4320
tatgcagtgc tgccataacc atgagtgata acactgcggc caacttactt ctgacaacga  4380
tcggaggacc gaaggagcta accgcttttt tgcacaacat gggggatcat gtaactcgcc  4440
ttgatcgttg ggaaccggag ctgaatgaag ccataccaaa cgacgagcgt gacaccacga  4500
tgcctgcagc aatggcaaca acgttgcgca aactattaac tggcgaacta cttactctag  4560
cttcccggca caattaata gactggatgg aggcggataa agttgcagga ccacttctgc  4620
gctcggccct tccggctggc tggtttattg ctgataaatc tggagccggt gagcgtgggt  4680
ctcgcggtat cattgcagca ctggggccag atggtaagcc ctcccgtatc gtagttatct  4740
acacgacggg gagtcaggca actatggatg aacgaaatag acagatcgct gagataggtg  4800
cctcactgat taagcattgg taactgtcag accaagttta ctcatatata ctttagattg  4860
atttaaaact tcattttaa tttaaaagga tctaggtgaa gatcctttt gataatctca   4920
tgaccaaaat cccttaacgt gagttttcgt tccactgagc gtcagacccc gtagaaaaga  4980
tcaaaggatc ttcttgagat cctttttttc tgcgcgtaat ctgctgcttg caaacaaaaa  5040
aaccaccgct accagcggtg gtttgtttgc cggatcaaga gctaccaact cttttttcga  5100
aggtaactgg cttcagcaga gcgcagatac caaatactgt ccttctagtg tagccgtagt  5160
```

```
taggccacca cttcaagaac tctgtagcac cgcctacata cctcgctctg ctaatcctgt   5220
taccagtggc tgctgccagt ggcgataagt cgtgtcttac cgggttggac tcaagacgat   5280
agttaccgga taaggcgcag cggtcgggct gaacggggggg ttcgtgcaca cagcccagct   5340
tggagcgaac gacctacacc gaactgagat acctacagcg tgagctatga gaaagcgcca   5400
cgcttcccga aggagaaag gcggacaggt atccggtaag cggcagggtc ggaacaggag   5460
agcgcacgag ggagcttcca ggggggaaacg cctggtatct ttatagtcct gtcgggtttc   5520
gccacctctg acttgagcgt cgattttttgt gatgctcgtc aggggggcgg agcctatgga   5580
aaaacgccag caacgcggcc ttttttacggt tcctggcctt ttgctggcct tttgctcaca   5640
tgttctttcc tgcgttatcc cctgattctg tggataaccg tattaccgcc tttgagtgag   5700
ctgataccgc tcgccgcagc cgaacgaccg agcgcagcga gtcagtgagc gaggaagcgg   5760
aagagcgcct gatgcggtat tttctcctta cgcatctgtg cggtatttca caccgcatat   5820
ggtgcactct cagtacaatc tgctctgatg ccgcatagtt aagccagtat acactccgct   5880
atcgctacgt gactgggtca tggctgcgcc ccgacacccg ccaacacccg ctgacgcgcc   5940
ctgacgggct tgtctgctcc cggcatccgc ttacagacaa gctgtgaccg tctccgggag   6000
ctgcatgtgt cagaggtttt caccgtcatc accgaaacgc gcgaggcagc tgcggtaaag   6060
ctcatcagcg tggtcgtgaa gcgattcaca gatgtctgcc tgttcatccg cgtccagctc   6120
gttgagtttc tccagaagcg ttaatgtctg gcttctgata aagcgggcca tgttaagggc   6180
ggttttttcc tgtttggtca cttgatgcct ccgtgtaagg gggaatttct gttcatgggg   6240
gtaatgatac cgatgaaacg agagaggatg ctcacgatac gggttactga tgatgaacat   6300
gcccggttac tggaacgttg tgagggtaaa caactggcgg tatggatgcg gcgggaccag   6360
agaaaaatca ctcagggtca atgccagcgc ttcgttaata cagatgtagg tgttccacag   6420
ggtagccagc agcatcctgc gatgcagatc cggaacataa tggtgcaggg cgctgacttc   6480
cgcgtttcca gactttacga aacacggaaa ccgaagacca ttcatgttgt tgctcaggtc   6540
gcagacgttt tgcagcagca gtcgcttcac gttcgctcgc gtatcggtga ttcattctgc   6600
taaccagtaa ggcaaccccg ccagcctagc cgggtcctca acgacaggag cacgatcatg   6660
cgcacccgtg gccaggaccc aacgctgccc gagatgcgcc gcgtgcggct gctggagatg   6720
gcggacgcga tggatatgtt ctgccaaggg ttggtttgcg cattcacagt tctccgcaag   6780
aattgattgg ctccaattct tggagtggtg aatccgttag cgaggtgccg ccggcttcca   6840
ttcaggtcga ggtggcccgg ctccatgcac cgcgacgcaa cgcggggagg cagacaaggt   6900 ataggggcggc gcctacaatc catgccaacc cgttccatgt gctcgccgag gcggcataaa   6960
tcgccgtgac gatcagcggt ccagtgatcg aagttaggct ggtaagagcc gcgagcgatc   7020
cttgaagctg tccctgatgg tcgtcatcta cctgcctgga cagcatggcc tgcaacgcgg   7080
gcatcccgat gccgccggaa gcgagaagaa tcataatggg gaaggccatc cagcctcgcg   7140
```

<210> SEQ ID NO 22
<211> LENGTH: 6725
<212> TYPE: DNA
<213> ORGANISM: Artificial Sequence
<220> FEATURE:
<223> OTHER INFORMATION: Description of Artificial Sequence: vector
<220> FEATURE:
<223> OTHER INFORMATION: pAN636

<400> SEQUENCE: 22

```
tcggcggccg cttcgtcgac cgaaacagca gttataaggc atgaagctgt ccggtttttg      60
```

-continued

```
caaaagtggc tgtgactgta aaagaaatc gaaaaagacc gttttgtgtg aaaacggtct    120
ttttgttttcc ttttaaccaa ctgccataac tcgaggccta cctagcttcc aagaaagata   180
tcctaacagc acaagagcgg aaagatgttt tgttctacat ccagaacaac ctctgctaaa    240
attcctgaaa aattttgcaa aaagttgttg actttatcta caaggtgtgg tataataatc    300
ttaacaacag caggacgctc tagaaggagg agaaaacatg aaaacaaaac tggattttct    360
aaaaatgaag gagtctgaag aaccgattgt catgctgacc gcttatgatt atccggcagc    420
taaacttgct gaacaagcgg gagttgacat gattttagtc ggtgattcac ttggaatggt    480
cgtcctcggc cttgattcaa ctgtcggtgt gacagttgcg gacatgatcc atcatacaaa    540
agccgttaaa agggtgcgc cgaatacctt tattgtgaca gatatgccgt ttatgtctta     600
tcacctgtct aaggaagata cgctgaaaaa tgcagcggct atcgttcagg aaagcggagc    660
tgacgcactg aagcttgagg cggagaagg cgtgtttgaa tccattcgcg cattgacgct     720
tggaggcatt ccagtagtca gtcacttagg tttgacaccg cagtcagtcg gcgtactggg    780
cggctataaa gtacagggca agacgaaca aagcgccaaa aaattaatag aagcacagtat   840
aaaatgcgaa gaagcaggag ctatgatgct tgtgctggaa tgtgtgccgg cagaactcac    900
agccaaaatt gccgagacgc taagcatacc ggtcattgga atcggggctg gtgtgaaagc    960
ggacggacaa gttctcgttt atcatgatat tatcggccac ggtgttgaga gaacacctaa   1020
atttgtaaag caatatacgc gcattgatga aaccatcgaa acagcaatca gcggatatgt   1080
tcaggatgta agacatcgtg ctttccctga acaaaagcat tcctttcaaa tgaaccagac   1140
agtgcttgac ggcttgtacg ggggaaaata agggggggat cctgttttgg cggatgagag   1200
aagattttca gcctgataca gattaaatca gaacgcagaa gcggtctgat aaaacagaat   1260
ttgcctggcg gcagtagcgc ggtggtccca cctgaccca tgccgaactc agaagtgaaa    1320
cgccgtagcg ccgatggtag tgtggggtct ccccatgcga gagtagggaa ctgccaggca   1380
tcaaataaaa cgaaaggctc agtcgaaaga ctgggccttt cgttttatct gttgtttgtc   1440
ggtgaacgct ctcctgagta ggacaaatcc gccgggagcg gatttgaacg ttgcgaagca   1500
acggcccgga gggtggcggg caggacgccc gccataaact gccaggcatc aaattaagca   1560
gaaggccatc ctgacggatg ccttttttgc gtttctacaa actcttggta ccagacgat    1620
cgtcctcttt gttgtagccc atcacttttg ctgaagagta ggagccgaaa gtgacggcgt   1680
attcattgag cggcagctga gtcgcaccga cagaaatcgc ttctcttgat gtgcccggcg   1740
atccgactgt ccagccgttc ggtccgctgt tgccgtttga ggtaacagcg acaacgcctt   1800
ctgcacatggc ccagtcaagc gctgtgcttg tcgcccagtc cgggttgttt aaagagtttc   1860
cgagagacag gttcatcaca tctgccccgt cctgcactgc acgttccacg cccgcgatga   1920
cgttttccgt tgtgccgctt ccgccaggcc ctaacacacg ataagcaaga agtgtggcat   1980
caggcgctac gcctttaatc gttccgtttg cagccacagt tccggctacg tgtgtgccat   2040
ggtcagttgc ctcgcccctc ggatcgccgg ttggtgtttc ttttggatcg taatcattgt    2100
ccacaaaatc gtatccttta tattgtccaa agtttttctt cagatctggg tgattgtatt   2160
caaccccagt gtcaataatc gccaccttga tgccttttcc tgtgtagcct aaatcccatg   2220
catcgtttgc tccgatataa ggcgcactgt catccatttg cggagatacg gcgtcttcgg   2280
agattgtggg gaattctcat gtttgacagc ttatcatgca ataggtaccc ttattatcaa   2340
gataagaaag aaaaggattt ttcgctacgc tcaaatcctt taaaaaaaca caaaagacca   2400
```

```
catttttttaa tgtggtcttt attcttcaac taaagcaccc attagttcaa caaacgaaaa   2460
ttggataaag tgggatattt ttaaaatata tatttatgtt acagtaatat tgactttaa     2520 aaaaggattg attctaatga agaaagcaga caagtaagcc tcctaaattc actttagata   2580
aaaatttagg aggcatatca aatgaacttt aataaaattg atttagacaa ttggaagaga   2640
aaagagatat ttaatcatta tttgaaccaa caaacgactt ttagtataac cacagaaatt   2700
gatattagtg ttttataccg aaacataaaa caagaaggat ataaatttta ccctgcattt   2760
attttcttag tgacaagggt gataaactca atacagcttt ttagaactgg ttacaatagc   2820
gacggagagt taggttattg ggataagtta gagccacttt atacaatttt tgatggtgta   2880
tctaaaacat tctctggtat ttggactcct gtaagaatg acttcaaaga gttttatgat    2940 ttatacctt ctgatgtaga gaaatataat ggttcgggga aattgttcc caaaacaccct   3000 atacctgaaa atgcttttt tctttctatt attccatgga cttcatttac tgggtttaac   3060
ttaaatatca ataataatag taattacctt ctacccatta ttacagcagg aaaattcatt   3120
aataaaggta attcaatata tttaccgcta tctttacagg tacatcattc tgtttgtgat   3180
ggttatcatg caggattgtt tatgaactct attcaggaat tgtcagatag gcctaatgac   3240
tggcttttat aatatgagat aatgccgact gtacttttta cagtcggttt tctaatgtca   3300
ctaacctgcc ccgttagttg aagaacgaag cggccgcaat tcttgaagac gaaagggcct   3360
cgtgatacgc ctatttttat aggttaatgt catgataata atggtttctt agacgtcagg   3420
tggcactttt cggggaaatg tgcgcggaac ccctatttgt ttatttttct aaatacattc   3480
aaatatgtat ccgctcatga gacaataacc ctgataaatg cttcaataat attgaaaaag   3540
gaagagtatg agtattcaac atttccgtgt cgcccttatt cccttttttg cggcattttg   3600
ccttcctgtt tttgctcacc cagaaacgct ggtgaaagta aaagatgctg aagatcagtt   3660
gggtgcacga gtgggttaca tcgaactgga tctcaacagc ggtaagatcc ttgagagttt   3720
tcgccccgaa gaacgttttc caatgatgag cacttttaaa gttctgctat gtggcgcggt   3780
attatcccgt attgacgccg ggcaagagca actcggtcgc cgcatacact attctcagaa   3840
tgacttggtt gagtactcac cagtcacaga aaagcatctt acggatggca tgacagtaag   3900
agaattatgc agtgctgcca taaccatgag tgataacact gcggccaact tacttctgac   3960
aacgatcgga ggaccgaagg agctaaccgc ttttttgcac aacatggggg atcatgtaac   4020
tcgccttgat cgttgggaac cggagctgaa tgaagccata ccaaacgacg agcgtgacac   4080
cacgatgcct gcagcaatgg caacaacgtt gcgcaaacta ttaactggcg aactacttac   4140
tctagcttcc cggcaacaat taatagactg gatggaggcg gataaagttg caggaccact   4200
tctgcgctcg gcccttccgg ctggctggtt tattgctgat aaatctggag ccggtgagcg   4260
tgggtctcgc ggtatcattg cagcactggg gccagatggt aagccctccc gtatcgtagt   4320
tatctacacg acggggagtc aggcaactat ggatgaacga atagacaga tcgctgagat    4380 aggtgcctca ctgattaagc attggtaact gtcagaccaa gtttactcat atatacttta   4440
gattgattta aaacttcatt tttaatttaa aaggatctag gtgaagatcc ttttttgataa   4500 tctcatgacc aaaatccctt aacgtgagtt ttcgttccac tgagcgtcag acccgtaga    4560 aaagatcaaa ggatcttctt gagatccttt ttttctgcgc gtaatctgct gcttgcaaac   4620
aaaaaaacca ccgctaccag cggtggtttg tttgccggat caagagctac caactctttt   4680
tccgaaggta actggcttca gcagagcgca gataccaaat actgtccttc tagtgtagcc   4740
gtagttaggc caccacttca agaactctgt agcaccgcct acatacctcg ctctgctaat   4800
```

```
cctgttacca gtggctgctg ccagtggcga taagtcgtgt cttaccgggt tggactcaag    4860
acgatagtta ccggataagg cgcagcggtc gggctgaacg ggggtcgt gcacacagcc      4920 cagcttggag cgaacgacct acaccgaact gagatacca cagcgtgagc tatgagaaag     4980
cgccacgctt cccgaaggga gaaaggcgga caggtatccg gtaagcggca gggtcggaac   5040
aggagagcgc acgagggagc ttccagggg aaacgcctgg tatctttata gtcctgtcgg     5100
gtttcgccac ctctgacttg agcgtcgatt tttgtgatgc tcgtcagggg ggcggagcct    5160
atggaaaaac gccagcaacg cggccttttt acggttcctg gcctttttgct ggccttttgc    5220 tcacatgttc tttcctgcgt tatcccctga ttctgtggat aaccgtatta ccgcctttga    5280
gtgagctgat accgctcgcc gcagccgaac gaccgagcgc agcgagtcag tgagcgagga   5340
agcggaagag cgcctgatgc ggtatttct ccttacgcat ctgtgcggta tttcacaccg      5400
catatggtgc actctcagta caatctgctc tgatgccgca tagttaagcc agtatacact    5460
ccgctatcgc tacgtgactg ggtcatggct gcgccccgac acccgccaac acccgctgac   5520
gcgccctgac gggcttgtct gctcccggca tccgcttaca gacaagctgt gaccgtctcc     5580
gggagctgca tgtgtcagag gttttcaccg tcatcaccga aacgcgcgag gcagctgcgg   5640
taaagctcat cagcgtggtc gtgaagcgat tcacagatgt ctgcctgttc atccgcgtcc    5700
agctcgttga gtttctccag aagcgttaat gtctggcttc tgataaagcg ggccatgtta   5760
agggcggttt tttcctgtttt ggtcacttga tgcctccgtg taaggggaa tttctgttca    5820 tgggggtaat gataccgatg aaacgagaga ggatgctcac gatacgggtt actgatgatg   5880
aacatgcccg gttactggaa cgttgtgagg gtaaacaact ggcggtatgg atgcggcggg    5940
accagagaaa aatcactcag ggtcaatgcc agcgcttcgt taatacagat gtaggtgttc    6000
cacagggtag ccagcagcat cctgcgatgc agatccggaa cataatggtg cagggcgctg   6060
acttccgcgt ttccagactt tacgaaacac ggaaaccgaa gaccattcat gttgttgctc     6120
aggtcgcaga cgttttgcag cagcagtcgc ttcacgttcg ctcgcgtatc ggtgattcat     6180
tctgctaacc agtaaggcaa ccccgccagc ctagccgggt cctcaacgac aggagcacga    6240
tcatgcgcac ccgtggccag gacccaacgc tgcccgagat gcgccgcgtg cggctgctgg    6300
agatggcgga cgcgatggat atgttctgcc aagggttggt ttgcgcattc acagttctcc    6360
gcaagaattg attggctcca attcttggag tggtgaatcc gttagcgagg tgccgccggc    6420
ttccattcag gtcgaggtgg cccggctcca tgcaccgcga cgcaacgcgg ggaggcagac    6480
aaggtatagg gcggcgccta caatccatgc caacccgttc catgtgctcg ccgaggcggc   6540
ataaatcgcc gtgacgatca gcggtccagt gatcgaagtt aggctggtaa gagccgcgag    6600
cgatccttga agctgtccct gatggtcgtc atctacctgc ctggacagca tggcctgcaa    6660
cgcgggcatc ccgatgccgc cggaagcgag aagaatcata tgggggaagg ccatccagcc    6720
tcgcg                                                                6725

<210> SEQ ID NO 23
<211> LENGTH: 6806
<212> TYPE: DNA
<213> ORGANISM: Artificial Sequence
<220> FEATURE:
<223> OTHER INFORMATION: Description of Artificial Sequence: vector
<220> FEATURE:
<223> OTHER INFORMATION: pAN637

<400> SEQUENCE: 23
```

-continued

| | |
|---|---|
| tcggcggccg cttcgtcgac cgaaacagca gttataaggc atgaagctgt ccggttttg | 60 |
| caaaagtggc tgtgactgta aaagaaatc gaaaagacc gttttgtgtg aaaacggtct | 120 |
| ttttgtttcc ttttaaccaa ctgccataac tcgaggccta cctagcttcc aagaaagata | 180 |
| tcctaacagc acaagagcgg aaagatgttt tgttctacat ccagaacaac ctctgctaaa | 240 |
| attcctgaaa aattttgcaa aaagttgttg actttatcta caaggtgtgg tataataatc | 300 |
| ttaacaacag caggacgctc tagacaattg agatcttaag aaaggagtg ttaattaatg | 360 |
| aagattggaa tcattggcgg aggctccgtt ggtcttttat gcgcctatta tttgtcactt | 420 |
| tatcacgacg tgactgttgt gacgaggcgg caagaacagg ctgcggccat tcagtctgaa | 480 |
| ggaatccggc tttataaagg cggggaggaa ttcagggctg attgcagtgc ggacacgagt | 540 |
| atcaattcgg actttgacct gcttgtcgtg acagtgaagc agcatcagct tcaatctgtt | 600 |
| ttttcgtcgc ttgaacgaat cgggaagacg aatatattat ttttgcaaaa cggcatgggg | 660 |
| catatccacg acctaaaaga ctggcacgtt ggccattcca tttatgttgg aatcgttgag | 720 |
| cacggagctg taagaaaatc ggatacagct gttgatcata caggcctagg tgcgataaaa | 780 |
| tggagcgcgt tcgacgatgc tgaaccagac cggctgaaca tcttgtttca gcataaccat | 840 |
| tcggattttc cgatttatta tgagacggat tggtaccgtc tgctgacggg caagctgatt | 900 |
| gtaaatgcgt gtattaatcc tttaactgcg ttattgcaag tgaaaaatgg agaactgctg | 960 |
| acaacgccag cttatctggc ttttatgaag ctggtatttc aggaggcatg ccgcattta | 1020 |
| aaacttgaaa tgaagaaaa ggcttgggag cgggttcagg ccgtttgtgg gcaaacgaaa | 1080 |
| gagaatcgtt catcaatgct ggttgacgtc attggaggcc ggcagacgga agctgacgcc | 1140 |
| attatcggat acttattgaa ggaagcaagt cttcaaggtc ttgatgccgt ccacctagag | 1200 |
| tttttatatg gcagcatcaa agcattggag cgaaatacca acaaagtggt ttactaagga | 1260 |
| tcctgttttg gcggatgaga gaagatttc agcctgatac agattaaatc agaacgcaga | 1320 |
| agcggtctga taaaacagaa tttgcctggc ggcagtagcg cggtggtccc acctgacccc | 1380 |
| atgccgaact cagaagtgaa acgccgtagc gccgatggta gtgtgggtc tccccatgcg | 1440 |
| agagtaggga actgccaggc atcaaataaa cgaaaggct cagtcgaaag actgggcctt | 1500 |
| tcgttttatc tgttgtttgt cggtgaacgc tctcctgagt aggacaaatc cgccgggagc | 1560 |
| ggatttgaac gttgcgaagc aacggcccgg agggtggcgg gcaggacgcc cgccataaac | 1620 |
| tgccaggcat caaattaagc agaaggccat cctgacggat ggcctttttg cgtttctaca | 1680 |
| aactcttggt accgagacga tcgtcctctt tgttgtagcc catcactttt gctgaagagt | 1740 |
| aggagccgaa agtgacggcg tattcattga gcggcagctg agtcgcaccg acagaaatcg | 1800 |
| cttctcttga tgtgcccggc gatccgactg tccagccgtt cggtccgctg ttgccgtttg | 1860 |
| aggtaacagc gacaacgcct tctgacatgg cccagtcaag cgctgtgctt gtcgcccagt | 1920 |
| ccgggttgtt taaagagttt ccgagagaca ggttcatcac atctgccccg tcctgcactg | 1980 |
| cacgttccac gcccgcgatg acgttttccg ttgtgccgct tccgccaggc cctaacacac | 2040 |
| gataagcaag aagtgtggca tcaggcgcta cgcctttaat cgttccgttt gcagccacag | 2100 |
| ttccggctac gtgtgtgcca tggtcagttg cctcgcccct cggatcgccg gttggtgttt | 2160 |
| cttttggatc gtaatcattg tccacaaaat cgtatccttt atattgtcca agttttttct | 2220 |
| tcagatctgg gtgattgtat tcaaccccag tgtcaataat cgccaccttg atgccttttc | 2280 |
| ctgtgtagcc taaatcccat gcatcgtttg ctccgatata aggcgcactg tcatccatt | 2340 |
| gcggagatac ggcgtcttcg gagattgtgg ggaattctca tgtttgacag cttatcatgc | 2400 |

-continued

```
aatagttacc cttattatca agataagaaa gaaaaggatt tttcgctacg ctcaaatcct   2460
ttaaaaaaac acaaaagacc acattttta atgtggtctt tattcttcaa ctaaagcacc    2520
cattagttca acaaacgaaa attggataaa gtgggatatt tttaaaatat atatttatgt   2580
tacagtaata ttgactttta aaaaggatt gattctaatg aagaaagcag acaagtaagc    2640
ctcctaaatt cactttagat aaaaatttag gaggcatatc aaatgaactt taataaaatt   2700
gatttagaca attggaagag aaaagagata tttaatcatt atttgaacca caaacgact    2760 tttagtataa ccacagaaat tgatattagt gtttttatacc gaaacataaa acaagaagga  2820
tataaatttt accctgcatt tattttctta gtgacaaggg tgataaactc aaatacagct   2880
tttagaactg gttacaatag cgacggagag ttaggttatt gggataagtt agagccactt   2940
tatacaattt ttgatggtgt atctaaaaca ttctctggta tttggactcc tgtaaagaat   3000
gacttcaaag agttttatga tttataccgt tctgatgtag agaaatataa tggttcgggg   3060
aaattgtttc ccaaaacacc tatacctgaa aatgcttttt ctctttctat tattccatgg   3120
acttcattta ctgggtttaa cttaaatatc aataataata gtaattaccct tctacccatt   3180 attacagcag gaaaattcat taataaaggt aattcaatat atttaccgct atctttacag   3240
gtacatcatt ctgtttgtga tggttatcat gcaggattgt ttatgaactc tattcaggaa   3300
ttgtcagata ggcctaatga ctggctttta taatatgaga taatgccgac tgtactttt    3360 acagtcggtt ttctaatgtc actaacctgc cccgttagtt gaagaacgaa gcggccgcaa   3420
ttcttgaaga cgaaagggcc tcgtgatacg cctattttta taggttaatg tcatgataat   3480
aatggtttct tagacgtcag gtggcacttt tcggggaaat gtgcgcggaa cccctatttg   3540
tttatttttc taaatacatt caaatatgta tccgctcatg agacaataac cctgataaat   3600
gcttcaataa tattgaaaaa ggaagagtat gagtattcaa catttccgtg tcgcccttat   3660
tccctttttt gcggcatttt gccttcctgt ttttgctcac ccagaaacgc tggtgaaagt   3720
aaaagatgct gaagatcagt tgggtgcacg agtgggttac atcgaactgg atctcaacag   3780
cggtaagatc cttgagagtt ttcgccccga agaacgtttt ccaatgatga gcacttttaa   3840
agttctgcta tgtggcgcgg tattatcccg tattgacgcc gggcaagagc aactcggtcg   3900
ccgcatacac tattctcaga atgacttggt tgagtactca ccagtcacag aaaagcatct   3960
tacggatggc atgacagtaa gagaattatg cagtgctgcc ataaccatga gtgataacac   4020
tgcggccaac ttacttctga caacgatcgg aggaccgaag gagctaaccg cttttttgca   4080
caacatgggg gatcatgtaa ctcgccttga tcgttgggaa ccggagctga atgaagccat   4140
accaaacgac gagcgtgaca ccacgatgcc tgcagcaatg gcaacaacgt tgcgcaaact   4200
attaactggc gaactactta ctctagcttc ccggcaacaa ttaatagact ggatggaggc   4260
ggataaagtt gcaggaccac ttctgcgctc ggcccttccg gctggctggt ttattgctga   4320
taaatctgga gccggtgagc gtgggtctcg cggtatcatt gcagcactgg ggccagatgg   4380
taagccctcc cgtatcgtag ttatctacac gacggggagt caggcaacta tggatgaacg   4440
aaatagacag atcgctgaga taggtgcctc actgattaag cattggtaac tgtcagacca   4500
agtttactca tatatacttt agattgattt aaaacttcat ttttaattta aaaggatcta   4560
ggtgaagatc cttttttgata atctcatgac caaaatccct taacgtgagt tttcgttcca   4620
ctgagcgtca gaccccgtag aaaagatcaa aggatcttct tgagatcctt ttttctgcg    4680 cgtaatctgc tgcttgcaaa caaaaaaacc accgctacca gcggtggttt gtttgccgga   4740
```

```
tcaagagcta ccaactctttt ttccgaaggt aactggcttc agcagagcgc agataccaaa    4800
tactgtcctt ctagtgtagc cgtagttagg ccaccacttc aagaactctg tagcaccgcc    4860
tacataccctc gctctgctaa tcctgttacc agtggctgct gccagtgcgc ataagtcgtg   4920
tcttaccggg ttggactcaa gacgatagtt accggataag gcgcagcggt cgggctgaac    4980
ggggggttcg tgcacacagc ccagcttgga gcgaacgacc tacaccgaac tgagataccct   5040
acagcgtgag ctatgagaaa gcgccacgct tcccgaaggg agaaaggcgg acaggtatcc    5100
ggtaagcggc agggtcggaa caggagagcg cacgagggag cttccagggg gaaacgcctg    5160
gtatctttat agtcctgtcg ggtttcgcca cctctgactt gagcgtcgat ttttgtgatg    5220
ctcgtcaggg gggcggagcc tatggaaaaa cgccagcaac gcggcctttt tacggttcct    5280
ggccttttgc tggcctttg ctcacatgtt ctttcctgcg ttatccctg attctgtgga     5340
taaccgtatt accgcctttg agtgagctga taccgctcgc cgcagccgaa cgaccgagcg    5400
cagcgagtca gtgagcgagg aagcggaaga gcgcctgatg cggtattttc tccttacgca    5460
tctgtgcggt atttcacacc gcatatggtg cactctcagt acaatctgct ctgatgccgc    5520
atagttaagc cagtatacac tccgctatcg ctacgtgact gggtcatggc tgcgccccga    5580
cacccgccaa cacccgctga cgcgccctga cgggcttgtc tgctcccggc atccgcttac    5640
agacaagctg tgaccgtctc cgggagctgc atgtgtcaga ggttttcacc gtcatcaccg    5700
aaacgcgcga ggcagctgcg gtaaagctca tcagcgtggt cgtgaagcga ttcacagatg    5760
tctgcctgtt catccgcgtc cagctcgttg agtttctcca gaagcgttaa tgtctggctt    5820
ctgataaagc gggccatgtt aagggcggtt ttttcctgtt tggtcacttg atgcctccgt    5880
gtaaggggga atttctgttc atgggggtaa tgataccgat gaaacgagag aggatgctca    5940
cgatacgggt tactgatgat gaacatgccc ggttactgga acgttgtgag ggtaaacaac    6000
tggcggtatg gatgcggcgg gaccagagaa aaatcactca gggtcaatgc cagcgcttcg    6060
ttaatacaga tgtaggtgtt ccacagggta gccagcagca tcctgcgatg cagatccgga    6120
acataatggt gcagggcgct gacttccgcg tttccagact ttacgaaaca cggaaaccga    6180
agaccattca tgttgttgct caggtcgcag acgttttgca gcagcagtcg cttcacgttc    6240
gctcgcgtat cggtgattca ttctgctaac cagtaaggca accccgccag cctagccggg    6300
tcctcaacga caggagcacg atcatgcgca cccgtggcca ggacccaacg ctgcccgaga    6360
tgcgccgcgt gcggctgctg gagatggcgg acgcgatgga tatgttctgc caagggttgg    6420
tttgcgcatt cacagttctc cgcaagaatt gattggctca aattcttgga gtggtgaatc    6480
cgttagcgag gtgccgccgg cttccattca ggtcgaggtg gcccggctcc atgcaccgcg    6540
acgcaacgcg gggaggcaga caaggtatag gcggcgcct acaatccatg ccaacccgtt    6600
ccatgtgctc gccgaggcgg cataaatcgc cgtgacgatc agcggtccag tgatcgaagt    6660
taggctggta agagccgcga gcgatccttg aagctgtccc tgatggtcgt catctacctg    6720
cctggacagc atggcctgca acgcgggcat cccgatgccg ccggaagcga agaatcat     6780
aatggggaag gccatccagc ctcgcg                                        6806
```

<210> SEQ ID NO 24
<211> LENGTH: 3867
<212> TYPE: DNA
<213> ORGANISM: Artificial Sequence
<220> FEATURE:
<223> OTHER INFORMATION: Description of Artificial Sequence: vector

<400> SEQUENCE: 24

-continued

| | | | | |
|---|---|---|---|---|
| aagctttctc | aagaagcgaa | caagaaaaaa | gaagagcaga | ttaaacagct tcaagagttt | 60 |
| gtcgctagat | tcagcgccaa | tgcgtctaaa | tctaagcagg | ctacatcaag aaagaaactt | 120 |
| ctcgaaaaaa | tcacgctgga | tgatattaaa | ccgtcttccc | gccgctatcc ttatgttaac | 180 |
| ttcacgccgg | aacgggaaat | cggaaatgat | gttcttcgcg | tggaaggctt aacaaaaaca | 240 |
| atcgatggcg | taaggtgct | tgacaatgtc | agctttatta | tgaatcgaga agataaaatt | 300 |
| gctttcactg | gccgaaatga | acttgctgtt | actacgctgt | ttaaaatcat ttccggggaa | 360 |
| atggaagctg | acagcggaac | gtttaaatgg | ggtgttacca | catctcaagc gtattttcca | 420 |
| aaagacaaca | gcgaatattt | cgaaggcagt | gatctgaacc | ttgtagactg gcttcgccaa | 480 |
| tattctccgc | acgaccaaag | tgagagcttt | ttacgcggtt | tcttaggacg catgctgttc | 540 |
| tctggagaag | aagtccacaa | aaaagcaaat | gtactttccg | ggggagaaaaa ggtccgctgt | 600 |
| atgctgtcga | aagcgatgct | ttctggcgcc | aatattttaa | ttttggatga gccgaccaac | 660 |
| catttagacc | tagagtccat | tacagcgctc | aataacggct | taatcagctt taaaggcgct | 720 |
| atgctgttta | cttcccatga | ccatcagttt | gtgcagacca | ttgccaacag aattatagaa | 780 |
| attacaccta | acggcatcgt | cgataagcaa | atgagctatg | acgagttcct tgaaaatgct | 840 |
| gatgtgcaga | aaaaattgac | tgaactatac | gccgaataaa | aaagcagaga tttctctgct | 900 |
| tttttttgata | cctaaatgtg | aaaggagatc | acaacatgaa | atttttggtt gtcggagcag | 960 |
| gtggagtagg | cgggtatatt | ggcggacggc | tttcggagaa | aggaaatgat gtgacatttc | 1020 |
| tcgtgcgcca | aaaacgagct | gagcagctta | aaaaaaccgg | gcttgtcatc catagtgaaa | 1080 |
| aagggaatgt | atcatttcag | cccgaactaa | tcagtgccgg | agaaacaggg caatttgatg | 1140 |
| tcgttatcat | tgcttctaaa | gcatactcgc | ttggtcaagt | gatagaggat gtcaaaccat | 1200 |
| ttatccatca | agaatctgtc | attatccctt | ttttaaatgg | gtaccgccac tatgagcagc | 1260 |
| tatttgcggc | attttcaaaa | gaacaggtgc | tgggcggcct | gtgttttata gaaagtgctt | 1320 |
| tagacaacaa | aggagaaatt | catcatacga | gcgcatcgca | tcgttttgta tttggagaat | 1380 |
| ggaacggcga | gcgtacggag | cggataagag | cgcttgaaga | ggcattttca ggtgtgaagg | 1440 |
| ctgaagtcat | cattagcggg | catatcgaga | agatcccctg | cagcaatagt taccttatt | 1500 |
| atcaagataa | gaaagaaaag | gattttcgc | tacgctcaaa | tcctttaaaa aaacacaaaa | 1560 |
| gaccacattt | tttaatgtgg | tctttattct | tcaactaaag | cacccattag ttcaacaaac | 1620 |
| gaaaattgga | taaagtggga | tatttttaaa | atatatattt | atgttacagt aatattgact | 1680 |
| tttaaaaaag | gattgattct | aatgaagaaa | gcagacaagt | aagcctccta aattcacttt | 1740 |
| agataaaaat | ttaggaggca | tatcaaatga | actttaataa | aattgattta gacaattgga | 1800 |
| agagaaaaga | gatatttaat | cattatttga | accaacaaac | gacttttagt ataaccacag | 1860 |
| aaattgatat | tagtgtttta | taccgaaaca | taaaacaaga | aggatataaa ttttaccctg | 1920 |
| catttatttt | cttagtgaca | agggtgataa | actcaaatac | agcttttaga actggttaca | 1980 |
| atagcgacgg | agagttaggt | tattgggata | agttagagcc | actttataca atttttgatg | 2040 |
| gtgtatctaa | aacattctct | ggtatttgga | ctcctgtaaa | gaatgacttc aaagagtttt | 2100 |
| atgatttata | cctttctgat | gtagagaaat | ataatggttc | ggggaaattg tttcccaaaa | 2160 |
| cacctatacc | tgaaaatgct | ttttctcttt | ctattattcc | atggacttca tttactgggt | 2220 |
| ttaacttaaa | tatcaataat | aatagtaatt | accttctacc | cattattaca gcaggaaaat | 2280 |
| tcattaataa | aggtaattca | atatatttac | cgctatcttt | acaggtacat cattctgttt | 2340 |

```
gtgatggtta tcatgcagga ttgtttatga actctattca ggaattgtca gataggccta    2400
atgactggct tttataatat gagataatgc cgactgtact ttttacagtc ggttttctaa    2460
tgtcactaac ctgccccgtt agttgaagaa ggtttttata ttacagctcc cgggagatct    2520
gggatcacta gtccaaacga cagaaggcga ccacctgcat ggattttga ttgaaaaagc     2580 aaaacgttta tctctcgctg caccagtatt agaaaccgtt tatgcgaatc tgcaaatgta    2640
tgaagcagaa aaataaaaaa aggaggcgga aaagcctcct tttatttact aaaaagccc     2700 aatttccgtt tctgaagata ggctctcttt tcccgtctgc cgtaattccg tcaatattca    2760
tatccttaga accgatcata aagtccacgt gtgtaatgct ttcatttagg ccttctttga    2820
caagctcttc acgagacatc tgcttccgc cttcaatatt aaaggcatag gcgcttccga     2880
tcgccaaatg atttgacgcg ttttcatcaa acagcgtgtt atagaaaaga atgtttgatt    2940
gtgatatagg cgaatcgtaa ggaacaagtg ccacttcacc taaatagtga gaaccttcat    3000
ctgtttccac cagttctttt aaaatatcct caccttttc agcttaatg tcgactatac      3060 ggccattttc aaacgtcagg gtgaaatttt caataatatt tccgccgtag cttaatggtt    3120
ttgtgcttga taccactccg tcaacccgt ctttttgcgg cagcgtgaac acttcttctg     3180
tcggcatatt ggccataaac tcatggccac tttcattcac gcttcccgca cctgcccaaa   3240
catgcttcct aggcagctta attgttagat cagttccttc tgcttgataa tgtaaggcag   3300
cgtaatgtct ctcgttcaaa tggtcaactt tttcatgaag attttggtca tgattgatcc   3360
acgcctgaac cggggttgtct tcattacgc gcgtcgcttt aaaaatttct tcccacagaa    3420
ggtggatcgc ttcctcctct gatttgccag gaaacaccttt gtgagcccag cctgctgatg  3480
ccgcacctac gacagtccag ctgactttgt ctgattgaat atattgtctg tatgtatgta    3540
atgctttgcc tgctgctttt tggaatgccg caatccgttt ggaatctata ccttttagca   3600
agtctgggtt cgacgacaca acagaaatga aagcagctcc attttttgca agctcttctc   3660
tgccttttgc ttcccattca ggatattctt caaatgcttc aaacggcgca agttcgtatt   3720
ttaatttggc gacttcgtca tcctgccaat tcacggtgac gttttttgcg cccttttcat   3780
atgcgtgttt tacaattaaa cggacaaaat cccgaacgtc tgttgaagca tttacgacta   3840
catactggcc tttttggaca ttaacgc                                       3867
```

<210> SEQ ID NO 25
<211> LENGTH: 8704
<212> TYPE: DNA
<213> ORGANISM: Artificial Sequence
<220> FEATURE:
<223> OTHER INFORMATION: Description of Artificial Sequence: vector
<220> FEATURE:
<223> OTHER INFORMATION: pAN238

<400> SEQUENCE: 25

```
gcggccgctt cgtcgaccga acagcagtt ataaggcatg aagctgtccg gtttttgcaa     60
aagtggctgt gactgtaaaa agaaatcgaa aagaccgtt ttgtgtgaaa acggtctttt     120
tgtttccttt taaccaactg ccataactcg aggcctacct agcttccaag aaagatatcc    180
taacagcaca agagcggaaa gatgttttgt tctacatcca gaacaacctc tgctaaaatt    240
cctgaaaaat tttgcaaaaa gttgttgact ttatctacaa ggtgtggtat aataatctta    300
acaacagcag gacgctctag aggaggagac taacatgaaa tttttggttg tcggagcagg   360
tggagtaggc gggtatattg gcggacggct ttccggagaaa ggaaatgatg tgacatttct   420
cgtgcgccaa aaacgagctg agcagcttaa aaaaaccggg cttgtcatcc atagtgaaaa   480
```

-continued

```
agggaatgta tcatttcagc ccgaactaat cagtgccgga gaaacagggc aatttgatgt    540
cgttatcatt gcttctaaag catactcgct tggtcaagtg atagaggatg tcaaaccatt    600
tatccatcaa gaatctgtca ttatccctttt tttaaatggg taccgccact atgagcagct    660
atttgcggca ttttcaaaag aacaggtgct gggcggcctg tgttttatag aaagtgcttt    720
agacaacaaa ggagaaattc atcatacgag cgcatcgcat cgttttgtat ttggagaatg    780
gaacggcgag cgtacggagc ggataagagc gcttgaagag gcattttcag gtgtgaaggc    840
tgaagtcatc attagcgggc atatcgagaa ggacatttgg aaaaagtatc tctttattgc    900
agcgcaagcg gggatcacaa cgttatttca acgaccgctt ggcccaatcc tcgccacaga    960
agccggacgt cacacggccc aaactcttat tggggaaatt tgcactgttt tacgaaagaa   1020
aggtgttccg gctgatccgg ctcttgagga agagagcttt cgtacgatga ccagcatgtc   1080
ttaccatatg aagtcctcca tgcttcggga tatggaaaac ggccaaacga cagaaggcga   1140
ccacctgcat ggattttga ttgaaaaagc aaaacgttta tctctcgctg caccagtatt   1200
agaaaccgtt tatgcgaatc tgcaaatgta tgaagcagaa aaataaaaaa aggaggcgga   1260
aaagcctcct tttatttact taaaaagccc aatttccgtt tctgaagata ggctctcttt   1320
tcccgtctgc cgggatcctg ttttggcgga tgagagaaga ttttcagcct gatacagatt   1380
aaatcagaac gcagaagcgg tctgataaaa cagaatttgc ctggcggcag tagcgcggtg   1440
gtcccacctg accccatgcc gaactcagaa gtgaaacgcc gtagcgccga tggtagtgtg   1500
gggtctcccc atgcgagagt agggaactgc caggcatcaa ataaaacgaa aggctcagtc   1560
gaaagactgg gcctttcgtt ttatctgttg tttgtcggtg aacgctctcc tgagtaggac   1620 aaaatccgccg ggagcggatt tgaacgttgc gaagcaacgg cccggagggt ggcgggcagg   1680
acgcccgcca taaactgcca ggcatcaaat taagcagaag gccatcctga cggatggcct   1740
ttttgcgttt ctacaaactc ttggtaccca gaaaaagcgg caaaagcggc tgttaaaaaa   1800
gcgaaatcga agaagctgtc tgccgctaag acggaatatc aaaagcgttc tgctgttgtg   1860
tcatctttaa aagtcacagc cgatgaatcc cagcaagatg tcctaaaata cttgaacacc   1920
cagaaagata aggaaatgc agaccaaatt cattcttatt atgtggtgaa cgggattgct   1980
gttcatgcct caaagagagt tatggaaaaa gtggtgcagt ttcccgaagt ggaaaaggtg   2040
cttcctaatg agaaacggca gcttttttaag tcatcctccc catttaatat gaaaaaagca   2100
cagaaagcta ttaaagcaac tgacggtgtg aatggaatg tagaccaaat cgatgcccca   2160
aaagcttggg cacttggata tgatggaact ggcacggttg ttgcgtccat tgataccggg   2220
gtggaatgga atcatccggc attaaaagag aaatatcgcg gatataatcc ggaaaatcct   2280
aatgagcctg aaaatgaaat gaactggtat gatgccgtag caggcgaggc aagcccttat   2340
gatgatttgg ctcatggaac ccacgtgaca ggcacgatgg tgggctctga acctgatgga   2400
acaaatcaaa tcggtgtagc acctggcgca aaatggattg ctgttaaagc gttctctgaa   2460
gatggcggca ctgatgctga cattttggaa gctggtgaat gggttttagc accaaaggac   2520
gcggaaggaa atccccaccc ggaaatggct cctgatgttg tcaataactc atggggaggg   2580
ggctctggac ttgatgaatg gtacagagac atggtcaatg cctggcgttc ggccgatatt   2640
ttccctgagt tttcagcggg gaatacggat ctctttattc ccggcgggcc tggttctatc   2700
gcaaatccgg caaactatcc agaatcgttt gcaactggag cgactgagaa ttccaattcc   2760
ccatggagag aaaagaaaat cgctaatgtt gattactttg aacttctgca tattcttgaa   2820
```

-continued

```
tttaaaaagg ctgaaagagt aaaagattgt gctgaaatat tagagtataa acaaaatcgt    2880
gaaacaggcg aaagaaagtt gtatcgagtg tggttttgta aatccaggct ttgtccaatg    2940
tgcaactgga ggagagcaat gaaacatggc attcagtcac aaaaggttgt tgctgaagtt    3000
attaaacaaa agccaacagt tcgttggttg tttctcacat taacagttaa aaatgtttat    3060
gatggcgaag aattaaataa gagtttgtca gatatggctc aaggatttcg ccgaatgatg    3120
caatataaaa aaattaataa aaatcttgtt ggttttatgc gtgcaacgga agtgacaata    3180
aataataaag ataattctta taatcagcac atgcatgtat tggtatgtgt ggaaccaact    3240
tattttaaga atacagaaaa ctacgtgaat caaaaacaat ggattcaatt ttggaaaaag    3300
gcaatgaaat tagactatga tccaaatgta aaagttcaaa tgattcgacc gaaaaataaa    3360
tataaatcgg atatacaatc ggcaattgac gaaactgcaa aatatcctgt aaaggatacg    3420
gattttatga ccgatgatga agaaaagaat ttgaaacgtt tgtctgattt ggaggaaggt    3480
ttacaccgta aaaggttaat ctcctatggt ggtttgttaa agaaaataca taaaaaatta    3540
aaccttgatg cacacagaaga aggcgatttg attcatacag atgatgacga aaaagccgat    3600
gaagatggat tttctattat tgcaatgtgg aattgggaac ggaaaaatta ttttattaaa    3660
gagtagttca acaaacgggc catattgttg tataagtgat gaaatactga atttaaaact    3720
tagtttatat gtggtaaaat gttttaatca agtttaggag gaattaatta tgaagtgtaa    3780
tgaatgtaac agggttcaat taaaagaggg aagcgtatca ttaaccctat aaactacgtc    3840
tgccctcatt attggagggt gaaatgtgaa tacatcctat tcacaatcga atttacgaca    3900
caaccaaatt ttaatttggc tttgcatttt atctttttttt agcgtattaa atgaaatggt    3960
tttgaacgtc tcattacctg atattgcaaa tgattttaat aaaccacctg cgagtacaaa    4020
ctgggtgaac acagcctttta tgttaaccct ttccattgga acagctgtat atggaaagct    4080
atctgatcaa ttaggcatca aaaggttact cctatttgga attataataa attgtttcgg    4140
gtcggtaatt gggtttgttg gccattcttt cttttcctta cttattatgg ctcgttttat    4200
tcaaggggct ggtgcagctg catttccagc actcgtaatg gttgtagttg cgcgctatat    4260
tccaaaggaa aatagggggta aagcatttgg tcttattgga tcgatagtag ccatgggaga    4320
aggagtcggt ccagcgattg gtggaatgat agcccattat attcattggt cctatcttct    4380
actcattcct atgataacaa ttatcactgt tccgtttctt atgaaattat taaagaaaga    4440
agtaaggata aaaggtcatt ttgatatcaa aggaattata ctaatgtctg taggcattgt    4500 atttttttatg ttgtttacaa catcatatag catttctttt cttatcgtta gcgtgctgtc    4560
attcctgata tttgtaaaac atatcaggaa agtaacagat cctttgttg atcccggatt    4620 agggaaaaat ataccttta tgattggagt tctttgtggg ggaattatat ttggaacagt    4680
agcagggttt gtctctatgg ttccttatat gatgaaagat gttcaccagc taagtactgc    4740
cgaaatcgga agtgtaatta ttttcccctgg aacaatgagt gtcattattt tcggctacat    4800
tggtgggata cttgttgata gaagaggtcc tttatacgtg ttaaacatcg gagttacatt    4860
tctttctgtt agcttttttaa ctgcttcctt tcttttagaa acaacatcat ggttcatgac    4920
aattataatc gtatttgttt taggtgggct ttcgttcacc aaaacagtta tcaacaat    4980 tgtttcaagt agcttgaaac agcaggaagc tggtgctgga atgagtttgc ttaactttac    5040
cagcttttta tcagagggaa caggtattgc aattgtaggt ggtttattat ccatacccctt    5100 acttgatcaa aggttgttac ctatggaagt tgatcagtca acttatctgt atagtaattt    5160
gttattactt ttttcaggaa tcattgtcat tagttggctg gttaccttga atgtatataa    5220
```

```
acattctcaa agggatttct aaatcgttaa gggatcaact ttgggagaga gttcaaaatt    5280
gatccttttt ttataacagt tcgaagcggc cgcaattctt gaagacgaaa gggcctcgtg    5340
atacgcctat ttttataggt taatgtcatg ataataatgg tttcttagac gtcaggtggc    5400
acttttcggg gaaatgtgcg cggaacccct atttgtttat ttttctaaat acattcaaat    5460
atgtatccgc tcatgagaca ataaccctga taaatgcttc aataatattg aaaaggaag    5520
agtatgagta ttcaacattt ccgtgtcgcc cttattccct tttttgcggc attttgcctt    5580
cctgttttg ctcacccaga aacgctggtg aaagtaaaag atgctgaaga tcagttgggt    5640
gcacgagtgg gttacatcga actggatctc aacagcggta agatccttga gagttttcgc    5700
cccgaagaac gttttccaat gatgagcact tttaaagttc tgctatgtgg cgcggtatta    5760
tcccgtattg acgccgggca agagcaactc ggtcgccgca tacactattc tcagaatgac    5820
ttggttgagt actcaccagt cacagaaaag catcttacgg atggcatgac agtaagagaa    5880
ttatgcagtg ctgccataac catgagtgat aacactgcgg ccaacttact tctgacaacg    5940
atcggaggac cgaaggagct aaccgctttt ttgcacaaca tgggggatca tgtaactcgc    6000
cttgatcgtt gggaaccgga gctgaatgaa gccataccaa acgacgagcg tgacaccacg    6060
atgcctgcag caatggcaac aacgttgcgc aaactattaa ctggcgaact acttactcta    6120
gcttcccggc aacaattaat agactggatg gaggcggata agttgcagg accacttctg    6180
cgctcggccc ttccggctgg ctggtttatt gctgataaat ctggagccgg tgagcgtggg    6240
tctcgcggta tcattgcagc actggggcca gatggtaagc cctcccgtat cgtagttatc    6300
tacacgacgg ggagtcaggc aactatggat gaacgaaata gacagatcgc tgagataggt    6360
gcctcactga ttaagcattg gtaactgtca gaccaagttt actcatatat actttagatt    6420
gatttaaaac ttcatttta atttaaaagg atctaggtga agatccttt tgataatctc    6480
atgaccaaaa tcccttaacg tgagttttcg ttccactgag cgtcagaccc cgtagaaaag    6540
atcaaaggat cttcttgaga tccttttttt ctgcgcgtaa tctgctgctt gcaaacaaaa    6600
aaaccaccgc taccagcggt ggtttgtttg ccggatcaag agctaccaac tcttttccg    6660
aaggtaactg gcttcagcag agcgcagata ccaaatactg tccttctagt gtagccgtag    6720
ttaggccacc acttcaagaa ctctgtagca ccgcctacat acctcgctct gctaatcctg    6780
ttaccagtgg ctgctgccag tggcgataag tcgtgtctta ccgggttgga ctcaagacga    6840
tagttaccgg ataaggcgca gcggtcgggc tgaacggggg gttcgtgcac acagcccagc    6900
ttggagcgaa cgacctacac cgaactgaga tacctacagc gtgagctatg agaaagcgcc    6960
acgcttcccg aagggagaaa ggcggacagg tatccggtaa gcggcagggt cggaacagga    7020
gagcgcacga gggagcttcc agggggaaac gcctggtatc tttatagtcc tgtcgggttt    7080
cgccacctct gacttgagcg tcgatttttg tgatgctcgt caggggggcg gagcctatgg    7140
aaaaacgcca gcaacgcggc ctttttacgg ttcctggcct tttgctggcc ttttgctcac    7200
atgttctttc ctgcgttatc ccctgattct gtggataacc gtattaccgc ctttgagtga    7260
gctgataccg ctcgccgcag ccgaacgacc gagcgcagcg agtcagtgag cgaggaagcg    7320
gaagagcgcc tgatgcggta ttttctcctt acgcatctgt gcggtatttc acaccgcata    7380
tggtgcactc tcagtacaat ctgctctgat gccgcatagt taagccagta tacactccgc    7440
tatcgctacg tgactgggtc atggctgcgc cccgacaccc gccaacaccc gctgacgcgc    7500
cctgacgggc ttgtctgctc ccggcatccg cttacagaca agctgtgacc gtctccggga    7560
```

```
gctgcatgtg tcagaggttt tcaccgtcat caccgaaacg cgcgaggcag ctgcggtaaa    7620
gctcatcagc gtggtcgtga agcgattcac agatgtctgc ctgttcatcc gcgtccagct    7680
cgttgagttt ctccagaagc gttaatgtct ggcttctgat aaagcgggcc atgttaaggg    7740
cggttttttc ctgtttggtc acttgatgcc tccgtgtaag ggggaatttc tgttcatggg    7800
ggtaatgata ccgatgaaac gagagaggat gctcacgata cgggttactg atgatgaaca    7860
tgcccggtta ctggaacgtt gtgagggtaa acaactggcg gtatgatgc ggcgggacca     7920 gagaaaaatc actcagggtc aatgccagcg cttcgttaat acagatgtag gtgttccaca    7980
gggtagccag cagcatcctg cgatgcagat ccggaacata atggtgcagg cgctgactt     8040 ccgcgtttcc agactttacg aaacacggaa accgaagacc attcatgttg ttgctcaggt    8100
cgcagacgtt ttgcagcagc agtcgcttca cgttcgctcg cgtatcggtg attcattctg    8160
ctaaccagta aggcaacccc gccagcctag ccgggtcctc aacgacagga gcacgatcat    8220
gcgcacccgt ggccaggacc caacgctgcc cgagatgcgc cgcgtgcggc tgctggagat    8280
ggcggacgcg atggatatgt tctgccaagg gttggtttgc gcattcacag ttctccgcaa    8340
gaattgattg gctccaattc ttggagtggt gaatccgtta gcgaggtgcc gccggcttcc    8400
attcaggtcg aggtggcccg gctccatgca ccgcgacgca acgcggggag gcagacaagg    8460
tatagggcgg cgcctacaat ccatgccaac ccgttccatg tgctcgccga ggcggcataa    8520
atcgccgtga cgatcagcgg tccagtgatc gaagttaggc tggtaagagc cgcgagcgat    8580
ccttgaagct gtccctgatg gtcgtcatct acctgcctgg acagcatggc ctgcaacgcg    8640
ggcatcccga tgccgccgga agcgagaaga atcataatgg ggaaggccat ccagcctcgc    8700
gtcg                                                                 8704

<210> SEQ ID NO 26
<211> LENGTH: 6688
<212> TYPE: DNA
<213> ORGANISM: Artificial Sequence
<220> FEATURE:
<223> OTHER INFORMATION: Description of Artificial Sequence: vector
<220> FEATURE:
<223> OTHER INFORMATION: pAN336

<400> SEQUENCE: 26
tgcgccgcta cagggcgcgt ccattcgcca ttcaggctgc gcaactgttg ggaagggcga     60
tcggtgcggg cctcttcgct attacgccag ctggcgaaag ggggatgtgc tgcaaggcga    120
ttaagttggg taacgccagg gttttcccag tcacgacgtt gtaaaacgac ggccagtgaa    180
ttgtaatacg actcactata gggcgaattg ggcccgacgt cgcatgcacc aggcttctca    240
ggcgctgact tagaaaacct cttgaatgaa gctgcgcttg tagcggctcg tcaaaacaag    300
aaaaaaatcg atgcgcgtga tattgacgaa gcgacggacc gtgtaattgc cggacccgct    360
aagaagagcc gcgttatctc caagaaagaa cgcaatatcg tggcttatca cgaaggcgga    420
cacaccgtta tcggtctcgt tttagatgag gcagatatgg ttcataaagt aacgattgtt    480
cctcggggcc aggctggcgg ttatgctgtt atgctgccaa gagaagaccg ttatttccaa    540
acaaagccgg agctgcttga taaaattgtc ggcctcttgg gcggacgtgt tgctgaagag    600
attatcttcg gtgaagtcag cacagggggcg cacaatgact ccagcgtgc gacgaatatt    660 gcaagacgaa tggttacaga attcggtatg tcagaaaaac tgggaccgtt gcaatttgga    720
cagtctcagg gcggtcaggt attcttaggc cgtgatttca acaacgaaca gaactacagt    780
gatcaaatcg cttacgaaat tgatcaggaa attcagcgca tcatcaaaga atgttatgag    840
```

```
cgtgcgaaac aaatcctgac tgaaaatcgt gacaagcttg aattgattgc ccaaacgctt      900
ctgaaagttg aaacgcttga cgctgaacaa atcaaacacc ttatcgatca tggaacatta      960
cctgagcgta atttctcaga tgatgaaaag aacgatgatg tgaaagtaaa cattctgaca     1020
aaaacagaag aaaagaaaga cgatacgaaa gagtaattcg ctttctttct aaaaaaactg     1080
ccggctgacg ctggcagttt ttttatgtaa atgattggct cagctgcggc ttttacaatc     1140
atccaattct ggtatcgatt tgtttacaaa tgagccgctg atcgtgtatg gtattgtaga     1200
atgtttgtaa aaagtaaagt agagaaacta ttcaaaagtg gtgatagagg ttgttactgg     1260
ttatcgatgt ggggaacacc ctgcagctcg agtgaaatac cgcacagatg cgtaaggaga     1320
aaataccgca tcaggcgata aacccagcga accatttgag gtgataggta agattatacc     1380
gaggtatgaa acgagaatt ggacctttac agaattactc tatgaagcgc catatttaaa      1440
aagctaccaa gacgaagagg atgaagagga tgaggaggca gattgccttg aatatattga     1500
caatactgat aagataatat atcttttata tagaagatat cgccgtatgt aaggatttca     1560
gggggcaagg cataggcagc gcgcttatca atatatctat agaatgggca aagcataaaa     1620
acttgcatgg actaatgctt gaaacccagg acaataacct tatagcttgt aaattctatc     1680
ataattgtgg tttcaaaatc ggctccgtcg atactatgtt atacgccaac tttcaaaaca     1740
actttgaaaa agctgttttc tggtatttaa ggttttagaa tgcaaggaac agtgaattgg     1800
agttcgtctt gttataatta gcttcttggg gtatctttaa atactgtaga aaagaggaag     1860
gaaataataa atggctaaaa tgagaatatc accggaattg aaaaaactga tcgaaaaata     1920
ccgctgcgta aaagatacgg aaggaatgtc tcctgctaag gtatataagc tggtgggaga     1980
aaatgaaaac ctatatttaa aaatgacgga cagccggtat aaagggacca cctatgatgt     2040
ggaacgggaa aaggacatga tgctatggct ggaaggaaag ctgcctgttc caaaggtcct     2100
gcactttgaa cggcatgatg gctggagcaa tctgctcatg agtgaggccg atggcgtcct     2160
ttgctcggaa gagtatgaag atgaacaaag ccctgaaaag attatcgagc tgtatgcgga     2220
gtgcatcagg ctcttttcact ccatcgacat atcggattgt ccctatacga atagcttaga     2280
cagccgctta gccgaattgg attacttact gaataacgat ctggccgatg tggattgcga     2340
aaactgggaa gaagacactc catttaaaga tccgcgcgag ctgtatgatt ttttaaagac     2400
ggaaaagccc gaagaggaac ttgtcttttc ccacggcgac ctgggagaca gcaacatctt     2460
tgtgaaagat ggcaaagtaa gtggctttat tgatcttggg agaagcggca gggcggacaa     2520
gtggtatgac attgccttct gcgtccggtc gatcaggag gatatcgggg aagaacagta      2580
tgtcgagcta ttttttgact tactggggat caagcctgat tgggagaaaa taaaatatta     2640
tattttactg gatgaattgt tttagtacct agatttagat gtctaaaaag ctttaactac     2700
aagctttta gacatctaat cttttctgaa gtacatccgc aactgtccat actctgatgt      2760
tttatatctt ttctaaaagt tcgctagata ggggtcccga gcgcctacga ggaatttgta     2820
tcgccattcg ccattcaggc tgcgcaactg ttgggaaggg cgatcggtgc ggtcgactgg     2880
caggcaaaac aggacccaag gtcattgcga caggaggcct ggcgccgctc attgcgaacg     2940
aatcagattg tatagacatc gttgatccat tcttaaccct aaaagggctg aattgatttt     3000
atgaaagaaa ccgcgtagga agtgtatagg aggtttagta atggattatt tagtaaaagc     3060
acttgcgtat gacggaaaag ttcgggctta tgcagcgaga acgactgata tggtaaatga     3120
ggggcagaga cgccatggta cgtggccgac agcatccgct gcactaggcc gtacaatgac     3180
```

```
agcttcactt atgctcggcg ctatgctgaa gggcgatgat aagctgaccg tgaaaatcga   3240
gggcggaggt ccgatcggag ctattgtagc tgatgccaat gccaaaggag aagtcagagc   3300
ctatgtctct aacccgcaag ttcattttga tttaaatgaa caaggtaagc ttgatgtcag   3360
acgtgcggtt ggaacaaacg gaacgttaag tgtcgtaaaa gatttaggtt tgcgcgagtt   3420
cttcacagga caagtagaaa tcgtttcagg agaattagga gatgatttta cttactatct   3480
tgtgtcatct gagcaggttc cttcatcagt gggcgtaggt gtgctcgtaa atcctgacaa   3540
taccattctt gcggcagggg gctttattat tcagctgatg ccgggaacag atgatgaaac   3600
aatcacaaaa attgaacagc gtctatctca agtagagccg atttctaagc tcatccaaaa   3660
agggctgaca ccagaagaaa ttttagaaga agtcctaggc gagaaacctg agattttgga   3720
aacgatgcct gtcagattcc attgcccttg ttcaaaagaa cggttcgaaa cagccatttt   3780
aggactaggc aaaaaagaaa ttcaagatat gatagaagaa gatggacaag ccgaagcagt   3840
atgccatttt tgtaatgaaa agtacttatt tacaaaagaa gagctggaag gcttcgtgaa   3900
ccaaactacc cgctaagctc tttagcgggt ttttaatttg agaaaagggg ctgaaagcag   3960
gtttgaaatc aagaacaatc tggacgcgtt ggatgcatag cttgagtatt ctatagtgtc   4020
acctaaatag cttggcgtaa tcatggtcat agctgtttcc tgtgtgaaat tgttatccgc   4080
tcacaattcc acacaacata cgagccggaa gcataaagtg taaagcctgg ggtgcctaat   4140
gagtgagcta actcacatta attgcgttgc gctcactgcc cgctttccag tcgggaaacc   4200
tgtcgtgcca gctgcattaa tgaatcggcc aacgcgcggg gagaggcggt ttgcgtattg   4260
ggcgctcttc cgcttcctcg ctcactgact cgctgcgctc ggtcgttcgg ctgcggcgag   4320
cggtatcagc tcactcaaag gcggtaatac ggttatccac agaatcaggg gataacgcag   4380
gaaagaacat gtgagcaaaa ggccagcaaa aggccaggaa ccgtaaaaag gccgcgttgc   4440
tggcgttttt cgataggctc cgcccccctg acgagcatca caaaaatcga cgctcaagtc   4500
agaggtggcg aaacccgaca ggactataaa gataccaggc gtttccccct ggaagctccc   4560
tcgtgcgctc tcctgttccg accctgccgc ttaccggata cctgtccgcc tttctccctt   4620
cgggaagcgt ggcgctttct catagctcac gctgtaggta tctcagttcg gtgtaggtcg   4680
ttcgctccaa gctgggctgt gtgcacgaac cccccgttca gcccgaccgc tgcgccttat   4740
ccggtaacta tcgtcttgag tccaacccgg taagacacga cttatcgcca ctggcagcag   4800
ccactggtaa caggattagc agagcgaggt atgtaggcgg tgctacagag ttcttgaagt   4860
ggtggcctaa ctacggctac actagaagga cagtatttgg tatctgcgct ctgctgaagc   4920
cagttacctt cggaaaaaga gttggtagct cttgatccgg caaacaaacc accgctggta   4980
gcggtggttt ttttgtttgc aagcagcaga ttacgcgcag aaaaaaagga tctcaagaag   5040
atcctttgat cttttctacg gggtctgacg ctcagtggaa cgaaaactca cgttaaggga   5100
ttttggtcat gagattatca aaaaggatct tcacctagat ccttttaaat taaaaatgaa   5160
gttttaaatc aatctaaagt atatatgagt aaacttggtc tgacagttac caatgcttaa   5220
tcagtgaggc acctatctca gcgatctgtc tatttcgttc atccatagtt gcctgactcc   5280
ccgtcgtgta gataactacg atacgggagg gcttaccatc tggccccagt gctgcaatga   5340
taccgcgaga cccacgctca ccggctccag atttatcagc aataaaccag ccagccggaa   5400
gggccgagcg cagaagtggt cctgcaactt tatccgcctc catccagtct attaattgtt   5460
gccgggaagc tagagtaagt agttcgccag ttaatagttt cgcaacgtt gttggcattg   5520 ctacaggcat cgtggtgtca cgctcgtcgt ttggtatggc ttcattcagc tccggttccc   5580
```

```
aacgatcaag gcgagttaca tgatccccca tgttgtgcaa aaaagcggtt agctccttcg    5640
gtcctccgat cgttgtcaga agtaagttgg ccgcagtgtt atcactcatg gttatggcag    5700
cactgcataa ttctcttact gtcatgccat ccgtaagatg cttttctgtg actggtgagt    5760
actcaaccaa gtcattctga gaataccgcg cccggcgacc gagttgctct tgcccggcgt    5820
caatacggga taatagtgta tgacatagca gaactttaaa agtgctcatc attggaaaac    5880
gttcttcggg gcgaaaactc tcaaggatct taccgctgtt gagatccagt tcgatgtaac    5940
ccactcgtgc acccaactga tcttcagcat cttttacttt caccagcgtt tctgggtgag    6000
caaaaacagg aaggcaaaat gccgcaaaaa agggaataag ggcgacacgg aaatgttgaa    6060
tactcatact cttcctttttc aatattatt gaagcattta tcagggttat tgtctcatga    6120
gcggatacat atttgaatgt atttagaaaa ataaacaaat aggggttccg cgcacatttc    6180
cccgaaaagt gccacctgta tgcggtgtga ataccgcac agatgcgtaa ggagaaaata    6240
ccgcatcagg cgaaattgta aacgttaata ttttgttaaa attcgcgtta aatatttgtt    6300
aaatcagctc atttttttaac caataggccg aaatcggcaa aatcccttat aaatcaaaag    6360
aatagaccga gatagggttg agtgttgttc cagtttggaa caagagtcca ctattaaaga    6420
acgtggactc caacgtcaaa gggcgaaaaa ccgtctatca gggcgatggc ccactacgtg    6480
aaccatcacc caaatcaagt ttttttgcggt cgaggtgccg taaagctcta atcggaacc    6540 ctaaagggag cccccgattt agagcttgac ggggaaagcc ggcgaacgtg gcgagaaagg    6600
aagggaagaa agcgaaagga gcgggcgcta gggcgctggc aagtgtagcg gtcacgctgc    6660
gcgtaaccac cacacccgcc gcgcttaa                                       6688

<210> SEQ ID NO 27
<211> LENGTH: 8803
<212> TYPE: DNA
<213> ORGANISM: Artificial Sequence
<220> FEATURE:
<223> OTHER INFORMATION: Description of Artificial Sequence: vector
<220> FEATURE:
<223> OTHER INFORMATION: pAN294

<400> SEQUENCE: 27
tgcgccgcta cagggcgcgt ccattcgcca ttcaggctgc gcaactgttg ggaagggcga      60
tcggtgcggg cctcttcgct attacgccag ctggcgaaag ggggatgtgc tgcaaggcga     120
ttaagttggg taacgccagg gttttcccag tcacgacgtt gtaaaacgac ggccagtgaa     180
ttgtaatacg actcactata gggcgaattg ggcccgacgt cgcatgctgg atgaaaagcc     240
gatgaccgct tttcaggtct gtcagcagct ttttcctgct gtatatgaaa aggaattgtt     300
tttaacgatg tcagaaacgg caggtcacct tgatgtgttg gaggctgaag aagccatcac     360
gtcatattgg gaaggaaata ccgtatactt taaaacaatg aagaggtgaa atgggtgaaa     420
catatagcgg gaaaaaggat ttggataacc ggcgcttcag gagggcttgg agaaagaatc     480
gcatacttat gcgcggctga aggagcccat gtcctgctgt cggctagacg cgaggatcgt     540
ttgatagaaa tcaaaaggaa aataaccgag gaatggagcg gacagtgtga gattttcct     600 ctggatgtcg gccgcctaga ggatatcgcc cgggtccgcg atcagatcgg ctcgattgat     660
gtactgatta acaatgcagg cttcggtata tttgaaacgg ttttagactc tacattggat     720
gacatgaaag cgatgtttga tgtgaatgtc ttcggcctga tcgcctgtac aaaagcggtg     780
cttccgcaaa tgcttgagca aaaaaaggga catatcatca atatcgcctc tcaagcgggg     840
```

```
aaaatcgcca caccgaagtc tagcctgtat tccgcgacca acatgccgt gttaggttac      900 tcaaacgctt tgcggatgga gctttcggga accggcattt atgtgacaac agtcaacccg      960
ggcccgattc agacggactt tttttccatt gctgataaag gcggggacta cgccaaaaat     1020
gtcggccgct ggatgcttga tcctgatgac gtggcagctc aaattacagc tgcaattttt     1080
acgaaaaagc gggagatcaa tcttccgcgt ttaatgaatg ccggcactaa gctgtatcag     1140
ctgtttccag ctcttgtaga aaagctggca ggacgcgcgc tcatgaaaaa ataatgatag     1200
aactgcctgt ggtggagtgg cttgtttctc acggggcagt ttttgatagt ggaagggaga     1260
gattgttgaa tgtcagttca ttcagaagtc cttcatgctc tgcttaaaga tccgtttatt     1320
cagaaactga ttgatgcaga gcctgtattc tgggcaaatt caggcaagaa agagggccca     1380
ttaccccgtg cagatgagtg ggcaaccgag atagcggaag cggaaaaaag aatgcagcgg     1440
tttgcacctt acattgccga ggtgtttcct gagacgaaag gcgctaaagg aatcatcgag     1500
tctccgcttt tgaggtgca gcatatgaag ggaaagctgg aagcggcata tcagcagcca     1560
tttcccggaa gatggctttt aaagtgcgac catgagcttc cgatttcagg atcgattaaa     1620
gcgaggggcg ggatttatga agtgttaaag tatgctgaaa atctcgcgct tcaagaagga     1680
atgcttcagg aaaccgatga ttaccgcatc ttacaggaag agcggtttac cgggttttc     1740 tcccgctatt cgattgctgt cggttcgaca ggaaatctag gtttaagcat cggcatcatc     1800
ggcgcggcac tcgggtttcg cgtgacagtg catatgtccg ccgatgctaa gcagtggaaa     1860
aaggatctcc tccgccaaaa gggagtcact gttatggagt acgaaacaga ttacagtgaa     1920
gcggtgaacg aagggagacg gcaggcggaa caagatccat tctgttattt tattgatgat     1980
gaacattctc gtcagctgtt cttaggatat gctgttgctg caagccgatt aaaaacacag     2040
cttgactgta tgaatataaa gccaagtctt gagacgcct tgtttgtgta tctgccgtgc     2100
ggagtcggcg gaggaccggg cggtgtagca tttgggctga agcttttata cggagatgat     2160
gttcatgtgt ttttcgcaga accaactcat tcaccttgta tgctgttagg gctttattca     2220
ggacttcacg agaagatctc cgtccaggat atcggcctgg ataatcagac ggctgctgac     2280
ggacttgccg taggaggcc gtcaggattt gtcggcaagc tgattgaacc gcttctgagc     2340
ggctgttata cggtagagga caatacgctt tatactttgc ttcatatgct ggctgtatct     2400
gaagataaat atttagagcc ctctgctctt gctggcatgt tcgggccggt tcagcttttt     2460
tcgacagaag agggaaggcg ctatgctcag aaatataaga tggaacatgc cgtacatgtc     2520
gtctggggaa cgggaggaag catggttcca aaagatgaaa tggctgcgta taccgaatc     2580 ggtgctgatt tgctaaaaaa acgaaatgga aaataagcag acagtgaaaa ggttttccgt     2640
tacaatcttt gtaagggttt taacctacag agagtcaggt gtaaacagtg aaaaataaag     2700
aacttaacct acatacttta tatacacagc acaatcggga gtcttggtct ggttttgggg     2760
ggcatttgtc gattgctgta tctgaagaag aggcaaaagc tgtggaagga ttgaatgatt     2820
atctatctgt tgaagaagtg gagacgatct atattccgct tgttcgcttg cttcatttac     2880
atgtcaagtc tgcggctgaa cgcaataagc atgtcaatgt tttttttgaag cacccacatt     2940 cagccaaaat tccgtttatt atcggcattg ccggcagtgt cgcagtcgga aaaagcacga     3000
cggcgcggat cttgcagaag ctgctttcgc gtttgcctga ccgtccaaaa gtgagcctta     3060
tcacgacaga tggttttta tttcctactg ccgagctgaa aaagaaaaat atgatgtcaa     3120
gaaaaggatt tcctgaaagc tatgatgtaa aggcgctgct cgaattttg aatgacttaa     3180 aatcaggaaa ggacagcgta aaggccccgg tgtattccca tctaacctat gaccgcgagg     3240
```

```
aaggtgtgtt cgaggttgta gaacaggcgg atattgtgat tattgaaggc attaatgttc    3300
ttcagtcgcc caccttggag gatgaccggg aaaacccgcg tattttttgtt tccgatttct    3360 ttgattttc  gatttatgtg gatgcggagg aaagccggat tttcacttgg tatttagagc    3420
gttttcgcct gcttcgggaa acagcttttc aaaatcctga ttcatatttt cataaattta    3480
aagacttgtc cgatcaggag gctgacgaga tggcagcctc gatttgggag agtgtcaacc    3540
ggccgaattt atatgaaaat attttgccaa ctaaattcag gtcagatctc attttgcgta    3600
agggagacgg gcataaggtc gaggaagtgt tggtaaggag ggtatgaaat gtgctgcagc    3660
tcgagcaata gttacccttta ttatcaagat aagaaagaaa aggattttc  gctacgctca    3720 aatcctttaa aaaacacaa  aagaccacat tttttaatgt ggtctttatt cttcaactaa    3780
agcacccatt agttcaacaa acgaaaattg gataaagtgg gatattttta aaatatatat    3840
ttatgttaca gtaatattga cttttaaaaa aggattgatt ctaatgaaga aagcagacaa    3900
gtaagcctcc taaattcact ttagataaaa atttaggagg catatcaaat gaactttaat    3960
aaaattgatt tagacaattg gaagagaaaa gagatattta atcattattt gaaccaacaa    4020
acgactttta gtataaccac agaaattgat attagtgttt tataccgaaa cataaaacaa    4080
gaaggatata aattttaccc tgcatttatt ttcttagtga caagggtgat aaactcaaat    4140 acagcttta  gaactggtta caatagcgac ggagagttag gttattggga taagttagag    4200
ccactttata caattttga  tggtgtatct aaaacattct ctggtatttg gactcctgta    4260
aagaatgact tcaaagagtt ttatgattta tacctttctg atgtagagaa atataatggt    4320
tcggggaaat tgtttcccaa aacacctata cctgaaaatg cttttttctct ttctattatt    4380 ccatggactt catttactgg gtttaactta aatatcaata ataatagtaa ttaccttcta    4440
cccattatta cagcaggaaa attcattaat aaaggtaatt caatatattt accgctatct    4500
ttacaggtac atcattctgt ttgtgatggt tatcatgcag gattgtttat gaactctatt    4560
caggaattgt cagataggcc taatgactgg ctttttataat atgagataat gccgactgta    4620 cttttttacag tcggttttct aatgtcacta acctgccccg ttagttgaag aaggttttta    4680
tattacagct gtcgactcgt gatcttcgga caggctgttc agcttttttct caatgcgatc    4740 cagctgcgct tttcggtttt tcgcatactt gaagcctgta acagccgcaa agacgacagc    4800
ggcaaatata ataaatacaa acagctgaaa catcacatca cctatattca tgttcttcac    4860
ctcatgtttg cgggagagat tcattctctt ccgtttttta tttaaagcgg cttttccaga    4920
cgggaacggt gttttgtggt ctccatttc  atttgccgat aggcgaacgc taaaaatggc    4980
aggccgagca gggtaatgcc gctcaggaca gaaaaaatat aaatcggccg gccagcgcca    5040
aacaggtcta tacatatccc cccgacccaa gggccgatga cgtttccgag ctgtggaaaa    5100
ccgattgccc cgaaataagt gccttttaat cctggttttg caatctggtc tacatacaaa    5160
tccatcatag agaataaaag cacttcgccg attgtaaatg tgatgacaat catcacaatt    5220
gatggaacac cgtgtgatac ggtgaaaatg gccatgctga tgctaaccat cacattaccg    5280
agcatcagag aacaaagcgg cgaaaaccgt tttgcaaaat ggacaatggg aaattgcgtc    5340
gccaacacaa cgattgcgtt taatgtcagc atcagcccat acagcttcgt tccattgccg    5400 atcaagggt  tctgcgccat atactgaggg aatgtggaac tgaattgtga gtagccgaag    5460
gtgcatagcg taatgccgac caaagcaatg gtaaaaagat aatccttttg cgtgaccata    5520
aacgcttccc gcacgctcat atttcgggac tgggctggtg ctgataagga tggatgtttt    5580
```

-continued

```
ttaaattgga gggcaagcac aattccgtat agtccgtaaa tgactgcagg caccaaaaag    5640
ggcgtagtcg attgcgatga gccgaaatat aggccaagca caggtccgaa gacaacgccg    5700
atattaatag ccgcatagcg taaattaaaa actagcagtc tcgttttttc ttctgtcata    5760
tcagacaaca aggcctttga agcgggctca acagtgatt tgcaaagacc gtttaatgcg     5820
tttactacaa aaaacaccca gagattagat gctgccgcaa agcctgcaaa taccagcatc    5880
catccgaaaa tcgatacaag catcatgttt tttctgccga atttatctga gatatatccg    5940
ccgtaaaagc ttgcgaggat gccgactgat gagctcgcgg cgatgaccag ccctgcatag    6000
gaagctgatg cgccttggac ggctgtcaaa taaatcgcta aaaaggaat gctcatcgat     6060
gttgccattc tgccgaaaat ggttccgatt ataattgtac gcgttggatg catagcttga    6120
gtattctata gtgtcaccta aatagcttgg cgtaatcatg gtcatagctg tttcctgtgt    6180
gaaattgtta tccgctcaca attccacaca acatacgagc cggaagcata aagtgtaaag    6240
cctggggtgc ctaatgagtg agctaactca cattaattgc gttgcgctca ctgcccgctt    6300
tccagtcggg aaacctgtcg tgccagctgc attaatgaat cggccaacgc gcggggagag    6360
gcggtttgcg tattgggcgc tcttccgctt cctcgctcac tgactcgctg cgctcggtcg    6420
ttcggctgcg gcgagcggta tcagctcact caaaggcggt aatacggtta ccacagaat     6480
caggggataa cgcaggaaag aacatgtgag caaaaggcca gcaaaaggcc aggaaccgta    6540
aaaaggccgc gttgctggcg ttttccgata ggctccgccc ccctgacgag catcacaaaa    6600
atcgacgctc aagtcagagg tggcgaaacc cgacaggact ataaagatac caggcgtttc    6660
cccctggaag ctccctcgtg cgctctcctg ttccgaccct gccgcttacc ggatacctgt    6720
ccgcctttct cccttcggga agcgtggcgc tttctcatag ctcacgctgt aggtatctca    6780
gttcggtgta ggtcgttcgc tccaagctgg gctgtgtgca cgaacccccc gttcagcccg    6840
accgctgcgc cttatccggt aactatcgtc ttgagtccaa cccggtaaga cacgacttat    6900
cgccactggc agcagccact ggtaacagga ttagcagagc gaggtatgta ggcggtgcta    6960
cagagttctt gaagtggtgg cctaactacg gctacactag aaggacagta tttggtatct    7020
gcgctctgct gaagccagtt accttcggaa aaagagttgg tagctcttga tccggcaaac    7080
aaaccaccgc tggtagcggt ggtttttttg tttgcaagca gcagattacg cgcagaaaaa    7140
aaggatctca agaagatcct ttgatctttt ctacggggtc tgacgctcag tggaacgaaa    7200
actcacgtta agggattttg gtcatgagat tatcaaaaag gatcttcacc tagatccttt    7260
taaattaaaa atgaagtttt aaatcaatct aaagtatata tgagtaaact ggtctgaca    7320
gttaccaatg cttaatcagt gaggcaccta tctcagcgat ctgtctattt cgttcatcca    7380
tagttgcctg actccccgtc gtgtagataa ctacgatacg ggagggctta ccatctggcc    7440
ccagtgctgc aatgataccg cgagacccac gctcaccggc tccagattta tcagcaataa    7500
accagccagc cggaagggcc gagcgcagaa gtggtcctgc aactttatcc gcctccatcc    7560
agtctattaa ttgttgccgg gaagctagag taagtagttc gccagttaat agtttgcgca    7620
acgttgttgg cattgctaca ggcatcgtgg tgtcacgctc gtcgtttggt atggcttcat    7680
tcagctccgg ttcccaacga tcaaggcgag ttacatgatc ccccatgttg tgcaaaaaag    7740
cggttagctc cttcggtcct ccgatcgttg tcagaagtaa gttggccgca gtgttatcac    7800
tcatggttat ggcagcactg cataattctc ttactgtcat gccatccgta agatgctttt    7860
ctgtgactgg tgagtactca accaagtcat tctgagaata ccgcgccgg cgaccgagtt     7920
gctcttgccc ggcgtcaata cgggataata gtgtatgaca tagcagaact ttaaaagtgc    7980
```

```
tcatcattgg aaaacgttct tcggggcgaa aactctcaag gatcttaccg ctgttgagat    8040
ccagttcgat gtaacccact cgtgcaccca actgatcttc agcatctttt actttcacca    8100
gcgtttctgg gtgagcaaaa acaggaaggc aaaatgccgc aaaaaaggga ataagggcga    8160
cacggaaatg ttgaatactc atactcttcc tttttcaata ttattgaagc atttatcagg    8220
gttattgtct catgagcgga tacatatttg aatgtattta gaaaaataaa caaatagggg    8280
ttccgcgcac atttccccga aaagtgccac ctgtatgcgg tgtgaaatac cgcacagatg    8340
cgtaaggaga aaataccgca tcaggcgaaa ttgtaaacgt taatattttg ttaaaattcg    8400
cgttaaatat ttgttaaatc agctcatttt ttaaccaata ggccgaaatc ggcaaaatcc    8460
cttataaatc aaaagaatag accgagatag ggttgagtgt tgttccagtt tggaacaaga    8520
gtccactatt aaagaacgtg gactccaacg tcaaagggcg aaaaaccgtc tatcagggcg    8580
atggcccact acgtgaacca tcacccaaat caagtttttt gcggtcgagg tgccgtaaag    8640
ctctaaatcg gaaccctaaa gggagccccc gatttagagc ttgacgggga aagccggcga    8700
acgtggcgag aaaggaaggg aagaaagcga aaggagcggg cgctagggcg ctggcaagtg    8760
tagcggtcac gctgcgcgta accaccacac ccgccgcgct taa                      8803
```

US 7,220,561 B2

PROCESSES FOR ENHANCED PRODUCTION OF PANTOTHENATE

RELATED APPLICATIONS

The present invetion claims the benefit of prior-filed provisional Patent Application Ser. No. 60/262,995, filed Jan. 19, 2001 (abandoned). The present invention is also related to U.S. patent application Ser. No. 09/667,569, filed Sep. 21, 2000 (pending), which is a continuation-in-part of U.S. patent application Ser. No. 09/400,494, filed Sep. 21, 1999 (abandoned). U.S. patent application Ser. No. 09/667, 569 also claims the benefit of prior-filed provisional Patent Application Ser. No. 60/210,072, filed Jun. 7, 2000, provisional Patent Application Ser. No. 60/221,836, filed Jul. 28, 2000, and provisional Patent Application Ser. No. 60/227, 860, filed Aug. 24, 2000. The entire content of each of the above-referenced applications is incorporated herein by this reference.

BACKGROUND OF THE INVENTION

Pantothenate, also known as pantothenic acid or vitamin B5, is a member of the B complex of vitamins and is a nutritional requirement for mammals, including livestock and humans (e.g., from food sources, as a water soluble vitamin supplement or as a feed additive). In cells, pantothenate is used primarily for the biosynthesis of coenzyme A (CoA) and acyl carrier protein (ACP). These coenzymes function in the metabolism of acyl moieties which form thioesters with the sulfhydryl group of the 4'-phosphopantetheine portion of these molecules. These coenzymes are essential in all cells, participating in over 100 different intermediary reactions in cellular metabolism.

The conventional means of synthesizing pantothenate (in particular, the bioactive D isomer) is via chemical synthesis from bulk chemicals, a process which is hampered by excessive substrate cost as well as the requirement for optical resolution of racemic intermediates. Accordingly, researchers have recently looked to bacterial or microbial systems that produce enzymes useful in pantothenate biosynthesis processes (as bacteria are themselves capable of synthesizing pantothenate). In particular, bioconversion processes have been evaluated as a means of favoring production of preferred isomer of pantothenic acid. Moreover, methods of direct microbial synthesis have recently been examined as a means of facilitating D-pantothenate production.

There is still, however, significant need for improved pantothenate production processes, in particular, for microbial processes optimized to produce higher yields of desired product.

SUMMARY OF THE INVENTION

The present invention relates to improved processes (e.g., microbial syntheses) for the production of pantothenate. In particular, the present inventors have discovered that deregulation of the pantothenate biosynthetic pathway and/ or deregulation of the isoleucine-valine (ilv) pathway in microorganisms, in addition to producing significantly increased pantoate and/or pantothenate titers, results in the synthesis of an alternate product, namely [R]-3-(2-hydroxy-3-methyl-butyrylamino)-propionic acid or 3-(2-hydroxy-3-methyl-butyrylamino)-propionic acid ("HMBPA"), referred to interchangeably herein as "β-alanine 2-(R)-hydroxyisolvalerate", "β-alanine 2-hydroxyisolvalerate", "β-alanyl-α-hydroxyisovalerate" and/or "fantothenate". The pathway leading to HMBPA (referred to herein as the "HMBPA biosynthetic pathway") involves certain enzymes conventionally associated with pantothenate and/or isoleucine-valine (ilv) biosynthesis, which when overexpressed, are capable of additionally participating in the HMBPA biosynthetic pathway. In particular, the pathway includes conversion of α-ketoisovalerate to [R]-2-hydroxyisovalarate (α-HIV), catalyzed by a reductase activity (e.g., PanE1, PanE2 and/or IlvC activities), followed by condensation of α-HIV with β-alanine, catalyzed by PanC activity. As the alternative HMBPA biosynthetic pathway competes for key precursors of pantothenate biosynthesis, namely α-ketoisovalerate (α-KIV) and β-alanine, and also competes for enzymes conventionally associated with pantothenate biosynthesis, it is desirable to decrease or eliminate HMBPA biosynthesis in order to effectively increase pantothenate biosynthesis.

Accordingly, in one aspect the present invention features a process for the production of a HMBPA-free pantothenate composition that includes culturing a microorganism having a deregulated pantothenate biosynthetic pathway under conditions such that a HMBPA-free pantothenate composition is produced. In another aspect, the invention features a process for the production of a HMBPA-free pantothenate composition that involves culturing a microorganism having a deregualted pantothenate biosynthetic pathway and a deregulated isoleucine-valine (ilv) biosynthetic pathway, said microorganism having PanB activity regulated such that a HMBPA-free pantothenate composition is produced. Yet another aspect of the invention features a process for the production of a HMBPA-free pantothenate composition that involves culturing a microorganism having a deregualted pantothenate biosynthetic pathway and a deregulated isoleucine-valine (ilv) biosynthetic pathway, the microorganism having PanE activity regulated such that a HMBPA-free pantothenate composition is produced. In yet another aspect, the invention features a process for the production of a HMBPA-free pantothenate composition that involves culturing a microorganism having a deregualted pantothenate biosynthetic pathway and a deregulated isoleucine-valine (ilv) biosynthetic pathway, the microorganism having IlvC activity regulated such that a HMBPA-free pantothenate composition is produced. In yet another aspect, the invention features a process for the production of a HMBPA-free pantothenate composition that involves culturing a microorganism having a deregualted pantothenate biosynthetic pathway and a deregulated isoleucine-valine (ilv) biosynthetic pathway, said microorganism having PanB and PanE activites regulated such that a HMBPA-free pantothenate composition is produced. In yet another aspect, the invention features a process for the production of a HMBPA-free pantothenate composition that involves culturing a microorganism having a deregualted pantothenate biosynthetic pathway and a deregulated isoleucine-valine (ilv) biosynthetic pathway, said microorganism having PanB and IlvC activites regulated such that a HMBPA-free pantothenate composition is produced. Compositions produced according to the above-described methodologies are also featured as are microorganisms utilized in said methodologies. Also featured are processes for the production of a selectively mixed pantothenate:HMBPA compositions.

Other features and advantages of the invention will be apparent from the following detailed description and claims.

BRIEF DESCRIPTION OF THE DRAWINGS

FIG. 5 is a mass spectrum depicting the relative monoisotopic mass of 3-(2-hydroxy-3-methyl-butyrylamino)-propionic acid.

FIG. 6 depicts an alignment of the C-terminal amino acids from known or suspected PanB proteins.

FIG. 7 is a schematic representation of the construction of the plasmid pAN624.

FIG. 8 is a schematic representation of the construction of the plasmid pAN620.

FIG. 9 is a schematic representation of the construction of the plasmid pAN636.

FIG. 10 is a schematic representation of the construction of the plasmid pAN637 which allows selection for single or multiple copies using chloramphenicol.

DETAILED DESCRIPTION OF THE INVENTION

Figure 1:
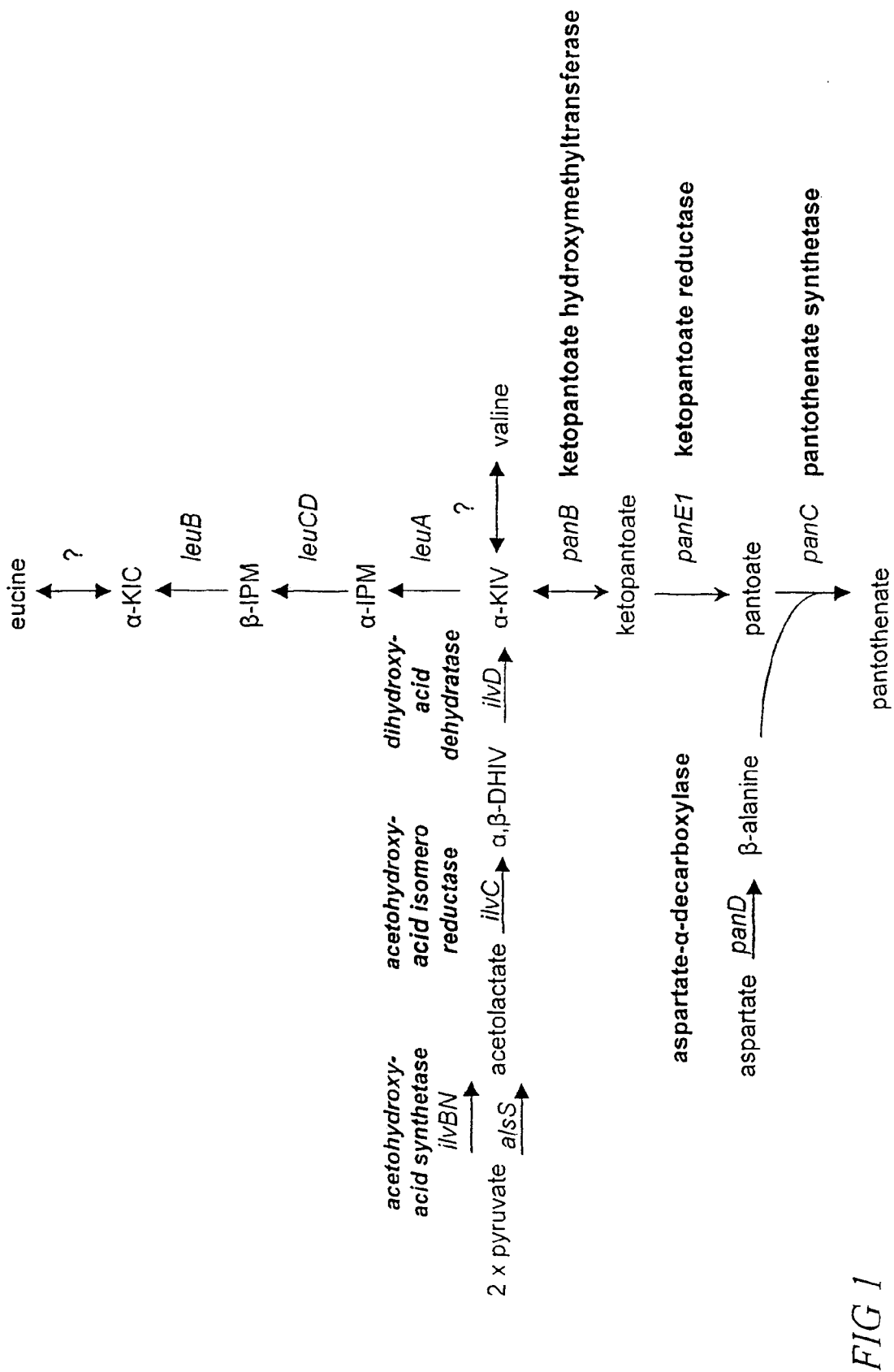
FIG. 1 is a schematic representation of the pantothenate and isoleucine-valine (ilv) biosynthetic pathways. Pantothenate biosynthetic enzymes are depicted in bold and their corresponding genes indicated in italics. Isoleucine-valine (ilv) biosynthetic enzymes are depicted in bold italics and their corresponding genes indicated in italics.

The present invention is based, at least in part, on the discovery of an alternative biosynthetic pathway in recombinant microorganisms which utilizes certain pantothenate and/or isoleucine-valine (ilv) biosynthetic enzymes and precursors to make a byproduct or side product called [R]-3-(2-hydroxy-3-methyl-butyrylamino)-propionic acid ("HMBPA"). In particular, it has been discovered that bacteria that have been engineered to have deregulated pantothenate biosynthetic and/or isoleucine-valine (ilv) biosynthetic pathways are capable of generating HMBPA from α-ketoisovalerate (α-KIV), a key product of the isoleucine-valine (ilv) biosynthetic pathway and precursor of the pantothenate biosynthetic pathway. Production of HMBPA in bacteria utilizes at least the pantothenate biosynthetic enzymes ketopantoate reductase (the panE gene product), the panE2 gene product and/or acetohydroxyisomeroreductase (the ilvC gene product) and results from the condensation of [R]-2-hydroxyisovaleric acid (α-HIV), formed by reduction of α-KIV, and β-alanine, the latter reaction being catalyzed by the pantothenate biosynthetic enzyme pantothenate synthetase (the panC gene product). The substrates α-KIV and β-alanine can be utilized for both pantothenate production and HMBPA production, β-alanine being provided, for example, by feeding and/or increased aspartate-α-decarboxylate activity (the panD gene product).

In order to decrease or eliminate competition for pantothenate biosynthesis precursors and/or biosynthetic enzymes, it is desireable to selectively regulate certain enzymes such that production is shifted away from HMBPA and towards pantoate/pantothenate. Preferably, microorganisms having a deregulated pantothenate biosynthetic pathway and/or a deregulated isoleucine-valine (ilv) biosynthetic pathway are further engineered such that PanB and/or PanE are selectively regulated. Selective regulation of PanB and/or PanE includes an optimization of levels of these enzymes such that production flows towards pantoate/pantothenate.

In particular, the invention features methods of producing compositions having increased ratios of pantothenate to HMBPA, preferably HMBPA-free pantothenate compositions. As used herein, the phrase "HMBPA-free pantothenate composition" describes a composition including pantothenate which is free of HMBPA and/or substantially free of HMBPA such that said composition includes insignificant amounts of HMBPA (i e., if HMBPA is present, it is present at a sufficiently low level or concentration relative to the level or concentration of pantothanate such that the composition can be considered HMBPA-free for technological, scientific and/or industrial purposes). Preferably, an HMBPA-free pantothenate composition includes pantothenate and, if HMBPA is present, it is present at a ratio of 10:100 (i.e., 10% HMBPA versus 90% pantothenate, for example, as determined by comparing the peak areas when a sample of product is analyzed by HPLC) or less. More preferably, an HMBPA-free pantothenate composition includes pantothenate and, if HMBPA is present, it is present at a ratio of 9:100 (i.e., 9% HMBPA versus 91% pantothenate) or less. Even more preferably, a HMBPA-free pantothenate composition includes pantothenate and, if HMBPA is present, it is present at a ratio of 8:100 (i e., 8% HMBPA versus 92% pantothenate) or less, 7:100 (i.e., 7% HMBPA versus 93% pantothenate) or less, 6:100 (i.e., 6% HMBPA versus 94% pantothenate) or less or 5:100 (i.e., 5% HMBPA versus 95% pantothenate) or less. Even more preferably, a HMBPA-free pantothenate composition includes pantothenate and, if HMBPA is present, it is present at a ratio of 0.5:100 (i.e., 0.5% HMBPA versus 99.5% pantothenate) or less, 0.2:100 (i.e., 0.2% HMBPA versus 99.8% pantothenate) or less or 0.1:100 (i.e., 0.1% HMBPA versus 99.9% pantothenate) or less. Values and ranges included and/or intermediate of the values set forth herein are also intended to be within the scope of the present invention.

In one embodiment, the invention features a process for the production of a HMBPA-free pantothenate that includes culturing a microorganism having a deregulated pantothenate biosynthetic pathway under conditions such that a HMBPA-free pantothenate composition is produced. The term "pantothenate biosynthetic pathway" includes the biosynthetic pathway involving pantothenate biosynthetic enzymes (e.g., polypeptides encoded by biosynthetic enzyme-encoding genes), compounds (e.g., substrates, intermediates or products), cofactors and the like utilized in the formation or synthesis of pantothenate. The term "pantothenate biosynthetic pathway" includes the biosynthetic pathway leading to the synthesis of pantothenate in microorganisms (e.g., in vivo) as well as the biosynthetic pathway leading to the synthesis of pantothenate in vitro.

As used herein, a microorganism "having a deregulated pantothenate biosynthetic pathway" includes a microorganism having at least one pantothenate biosynthetic enzyme deregulated (e.g., overexpressed) (both terms as defined herein) such that pantothenate production is enhanced (e.g., as compared to pantothenate production in said microorganism prior to deregulation of said biosynthetic enzyme or as compared to a wild-type microorganism). The term "pantothenate" includes the free acid form of pantothenate, also referred to as "pantothenic acid" as well as any salt thereof (e.g., derived by replacing the acidic hydrogen of pantothenate or pantothenic acid with a cation, for example, calcium, sodium, potassium, ammonium), also referred to as a "pantothenate salt". The term "pantothenate" also includes alcohol derivatives of pantothenate. Preferred pantothenate salts are calcium pantothenate or sodium pantothenate. A preferred alcohol derivative is pantothenol; Pantothenate salts and/or alcohols of the present invention include salts and/or alcohols prepared via conventional methods from the free acids described herein. In another embodiment, a pantothenate salt is synthesized directly by a microorganism of the present invention. A pantothenate salt of the present invention can likewise be converted to a free acid form of a pantothenate or pantothenic acid by conventional methodology. Preferably, a microorganism "having a deregulated pantothenate biosynthetic pathway" includes a microorganism having at least one pantothenate biosynthetic enzyme deregulated (e.g., overexpressed) such that pantothenate production is 1 g/L or greater. More preferably, a microorganism "having a deregulated pantothenate biosynthetic pathway" includes a microorganism having at least one pantothenate biosynthetic enzyme deregulated (e.g., overexpressed) such that pantothenate production is 2 g/L or greater.

The term "pantothenate biosynthetic enzyme" includes any enzyme utilized in the formation of a compound (e.g., intermediate or product) of the pantothenate biosynthetic pathway. For example, synthesis of pantoate from α-ketoisovalerate (α-KIV) proceeds via the intermediate, ketopantoate. Formation of ketopantoate is catalyzed by the pantothenate biosynthetic enzyme PanB or ketopantoate hydroxymethyltransferase (the panB gene product). Formation of pantoate is catalyzed by the pantothenate biosynthetic enzyme PanE1 or ketopantoate reductase (the panE1 gene product). Synthesis of β-alanine from aspartate is catalyzed by the pantothenate biosynthetic enzyme PanD or aspartate-α-decarboxylase (the panD gene product). Formation of pantothenate from pantoate and β-alanine (e.g., condensation) is catalyzed by the pantothenate biosynthetic enzyme PanC or pantothenate synthetase (the panC gene product). Pantothenate biosynthetic enzymes may also perform an alternative function as enzymes in the HMBPA biosynthetic pathway described herein.

Accordingly, in one embodiment, the invention features a process for the production of a HMBPA-free composition of pantothenate that includes culturing a microorganism having at least one pantothenate biosynthetic enzyme deregulated (e.g., deregulated such that pantothenate production is enhanced), said enzyme being selected, for example, from the group consisting of PanB (or ketopantoate hydroxymethyltransferase), PanC (or pantothenate synthetase), PanD (or aspartate-α-decarboxylase), PanE1 (or ketopantoate reductase). In another embodiment, the invention features a process for the production of a HMBPA-free composition of pantothenate that includes culturing a microorganism having at least two pantothenate biosynthetic enzymes deregulated, said enzymes being selected, for example, from the group consisting of PanB (or ketopantoate hydroxymethyltransferase), PanC (or pantothenate synthetase), PanD (or aspartate-α-decarboxylase), and PanE1 (or ketopantoate reductase). In another embodiment, the invention features a process for the production of a HMBPA-free composition of pantothenate that includes culturing a microorganism having at least three pantothenate biosynthetic enzymes deregulated, said enzymes being selected, for example, from the group consisting of PanB (or ketopantoate hydroxymethyltransferase), PanC (or pantothenate synthetase), PanD (or aspartate-α-decarboxylase), and PanE1 (or ketopantoate reductase). In another embodiment the invention features a process for the production of a HMBPA-free composition of pantothenate that includes culturing a microorganism having at least four pantothenate biosynthetic enzymes deregulated, for example, a microorganism having panB (or ketopantoate hydroxymethyltransferase), PanC (or pantothenate synthetase), PanD (or aspartate-a-decarboxylase), and PanE1 (or ketopantoate reductase) deregulated.

In another aspect, the invention features a process for the production of a HMBPA-free pantothenate that includes culturing a microorganism having a deregulated pantothenate biosynthetic pathway under conditions such that a HMBPA-free pantothenate composition is produced, the microorganism further having a deregulated isoleucine-valine biosynthetic pathway. The term "isoleucine-valine biosynthetic pathway" includes the biosynthetic pathway involving isoleucine-valine biosynthetic enzymes (e.g., polypeptides encoded by biosynthetic enzyme-encoding genes), compounds (e.g., substrates, intermediates or products), cofactors and the like utilized in the formation or synthesis of conversion of pyruvate to valine or isoleucine. The term "isoleucine-valine biosynthetic pathway" includes the biosynthetic pathway leading to the synthesis of valine or isoleucine in microorganisms (e.g., in vivo) as well as the biosynthetic pathway leading to the synthesis of valine or isoleucine in vitro.

As used herein, a microorganism "having a deregulated isoleucine-valine (ilv) pathway" includes a microorganism having at least one isoleucine-valine (ilv) biosynthetic enzyme deregulated (e.g., overexpressed) (both terms as defined herein) such that isoleucine and/or valine and/or the valine precursor, (α-ketoisovaerate (α-KIV) production is enhanced (e.g., as compared to isoleucine and/or valine and/or α-KIV production in said microorganism prior to deregulation of said biosynthetic enzyme or as compared to a wild-type microorganism). FIG. 1 includes a schematic representation of the isoleucine-valine biosynthetic pathway. Isoleucine-valine biosynthetic enzymes are depicted in bold italics and their corresponding genes indicated in italics. The term "isoleucine-valine biosynthetic enzyme" includes any enzyme utilized in the formation of a compound (e.g., intermediate or product) of the isoleucine-valine biosynthetic pathway. According to FIG. 1, synthesis of valine from pyruvate proceeds via the intermediates, acetolactate, α,β-dihydroxyisovalerate (α,β-DHIV) and α-ketoisovalerate (α-KIV). Formation of acetolactate from pyruvate is catalyzed by the isoleucine-valine biosynthetic enzyme acetohydroxyacid synthetase (the ilvBN gene products, or alternatively, the alsS gene product). Formation of α,β-DHIV from acetolactate is catalyzed by the isoleucine-valine biosynthetic enzyme acetohydroxyacid isomeroreductase (the ilvC gene product). Synthesis of α-KIV from α,β-DHIV is catalyzed by the isoleucine-valine biosynthetic enzyme dihydroxyacid dehydratase (the ilvD gene product). Moreover, valine and isoleucine can be interconverted with their respective α-keto compounds by branched chain amino acid transaminases. Isoleucine-valine biosynthetic enzymes may also perform an alternative function as enzymes in the HMBPA biosynthetic pathway described herein.

Accordingly, in one embodiment, the invention features a process for the production of a HMBPA-free composition of pantothenate that includes culturing a microorganism having at least one isoleucine-valine (ilv) biosynthetic enzyme deregulated (e.g., deregulated such that valine and/or isoleucine and/or α-KIV production is enhanced), said enzyme being selected, for example, from the group consisting of IlvBN, AlsS (or acetohydroxyacid synthetase), IlvC (or acetohydroxyacid isomeroreductase) and IlvD (or dihydroxyacid dehydratase). In another embodiment, the invention features a process for the production of a HMBPA-free composition of pantothenate that includes culturing a microorganism having at least two isoleucine-valine (ilv) biosynthetic enzymes deregulated, said enzyme being selected, for example, from the group consisting of IlvBN, AlsS (or acetohydroxyacid synthetase), IlvC (or acetohydroxyacid isomeroreductase) and IlvD (or dihydroxyacid dehydratase). In another embodiment, the invention features a process for the production of a HMBPA-free composition of pantothenate that includes culturing a microorganism having at least three isoleucine-valine (ilv) biosynthetic enzymes deregulated, for example, said microorganism having IlvBN or AlsS (or acetohydroxyacid synthetase), IlvC (or acetohydroxyacid isomeroreductase) and IlvD (or dihydroxyacid dehydratase) deregulated.

As mentioned herein, enzymes of the pantothenate biosynthetic pathway and/or the isoleucine-valine (ilv) pathway have been discovered to have an alternative activity in the synthesis of [R]-3-(2-hydroxy-3-methyl-butyrylamino)-propionic acid ("HMBPA") or the [R]-3-(2-hydroxy-3-methyl-butyrylamino)-propionic acid ("HMBPA") biosynthetic pathway. The term "[R]-3-(2-hydroxy-3-methyl-butyrylamino)-propionic acid ("HMBPA") biosynthetic pathway" includes the alternative biosynthetic pathway involving biosynthetic enzymes and compounds (e.g., substrates and the like) traditionally associated with the pantothenate biosynthetic pathway and/or isoleucine-valine (ilv) biosynthetic pathway utilized in the formation or synthesis of HMBPA. The term "HMBPA biosynthetic pathway" includes the biosynthetic pathway leading to the synthesis of HMBPA in microorganisms (e.g., ;i? vivo) as well as the biosynthetic pathway leading to the synthesis of HMBPA in vitro.

The term "HMBPA biosynthetic enzyme" includes any enzyme utilized in the formation of a compound (e.g., intermediate or product) of the HMBPA biosynthetic pathway. For example, synthesis of 2-hydroxyisovaleric acid ($\alpha$-HIV) from $\alpha$-ketoisovalerate ($\alpha$-KIV) is catalyzed by the panE1 or panE2 gene product (PanE1 is alternatively referred to herein as ketopantoate reductase) and/or is catalyzed by the ilvC gene product (alternatively referred to herein as acetohydroxyacid isomeroreductase). Formation of HMBPA from $\beta$-alanine and $\alpha$-HIV is catalyzed by the panC gene product (alternatively referred to herein as pantothenate synthetase).

The term "[R]-3-(2-hydroxy-3-methyl-butyrylamino)-propionic acid ("HMBPA")" includes the free acid form of HMBPA, also referred to as "[R]-3-(2-hydroxy-3-methyl-butyrylamino)-propionate" as well as any salt thereof (e.g., derived by replacing the acidic hydrogen of 3-(2-hydroxy-3-methyl-butyrylamino)-propionic acid or 3-(2-hydroxy-3-methyl-butyrylamino)-propionate with a cation, for example, calcium, sodium, potassium, ammonium), also referred to as a "3-(2-hydroxy-3-methyl-butyrylamino)-propionic acid salt" or "HMBPA salt". Preferred HMBPA salts are calcium HMBPA or sodium HMBPA. HMBPA salts of the present invention include salts prepared via conventional methods from the free acids described herein. An HMBPA salt of the present invention can likewise be converted to a free acid form of 3-(2-hydroxy-3-methyl-butyrylamino)-propionic acid or 3-(2-hydroxy-3-methyl-butyrylamino)-propionate by conventional methodology.

Based at least in part on the discovery that overexpression or deregulation of the pantothenate biosynthetic pathway and/or isoleucine-valine (ilv) pathway can result in alternative production of HMBPA (as compared to desired pantothenate production), the present invention features processes for the production of HMBPA-free pantothenate that involve culturing microorganisms that not only have the pantothenate biosynthetic pathway and/or the isoleucine-valine (ilv) pathway deregulated, but that further have certain enzymes selectively regulated such that production of HMBPA-free pantothenate compositions is favored. As defined herein, the term "selectively regulated" includes selecting for regulation or targeting a particular enzyme or enzymes from the pantothenate biosynthetic pathway or the isoleucine-valine (ilv) pathway known to be involved in both pantothenate and HMBPA synthesis in a manner that favors pantothenate production over HMBPA production. Preferred enzymes selected or targeted for regulation include PanE1, PanE2, PanB and/or IlvC.

In one embodiment, Pan E1 is selectively regulated. For example, the present inventors have discovered that overexpression of PanE1 can catalyze HMBPA precursor formation, therefore selectively regulating the amount or activity (e.g., to slightly decrease PanE1 levels or activity) can shift formation from HMBPA production to pantothenate production (i e., favor pantothenate production over HMBPA production). Moreover, it has been discovered that PanE2 favors HMBPA production. Accordingly, another embodiment, features deleting or regulating panE2.

Likewise, the present inventors have discovered that increasing PanB activity can shift formation from the alternative HMBPA biosynthetic pathway to the pantothenate biosynthetic pathway, therefore selectively regulating the amount or activity of PanB can favor pantothenate production over HMBPA production. In one embodiment, PanB activity is increased by overexpressing or deregulating the panB gene. In another embodiment, PanB activity is increased by expressing multiple copies of the panB gene. PanB activity can be increased by decreasing feedback inhibtion of PanB. In particular, is has been discovered that PanB activity can be increased by regulating (e.g., selectively regulating) pantothenate kinase, a key enzyme in the formation of Coenzyme A (CoA) from pantothenate (see e.g., U.S. patent application Ser. No. 09/09/667,569). Regulation of pantothenate kinase (e.g., decreasing the activity or level of pantothenate kinase) reduced the production of CoA, in turn reducing feedback inhibition of PanB as well as favoring pantothenate accumulation. In one embodiment, pantothenate kinase activity is decreased (and PanB activity is in turn increased) by deleting CoaA and downregulating CoaX activity (CoaA and CoaX are both capable of catalyzing the first step in CoA biosynthesis in certain microorganisms). In another embodiment, pantothenate kinase activity is decreased (and PanB activity is in turn increased) by deleting CoaX and downregulating CoaA. In yet another embodiment, pantothenate kinase activity is decreased (and PanB activity is in turn increased) by downregulating CoaA and CoaX activities.

Yet another aspect of the present invention features processes for the production of HMBPA-free pantothenate that include culturing microorganisms under culture conditions selected to favor pantothenate production over HMBPA production. In particular, it has been discovered that conditions including, but not limited to, reduced steady state glucose, increased steady state dissolved oxygen and/or excess serine favor pantothenate production over HMBPA production. The term "reduced steady state glucose" includes steady state glucose levels less or lower that those routinely utilized for culturing the microorganism in question. For example, culturing the *Bacillus* microorganisms described in the instant Examples is routinely done in the presence of about 0.2–1.0 g/L steady state glucose. Accordingly, reduced steady state glucose levels preferably include levels of less than 0.2 g.L steady state glucose. The term "increased steady state dissolved oxygen" includes steady state dissolved oxygen levels increased or higher than those routinely utilized for culturing the microorganism in question and, for example, inversely correlates with reduced steady state glucose levels. For example, culturing the *Bacillus* microorganisms described in the instant Examples is routinely done in the presence of about 10–30% dissolved oxygen. Accordingly, increased steady state dissolved oxygen can include levels of greater that 30% dissolved oxygen, preferably as great as 95% dissolved oxygen. The term "excess serine" includes serine levels increased or higher that those routinely utilized for culturing the microorganism in question. For example, culturing the *Bacillus* microorganisms described in the instant Examples is routinely done in the presence of about 0–2.5 g/L serine. Accordingly, excess serine levels can include levels of greater than 2.5 g/L serine, preferably between about 2.5 and 20 g/L serine.

In yet another embodiment, HMBPA production is favored by increasing pantothenate and/or isoleucine-valine (ilv) biosynthetic pathway precursors and/or intermediates as defined herein (e.g., culturing microorganisms in the presence of excess β-alanine, valine and/or α-KIV) or, alternatively, culturing microorganisms capable of producing significant levels of β-alanine in the absence of a β-alanine feed (i e., β-alanine independent microorganisms, as described in U.S. patent application Ser. No. 09/09/667,569).

Various aspects of the invention are described in further detail in the following subsections.

I. Targeting Genes Encoding Various Pantothenate and/or Isoleucine-Valine(ilv) and/or HMBPA Biosynthetic Enzymes In one embodiment, the present invention features targeting or modifying various biosynthetic enzymes of the pantothenate and/or isoleucine-valine(ilv) and/or HMBPA biosynthetic pathways. In particular, the invention features modifying various enzymatic activities associated with said pathways by modifying or altering the genes encoding said biosynthetic enzymes.

The term "gene", as used herein, includes a nucleic acid molecule (e.g., a DNA molecule or segment thereof) that, in an organism, can be separated from another gene or other genes, by intergenic DNA (i.e., intervening or spacer DNA which naturally flanks the gene and/or separates genes in the chromosomal DNA of the organism). Alternatively, a gene may slightly overlap another gene (e.g., the 3' end of a first gene overlapping the 5' end of a second gene), the overlapping genes separated from other genes by intergenic DNA. A gene may direct synthesis of an enzyme or other protein molecule (e.g., may comprise coding sequences, for example, a contiguous open reading frame (ORF) which encodes a protein) or may itself be functional in the organism. A gene in an organism, may be clustered in an operon, as defined herein, said operon being separated from other genes and/or operons by the intergenic DNA. An "isolated gene", as used herein, includes a gene which is essentially free of sequences which naturally flank the gene in the chromosomal DNA of the organism from which the gene is derived (i.e., is free of adjacent coding sequences that encode a second or distinct protein, adjacent structural sequences or the like) and optionally includes 5' and 3' regulatory sequences, for example promoter sequences and/or terminator sequences. In one embodiment, an isolated gene includes predominantly coding sequences for a protein (e.g., sequences which encode Bacillus proteins). In another embodiment, an isolated gene includes coding sequences for a protein (e.g., for a *Bacillus* protein) and adjacent 5' and/or 3' regulatory sequences from the chromosomal DNA of the organism from which the gene is derived (e.g., adjacent 5' and/or 3' *Bacillus* regulatory sequences). Preferably, an isolated gene contains less than about 10 kb, 5 kb, 2 kb, 1 kb, 0.5 kb, 0.2 kb, 0.1 kb, 50 bp, 25 bp or 10 bp of nucleotide sequences which naturally flank the gene in the chromosomal DNA of the organism from which the gene is derived.

The term "operon" includes at least two adjacent genes or ORFs, optionally overlapping in sequence at either the 5' or 3' end of at least one gene or ORF. The term "operon" includes a coordinated unit of gene expression that contains a promoter and possibly a regulatory element associated with one or more adjacent genes or ORFs (e.g., structural genes encoding enzymes, for example, biosynthetic enzymes). Expression of the genes (e.g., structural genes) .can be coordinately regulated, for example, by regulatory proteins binding to the regulatory element or by anti-termination of transcription. The genes of an operon (e.g., structural genes) can be transcribed to give a single mRNA that encodes all of the proteins.

A "gene having a mutation" or "mutant gene" as used herein, includes a gene having a nucleotide sequence which includes at least one alteration (e.g., substitution, insertion, deletion) such that the polypeptide or protein encoded by said mutant exhibits an activity that differs from the polypeptide or protein encoded by the wild-type nucleic acid molecule or gene. In one embodiment, a gene having a mutation or mutant gene encodes a polypeptide or protein having an increased activity as compared to the polypeptide or protein encoded by the wild-type gene, for example, when assayed under similar conditions (e.g.,assayed in microorganisms cultured at the same temperature). As used herein, an "increased activity" or "increased enzymatic activity" is one that is at least 5% greater than that of the polypeptide or protein encoded by the wild-type nucleic acid molecule or gene, preferably at least 5–10% greater, more preferably at least 10–25% greater and even more preferably at least 25–50%, 50–75% or 75–100% greater than that of the polypeptide or protein encoded by the wild-type nucleic acid molecule or gene. Ranges intermediate to the above-recited values, e.g., 75–85%, 85–90%, 90–95%, are also intended to be encompassed by the present invention. As used herein, an "increased activity" or "increased enzymatic activity" can also include an activity that is at least 1.25-fold greater than the activity of the polypeptide or protein encoded by the wild-type gene, preferably at least 1.5-fold greater, more preferably at least 2-fold greater and even more preferably at least 3-fold, 4-fold, 5-fold, 10-fold, 20-fold, 50-fold, 100-fold greater than the activity of the polypeptide or protein encoded by the wild-type gene.

In another embodiment, a gene having a mutation or mutant gene encodes a polypeptide or protein having a reduced activity as compared to the polypeptide or protein encoded by the wild-type gene, for example, when assayed under similar conditions (e.g., assayed in microorganisms cultured at the same temperature). A mutant gene also can encode no polypeptide or have a reduced level of production of the wild-type polypeptide. As used herein, a "reduced activity" or "reduced enzymatic activity" is one that is at least 5% less than that of the polypeptide or protein encoded by the wild-type nucleic acid molecule or gene, preferably at least 5–10% less, more preferably at least 10–25% less and even more preferably at least 25–50%, 50–75% or 75–100% less than that of the polypeptide or protein encoded by the wild-type nucleic acid molecule or gene.

Ranges intermediate to the above-recited values, e.g., 75–85%, 85–90%, 90–95%, are also intended to be encompassed by the present invention. As used herein, a "reduced activity" or "reduced enzymatic activity" can also include an activity that has been deleted or "knocked out" (e.g., approximately 100% less activity than that of the polypeptide or protein encoded by the wild-type nucleic acid molecule or gene).

Activity can be determined according to any well accepted assay for measuring activity of a particular protein of interest. Activity can be measured or assayed directly, for example, measuring an activity of a protein isolated or purified from a cell or microorganism. Alternatively, an activity can be measured or assayed within a cell or microorganism or in an extracellular medium. For example, assaying for a mutant gene (i.e., said mutant encoding a reduced enzymatic activity) can be accomplished by expressing the mutated gene in a microorganism, for example, a mutant microorganism in which the enzyme is a temperature-sensitive, and assaying the mutant gene for the ability to complement a temperature sensitive (Ts) mutant for enzymatic activity. A mutant gene that encodes an "increased enzymatic activity" can be one that complements the. Ts mutant more effectively than, for example, a corresponding wild-type gene. A mutant gene that encodes a "reduced enzymatic activity" is one that complements the Ts mutant less effectively than, for example, a corresponding wild-type gene.

It will be appreciated by the skilled artisan that even a single substitution in a nucleic acid or gene sequence (e.g., a base substitution that encodes an amino acid change in the corresponding amino acid sequence) can dramatically affect the activity of an encoded polypeptide or protein as compared to the corresponding wild-type polypeptide or protein. A mutant gene (e.g., encoding a mutant polypeptide or protein), as defined herein, is readily distinguishable from a nucleic acid or gene encoding a protein homologue in that a mutant gene encodes a protein or polypeptide having an altered activity, optionally observable as a different or distinct phenotype in a microorganism expressing said mutant gene or producing said mutant protein or polypeptide (i.e., a mutant microorganism) as compared to a corresponding microorganism expressing the wild-type gene. By contrast, a protein homologue can have an identical or substantially similar activity, optionally phenotypically indiscernable when produced in a microorganism, as compared to a corresponding microorganism expressing the wild-type gene. Accordingly it is not, for example, the degree of sequence identity between nucleic acid molecules, genes, protein or polypeptides that serves to distinguish between homologues and mutants, rather it is the activity of the encoded protein or polypeptide that distinguishes between homologues and mutants: homologues having, for example, low (e.g., 30–50% sequence identity) sequence identity yet having substantially equivalent functional activities, and mutants, for example sharing 99% sequence identity yet having dramatically different or altered functional activities.

It will also be appreciated by the skilled artisan that nucleic acid molecules, genes, protein or polypeptides for use in the instant invention can be derived from any microorganisms having a HMBPA biosynthetic pathway, an ilv biosynthetic pathway or a pantothenate biosynthetic pathway. Such nucleic acid molecules, genes, protein or polypeptides can be identified by the skilled artisan using known techniques such as homology screening, sequence comparison and the like, and can be modified by the skilled artisan in such a way that expression or production of these nucleic acid molecules, genes, protein or polypeptides occurs in a recombinant microorganism (e.g., by using appropriate promotors, ribosomal binding sites, expression or integration vectors, modifying the sequence of the genes such that the transcription is increased (taking into account the preferable codon usage), etc., according to techniques described herein and those known in the art).

In one embodiment, the genes of the present invention are derived from a Gram positive microorganism organism (e.g., a microorganism which retains basic dye, for example, crystal violet, due to the presence of a Gram-positive wall surrounding the microorganism). The term "derived from" (e.g., "derived from" a Gram positive microorganism) refers to a gene which is naturally found in the microorganism (e.g., is naturally found in a Gram positive microorganism). In a preferred embodiment, the genes of the present invention are derived from a microorganism belonging to a genus selected from the group consisting of *Bacillus, Corynebacterium* (e.g., *Corynebacterium glutamicum*), *Lactobacillus, Lactococci* and *Streptomyces*. In a more preferred embodiment, the genes of the present invention are derived from a microorganism is of the genus *Bacillus*. In another preferred embodiment, the genes of the present invention are derived from a microorganism selected from the group consisting of *Bacillus subtilis, Bacillus lentimorbus, Bacillus lentus, Bacillus firmus, Bacillus pantothenticus, Bacillus amyloliquefaciens, Bacillus cereus, Bacillus circulans, Bacillus coagulans, Bacillus licheniformis, Bacillus magaterium, Bacillus pumilus, Bacillus thuringiensis, Bacillus halodurans*, and other Group 1 *Bacillus* species, for example, as characterized by 16S rRNA type. In another preferred embodiment, the gene is derived from *Bacillus brevis* or *Bacillus stearothermophilus*. In another preferred embodiment, the genes of the present invention are derived from a microorganism selected from the group consisting of *Bacillus licheniformis, Bacillus amyloliquefaciens, Bacillus subtilis*, and *Bacillus pumilus*. In a particularly preferred embodiment, the gene is derived from *Bacillus subtilis* (e.g., is *Bacillus subtilis*-derived). The term "derived from *Bacillus subtilis*" or "*Bacillus subtilis*-derived" includes a gene which is naturally found in the microorganism *Bacillus subtilis*. Included within the scope of the present invention are *Bacillus*-derived genes (e.g., *B. subtilis*-derived genes), for example, *Bacillus* or *B. subtilis* coaX genes, serA genes, glyA genes, coaA genes, pan genes and/or ilv genes.

In another embodiment, the genes of the present invention are derived from a Gram negative (excludes basic dye) microorganism. In a preferred embodiment, the genes of the present invention are derived from a microorganism belonging to a genus selected from the group consisting of *Salmonella* (e.g., *Salmonella typhimurium*), *Escherichia, Klebsiella, Serratia*, and *Proteus*. In a more preferred embodiment, the genes of the present invention are derived from a microorganism of the genus *Escherichia*. In an even more preferred embodiment, the genes of the present invention are derived from *Escherichia coli*. In another embodiment, the genes of the present invention are derived from *Saccharomyces* (e.g., *Saccharomyces cerevisiae*).

II Recombinant Nucleic Acid Molecules and Vectors

The present invention further features recombinant nucleic acid molecules (e.g., recombinant DNA molecules) that include genes described herein (e.g., isolated genes), preferably *Bacillus* genes, more preferably *Bacillus subtilis* genes, even more preferably *Bacillus subtilis* pantothenate biosynthetic genes and/or isoleucine-valine (ilv) biosynthetic genes and/or HMBPA biosynthetic genes. The term "recombinant nucleic acid molecule" includes a nucleic acid molecule (e.g., a DNA molecule) that has been altered, modified or engineered such that it differs in nucleotide sequence from the native or natural nucleic acid molecule from which the recombinant nucleic acid molecule was derived (e.g., by addition, deletion or substitution of one or more nucleotides). Preferably, a recombinant nucleic acid molecule (e.g., a recombinant DNA molecule) includes an isolated gene of the present invention operably linked to regulatory sequences. The phrase "operably linked to regulatory sequence(s)" means that the nucleotide sequence of the gene of interest is linked to the regulatory sequence(s) in a manner which allows for expression (e.g., enhanced, increased, constitutive, basal, attenuated, decreased or repressed expression) of the gene, preferably expression of a gene product encoded by the gene (e.g., when the recombinant nucleic acid molecule is included in a recombinant vector, as defined herein, and is introduced into a microorganism).

The term "regulatory sequence" includes nucleic acid sequences which affect (e.g., modulate or regulate) expression of other nucleic acid sequences (i.e., genes). In one embodiment, a regulatory sequence is included in a recombinant nucleic acid molecule in a similar or identical position and/or orientation relative to a particular gene of interest as is observed for the regulatory sequence and gene of interest as it appears in nature, e.g., in a native position and/or orientation. For example, a gene of interest can be included in a recombinant nucleic acid molecule operably linked to a regulatory sequence which accompanies or is adjacent to the gene of interest in the natural organism (e.g., operably linked to "native" regulatory sequences (e.g. to the "native" promoter). Alternatively, a gene of interest can be included in a recombinant nucleic acid molecule operably linked to a regulatory sequence which accompanies or is adjacent to another (e.g., a different) gene in the natural organism. Alternatively, a gene of interest can be included in a recombinant nucleic acid molecule operably linked to a regulatory sequence from another organism. For example, regulatory sequences from other microbes (e.g., other bacterial regulatory sequences, bacteriophage regulatory sequences and the like) can be operably linked to a particular gene of interest.

In one embodiment, a regulatory sequence is a non-native or non-naturally-occurring sequence (e.g., a sequence which has been modified, mutated, substituted, derivatized, deleted including sequences which are chemically synthesized). Preferred regulatory sequences include promoters, enhancers, termination signals, anti-termination signals and other expression control elements (e.g., sequences to which repressors or inducers bind and/or binding sites for transcriptional and/or translational regulatory proteins, for example, in the transcribed mRNA). Such regulatory sequences are described, for example, in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. Regulatory sequences include those which direct constitutive expression of a nucleotide sequence in a microorganism (e.g., constitutive promoters and strong constitutive promoters), those which direct inducible expression of a nucleotide sequence in a microorganism (e.g., inducible promoters, for example, xylose inducible promoters) and those which attenuate or repress expression of a nucleotide sequence in a microorganism (e.g., attenuation signals or repressor sequences). It is also within the scope of the present invention to regulate expression of a gene of interest by removing or deleting regulatory sequences. For example, sequences involved in the negative regulation of transcription can be removed such that expression of a gene of interest is enhanced.

In one embodiment, a recombinant nucleic acid molecule of the present invention includes a nucleic acid sequence or gene that encodes at least one bacterial gene product (e.g., a pantothenate biosynthetic enzyme, an isoleucine-valine biosynthetic enzyme and/or a HMBPA biosynthetic enzyme) operably linked to a promoter or promoter sequence. Preferred promoters of the present invention include *Bacillus* promoters and/or bacteriophage promoters (e.g., bacteriophage which infect *Bacillus*). In one embodiment, a promoter is a *Bacillus* promoter, preferably a strong *Bacillus* promoter (e.g., a promoter associated with a biochemical housekeeping gene in *Bacillus* or a promoter associated with a glycolytic pathway gene in *Bacillus*). In another embodiment, a promoter is a bacteriophage promoter. In a preferred embodiment, the promoter is from the bacteriophage SP01. In a particularly preferred embodiment, a promoter is selected from the group consisting of $P_{15}$, $P_{26}$ or $P_{veg}$, having for example, the following respective sequences:
GCTATTGACGACAGCTATGGTTCACT-
GTCCACCAACCAAAACTGTGCTCAGTAC-
CGCCAATATTTCTCCCTTGAGGGGTA-
CAAAGAGGTGTCCCTAGAAGAGATCCACGCT
GTGTAAAAATTTTACAAAAAGGTAT-
TGACTTTCCCTACAGGGTGTG-
TAATAATTTAATTACAGGCGGGGGCAAC-
CCCGCCTGT(SEQ ID NO: 1),
GCCTACCTAGCTTCCAAGAAAGATATC-
CTAACAGCACAAGAGCGGAAAGAT-
GTTTTGTTCTACATCCAGAACAACCTCT-
GCTAAAATTCCTGAAAAATTTTGCAAAAAGT
TGTTGACTTTATCTACAAGGTGTGG-
TATAATAATCTTAACAACAGCAGGACGC (SEQ ID NO:2), and
GAGGAATCATAGAATTTTGT-
CAAAATAATTTTATTGACAACGTCTTAT-
TAACGTTGATATAATTTAAATTT-
TATTTGACAAAAATGGGCTCGTGTTGTACA
ATAAATGTAGTGAGGTGGATGCAATG (SEQ ID NO:3). Additional preferred promoters include tef (the translational elongation factor (TEF) promoter) and pyc (the pyruvate carboxylase (PYC) promoter), which promote high level expression in *Bacillus* (e.g., *Bacillus subtilis*). Additional preferred promoters, for example, for use in Gram positive microorganisms include, but are not limited to, amy and SPO2 promoters. Additional preferred promoters, for example, for use in Gram negative microorganisms include, but are not limited to, cos, tac, trp, tet, trp-tet, lpp, lac, lpp-lac, lacIQ, T7, T5, T3, gal, trc, ara, SP6, λ-PR or λ-PL.

In another embodiment, a recombinant nucleic acid molecule of the present invention includes a terminator sequence or terminator sequences (e.g., transcription terminator sequences). The term "terminator sequences" includes regulatory sequences that serve to terminate transcription of mRNA. Terminator sequences (or tandem transcription terminators) can further serve to stabilize mRNA (e.g., by adding structure to mRNA), for example, against nucleases.

In yet another embodiment, a recombinant nucleic acid molecule of the present invention includes sequences that allow for detection of the vector containing said sequences (i.e., detectable and/or selectable markers), for example, genes that encode antibiotic resistance sequences or that overcome auxotrophic mutations, for example, trpC, drug markers, fluorescent markers, and/or colorimetric markers (e.g., lacZ/β-galactosidase). In yet another embodiment, a recombinant nucleic acid molecule of the present invention includes an artificial ribosome binding site (RBS) or a sequence that gets transcribed into an artificial RBS. The term "artificial ribosome binding site (RBS)" includes a site within an mRNA molecule (e.g., coded within DNA) to which a ribosome binds (e.g., to initiate translation) which differs from a native RBS (e.g., a RBS found in a naturally-occurring gene) by at least one nucleotide. Preferred artificial RBSs include about 5–6, 7–8, 9–10, 11–12, 13–14, 15–16, 17–18, 19–20, 21–22, 23–24, 25–26, 27–28, 29–30 or more nucleotides of which about 1–2, 3–4, 5–6, 7–8, 9–10, 11–12, 13–15 or more differ from the native RBS (e.g., the native RBS of a gene of interest, for example, the native panB RBS TAAACATGAGGAGGAGAAAACATG (SEQ ID NO:4) or the native panD RBS ATTCGAGAAATGGAGAGAATATAATATG (SEQ ID NO:5)). Preferably, nucleotides that differ are substituted such that they are identical to one or more nucleotides of an ideal RBS when optimally aligned for comparisons. Ideal RBSs include, but are not limited to, AGAAAGGAGGTGA (SEQ ID NO:6), TTAAGAAAGGAGGTGANNNNATG (SEQ ID NO:7), TTAGAAAGGAGGTGANNNNNATG (SEQ ID NO:8), AGAAAGGAGGTGANNNNNNATG (SEQ ID NO:9), and AGAAAGGAGGTGANMNNATG (SEQ ID NO:10). Artificial RBSs can be used to replace the naturally-occurring or native RBSs associated with a particular gene. Artificial RBSs preferably increase translation of a particular gene. Preferred artificial RBSs (e.g., RBSs for increasing the translation of panB, for example, of B. subtilis panB) include CCCTCTAGAAGGAGGAGAAAACATG (SEQ ID NO:11) and CCCTCTAGAGGAGGAGAAAACATG (SEQ ID NO:12). Preferred artificial RBSs (e.g., RBSs for increasing the translation of panD, for example, of B. subtilis panD) include TTAGAAAGGAGGATTTAAATATG (SEQ ID NO:13), TTAGAAAGGAGGTTTAATTAATG (SEQ ID NO:14), TTAGAAAGGAGGTGATTTAAATG (SEQ ID NO:15), TTAGAAAGGAGGTGTTTAAAATG (SEQ ID NO:16), ATTCGAGAAAGGAGGTGAATATAATATG (SEQ ID NO:17), ATTCGAGAAAGGAGGTGAATAATAATG (SEQ ID NO:18) and ATTCGTAGAAAGGAGGTGAATTAATATG (SEQ ID NO:19).

The present invention further features vectors (e.g., recombinant vectors) that include nucleic acid molecules (e.g., genes or recombinant nucleic acid molecules comprising said genes) as described herein. The term "recombinant vector" includes a vector (e.g., plasmid, phage, phasmid, virus, cosmid or other purified nucleic acid vector) that has been altered, modified or engineered such that it contains greater, fewer or different nucleic acid sequences than those included in the native or natural nucleic acid molecule from which the recombinant vector was derived. Preferably, the recombinant vector includes a biosynthetic enzyme-encoding gene or recombinant nucleic acid molecule including said gene, operably linked to regulatory sequences, for example, promoter sequences, terminator sequences and/or artificial ribosome binding sites (RBSs), as defined herein. In another embodiment, a recombinant vector of the present invention includes sequences that enhance replication in bacteria (e.g., replication-enhancing sequences). In one embodiment, replication-enhancing sequences function in E. coli. In another embodiment, replication-enhancing sequences are derived from pBR322.

In yet another embodiment, a recombinant vector of the present invention includes antibiotic resistance sequences. The term "antibiotic resistance sequences" includes sequences which promote or confer resistance to antibiotics on the host organism (e g, Bacillus). In one embodiment, the antibiotic resistance sequences are selected from the group consisting of cat (chloramphenicol resistance) sequences, tet (tetracycline resistance) sequences, erm (erythromycin resistance) sequences, neo (neomycin resistance) sequences, kan (kanamycin resistence) sequences and spec (spectinomycin resistance) sequences. Recombinant vectors of the present invention can further include homologous recombination sequences (e.g., sequences designed to allow recombination of the gene of interest into the chromosome of the host organism). For example, bpr; vpr; or amyE sequences can be used as homology targets for recombination into the host chromosome. It will further be appreciated by one of skill in the art that the design of a vector can be tailored depending on such factors as the choice of microorganism to be genetically engineered, the level of expression of gene product desired and the like.

IV Recombinant Microorganisms

The present invention further features microorganisms, i.e., recombinant microorganisms, that include vectors or genes (e.g., wild-type and/or mutated genes) as described herein. As used herein, the term "recombinant microorganism" includes a microorganism (e.g., bacteria, yeast cell, fungal cell, etc.) that has been genetically altered, modified or engineered (e.g., genetically engineered) such that it exhibits an altered, modified or different genotype and/or phenotype (e.g., when the genetic modification affects coding nucleic acid sequences of the microorganism) as compared to the naturally-occurring microorganism from which it was derived.

In one embodiment, a recombinant microorganism of the present invention is a Gram positive organism (e.g., a microorganism which retains basic dye, for example, crystal violet, due to the presence of a Gram-positive wall surrounding the microorganism). In a preferred embodiment, the recombinant microorganism is a microorganism belonging to a genus selected from the group consisting of *Bacillus, Corynebacterium, Lactobacillus, Lactococci* and *Streptomyces*. In a more preferred embodiment, the recombinant microorganism is of the genus *Bacillus*. In another preferred embodiment, the recombinant microorganism is selected from the group consisting of *Bacillus subtilis, Bacillus lentimorbus, Bacillus lentus, Bacillus firmus, Bacillus pantothenticus, Bacillus amyloliquefaciens, Bacillus cereus, Bacillus circulans, Bacillus coagulans, Bacillus licheniformis, Bacillus megaterium, Bacillus pumilus, Bacillus thuringiensis, Bacillus halodurans*, and other Group 1 Bacillus species, for example, as characterized by 16S rRNA type. In another preferred embodiment, the recombinant microorganism is *Bacillus brevis* or *Bacillus stearothermophilus*. In another preferred embodiment, the recombinant microorganism is selected from the group consisting of *Bacillus licheniformis, Bacillus amyloliquefaciens, Bacillus subtilis*, and *Bacillus pumilus*.

In another embodiment, the recombinant microorganism is a Gram negative (excludes basic dye) organism. In a preferred embodiment, the recombinant microorganism is a microorganism belonging to a genus selected from the group consisting of *Salmonella, Escherichia, Klebsiella, Serratia*, and *Proteus*. In a more preferred embodiment, the recombinant microorganism is of the genus *Escherichia*. In an even more preferred embodiment, the recombinant microorganism is *Escherichia coli*. In another embodiment, the recombinant microorganism is Saccharomyces (e.g., *S. cerevisiae*).

A preferred "recombinant" microorganism of the present invention is a microorganism having a deregulated pantothenate biosynthesis pathway or enzyme, a deregulated isoleucine-valine (ilv) biosynthetic pathway or enzyme and/or a modified HMBPA biosynthetic pathway or enzyme. The term "deregulated" or "deregulation" includes the alteration or modification of at least one gene in a microorganism that encodes an enzyme in a biosynthetic pathway, such that the level or activity of the biosynthetic enzyme in the microorganism is altered or modified. Preferably, at least one gene that encodes an enzyme in a biosynthetic pathway is altered or modified such that the gene product is enhanced or increased. The phrase "deregulated pathway" can also include a biosynthetic pathway in which more than one gene that encodes an enzyme in a biosynthetic pathway is altered or modified such that the level or activity of more than one biosynthetic enzyme is altered or modified. The ability to "deregulate" a pathway (e.g., to simultaneously deregulate more than one gene in a given biosynthetic pathway) in a microorganism in some cases arises from the particular phenomenon of microorganisms in which more than one enzyme (e.g., two or three biosynthetic enzymes) are encoded by genes occurring adjacent to one another on a contiguous piece of genetic material termed an "operon" (defined herein). Due to the coordinated regulation of genes included in an operon, alteration or modification of the single promoter and/or regulatory element can result in alteration or modification of the expression of each gene product encoded by the operon. Alteration or modification of the regulatory element can include, but is not limited to removing the endogenous promoter and/or regulatory element(s), adding strong promoters, inducible promoters or multiple promoters or removing regulatory sequences such that expression of the gene products is modified, modifying the chromosomal location of the operon, altering nucleic acid sequences adjacent to the operon or! within the operon such as a ribosome binding site, increasing the copy number of the operon, modifying proteins (e.g., regulatory proteins, suppressors, enhancers, transcriptional activators and the like) involved in transcription of the operon and/or translation of the gene products of the operon, or any other conventional means of deregulating expression of genes routine in the art (including but not limited to use of antisense nucleic acid molecules, for example, to block expression of repressor proteins). Deregulation can also involve altering the coding region of one or more genes to yield, for example, an enzyme that is feedback resistant or has a higher or lower specific activity.

In another preferred embodiment, a recombinant microorganism is designed or engineered such that at least one pantothenate biosynthetic enzyme, at least one isoleucine-valine biosynthetic enzyme, and/or at least one HMBPA biosynthetic enzyme is overexpressed. The term "overexpressed" or "overexpression" includes expression of a gene product (e.g., a biosynthetic enzyme) at a level greater than that expressed prior to manipulation of the microorganism or in a comparable microorganism which has not been manipulated. In one embodiment, the microorganism can be genetically designed or engineered to overexpress a level of gene product greater than that expressed in a comparable microorganism which has not been engineered.

Genetic engineering can include, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, for example, to block expression of repressor proteins). Genetic engineering can also include deletion of a gene, for example, to block a pathway or to remove a repressor.

In another embodiment, the microorganism can be physically or environmentally manipulated to overexpress a level of gene product greater than that expressed prior to manipulation of the microorganism or in a comparable microorganism which has not been manipulated. For example, a microorganism can be treated with or cultured in the presence of an agent known or suspected to increase transcription of a particular gene and/or translation of a particular gene product such that transcription and/or translation are enhanced or increased. Alternatively, a microorganism can be cultured at a temperature selected to increase transcription of a particular gene and/or translation of a particular gene product such that transcription and/or translation are enhanced or increased.

V. Culturing and Fermenting Recombinant Microorganisms

The term "culturing" includes maintaining and/or growing a living microorganism of the present invention (e.g., maintaining and/or growing a culture or strain). In one embodiment, a microorganism of the invention is cultured in liquid media. In another embodiment, a microorganism of the invention is cultured in solid media or semi-solid media. In a preferred embodiment, a microorganism of the invention is cultured in media (e.g., a sterile, liquid medium) comprising nutrients essential or beneficial to the maintenance and/or growth of the microorganism (e.g., carbon sources or carbon substrate, for example carbohydrate, hydrocarbons, oils, fats, fatty acids, organic acids, and alcohols; nitrogen sources, for example, peptone, yeast extracts, meat extracts, malt extracts, urea, ammonium sulfate, ammonium chloride, ammonium nitrate and ammonium phosphate; phosphorus sources, for example, phosphoric acid, sodium and potassium salts thereof; trace elements, for example, magnesium, iron, manganese, calcium, copper, zinc, boron, molybdenum, and/or cobalt salts; as well as growth factors such as amino acids, vitamins, growth promoters and the like).

Preferably, microorganisms of the present invention are cultured under controlled pH. The term "controlled pH" includes any pH which results in production of the desired product (e.g., pantoate and/or pantothenate). In one embodiment microorganisms are cultured at a pH of about 7. In another embodiment, microorganisms are cultured at a pH of between 6.0 and 8.5. The desired pH may be maintained by any number of methods known to those skilled in the art.

Also preferably, microorganisms of the present invention are cultured under controlled aeration. The term "controlled aeration" includes sufficient aeration (e.g., oxygen) to result in production of the desired product (e.g., pantoate and/or pantothenate). In one embodiment, aeration is controlled by regulating oxygen levels in the culture, for example, by regulating the amount of oxygen dissolved in culture media. Preferably, aeration of the culture is controlled by agitating the culture. Agitation may be provided by a propeller or similar mechanical agitation equipment, by revolving or shaking the cuture vessel (e.g., tube or flask) or by various pumping equipment. Aeration may be further controlled by the passage of sterile air or oxygen through the medium (e.g., through the fermentation mixture). Also preferably, microorganisms of the present invention are cultured without excess foaming (e.g., via addition of antifoaming agents).

Moreover, microorganisms of the present invention can be cultured under controlled temperatures. The term "controlled temperature" includes any temperature which results in production of the desired product (e.g., pantoate and/or pantothenate). In one embodiment, controlled temperatures include temperatures between 15° C. and 95° C. In another embodiment, controlled temperatures include temperatures between 15° C. and 70° C. Preferred temperatures are between 20° C. and 55° C., more preferably between 30° C. and 50° C.

Microorganisms can be cultured (e.g., maintained and/or grown) in liquid media and preferably are cultured, either continuously or intermittently, by conventional culturing methods such as standing culture, test tube culture, shaking culture (e.g., rotary shaking culture, shake flask culture, etc.), aeration spinner culture, or fermentation. In a preferred embodiment, the microorganisms are cultured in shake flasks. In a more preferred embodiment, the microorganisms are cultured in a fermentor (e.g., a fermentation process). Fermentation processes of the present invention include, but are not limited to, batch, fed-batch and continuous processes or methods of fermentation. The phrase "batch process" or "batch fermentation" refers to a system in which the composition of media, nutrients, supplemental additives and the like is set at the beginning of the fermentation and not subject to alteration during the fermentation, however, attempts may be made to control such factors as pH and oxygen concentration to prevent excess media acidification and/or microorganism death. The phrase "fed-batch process" or "fed-batch" fermentation refers to a batch fermentation with the exception that one or more substrates or supplements are added (e.g., added in increments or continuously) as the fermentation progresses. The phrase "continuous process" or "continuous fermentation" refers to a system in which a defined fermentation media is added continuously to a fermentor and an equal amount of used or "conditioned" media is simultaneously removed, preferably for recovery of the desired product (e.g., pantoate and/or pantothenate). A variety of such processes have been developed and are well-known in the art.

The phrase "culturing under conditions such that a desired compound is produced" includes maintaining and/or growing microorganisms under conditions (e.g., temperature, pressure, pH, duration, etc.) appropriate or sufficient to obtain production of the desired compound or to obtain desired yields of the particular compound being produced. For example, culturing is continued for a time sufficient to produce the desired amount of a compound (e.g., pantoate and/or pantothenate). Preferably, culturing is continued for a time sufficient to substantially reach suitable production of the compound (e.g., a time sufficient to reach a suitable concentration of pantoate and/or pantothenate or suitable ratio of pantoate and/or pantothenate:HMBPA). In one embodiment, culturing is continued for about 12 to 24 hours. In another embodiment, culturing is continued for about 24 to 36 hours, 36 to 48 hours, 48 to 72 hours, 72 to 96 hours, 96 to 120 hours, 120 to 144 hours, or greater than 144 hours. In yet another embodiment, microorganisms are cultured under conditions such that at least about 5 to 10 g/L of compound are produced in about 36 hours, at least about 10 to 20 g/L compound are produced in about 48 hours, or at least about 20 to 30 g/L compound in about 72 hours. In yet another embodiment, microorganisms are cultured under conditions such that at least about 5 to 20 g/L of compound are produced in about 36 hours, at least about 20 to 30 g/L compound are produced in about 48 hours, or at least about 30 to 50. or 60 g/L compound in about 72 hours. In another embodiment, microorganisms are cultured under conditions such that a ratio of HMBPA:HMBPA+pantothenate of 0.1:100 or less is achieved (i.e., 0.1% HMBPA versus 99.9% pantothenate, for example, as determined by comparing the peak areas when a sample of product is analyzed by HPLC), preferably such that a ratio of 0.2:100 or less is achieved (0.2% HMBPA versus 99.8% pantotheante), more preferably such that a ratio of 0.5:100 or less is achieved (0.5% HMBPA versus 99.5% pantotheante). In yet another embodiment, microorganisms are cultured under conditions such that a ratio of HMBPA:HMBPA+pantothenate of 1:100 or less is achieved (i. e., 1% HMBPA versus 99% pantothenate, for example, as determined by comparing the peak areas whena sample of product is analyzed be HPLC), preferably such that a ratio of 2:100 or less is achieved (2% HMBPA versus 98% pantotheante), more preferably such that a ratio of 3:100 or less is achieved (3% HMBPA versus 97% pantotheante), more preferably at least 4:100 or less (4% HMBPA versus 96% pantotheante), 5:100 or less (5% HMBPA versus 95% pantotheante), 6:100 or less (6% HMBPA versus 94% pantotheante), 7:100 or less (7% HMBPA versus 93% pantotheante), 8:100 or less (8% HMBPA versus 92% pantotheante), 9:100 or less (9% HMBPA versus 91% pantotheante), or 10:100 or less (10% HMBPA versus 90% pantotheante).

The methodology of the present invention can further include a step of recovering a desired compound (e.g., pantoate and.or pantothenate). The term "recovering" a desired compound includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), dialysis, filtration, concentration, crystallization, recrystallization, pH adjustment, lyophilization and the like. For example, a compound can be recovered from culture media by first removing the microorganisms from the culture. Media are then passed through or over a cation exchange resin to remove cations and then through or over an anion exchange resin to remove inorganic anions and organic acids having stronger acidities than the compound of interest. The resulting compound can subsequently be converted to a salt (e.g., a calcium salt) as described herein.

Preferably, a desired compound of the present invention is "extracted", "isolated" or "purified" such that the resulting preparation is substantially free of other media components (e.g., free of media components and/or fermentation byproducts). The language "substantially free of other media components" includes preparations of the desired compound in which the compound is separated from media components or fermentation byproducts of the culture from which it is produced. In one embodiment, the preparation has greater than about 80% (by dry weight) of the desired compound (e.g., less than about 20% of other media components or fermentation byproducts), more preferably greater than about 90% of the desired compound (e.g., less than about 10% of other media components or fermentation byproducts), still more preferably greater than about 95% of the desired compound (e.g., less than about 5% of other media components or fermentation byproducts), and most preferably greater than about 98–99% desired compound (e.g., less than about 1–2% other media components or fermentation byproducts). When the desired compound has been derivatized to a salt, the compound is preferably further free of chemical contaminants associated with the formation of the salt. When the desired compound has been derivatized to an alcohol, the compound is preferably further free of chemical contaminants associated with the formation of the alcohol.

In an alternative embodiment, the desired compound is not purified from the microorganism, for example, when the microorganism is biologically non-hazardous (e.g., safe). For example, the entire culture (or culture supernatant) can be used as a source of product (e.g., crude product). In one embodiment, the culture (or culture supernatant) is used without modification. In another embodiment, the culture (or culture supernatant) is concentrated. In yet another embodiment, the culture (or culture supernatant) is dried or lyophilized.

Preferably, a production method of the present invention results in production of the desired compound at a significantly high yield. The phrase "significantly high yield" includes a level of production or yield which is sufficiently elevated or above what is usual for comparable production methods, for example, which is elevated to a level sufficient for commercial production of the desired product (e.g., production of the product at a commercially feasible cost). In one embodiment, the invention features a production method that includes culturing a recombinant microorganism under conditions such that the desired product (e.g., pantoate and/or pantothenate) is produced at a level greater than 2 g/L. In another embodiment, the invention features a production method that includes culturing a recombinant microorganism under conditions such that the desired product (e.g., pantoate and/or pantothenate) is produced at a level greater than 10 g/L. In another embodiment, the invention features a production method that includes culturing a recombinant microorganism under conditions such that the desired product (e.g., pantoate and/or pantothenate) is produced at a level greater than 20 g/L. In yet another embodiment, the invention features a production method that includes culturing a recombinant microorganism under conditions such that the desired product (e.g., pantoate and/or pantothenate) is produced at a level greater than 30 g/L. In yet another embodiment, the invention features a production method that includes culturing a recombinant microorganism under conditions such that the desired product (e.g., pantoate and/or pantothenate) is produced at a level greater than 40 g/L. In yet another embodiment, the invention features a production method that includes culturing a recombinant microorganism under conditions such that the desired product (e.g., pantoate and/or pantothenate) is produced at a level greater than 50 g/L. In yet another embodiment, the invention features a production method that includes culturing a recombinant microorganism under conditions such that the desired product (e.g., pantoate and/or pantothenate) is produced at a level greater than 60 g/L. The invention further features a production method for producing the desired compound that involves culturing a recombinant microorganism under conditions such that a sufficiently elevated level of compound is produced within a commercially desirable period of time.

Depending on the biosynthetic enzyme or combination of biosynthetic enzymes manipulated, it may be desirable or necessary to provide (e.g., feed) microorganisms of the present invention at least one biosynthetic precursor such that the desired compound or compounds are produced. The term "biosynthetic precursor" or "precursor" includes an agent or compound which, when provided to, brought into contact with, or included in the culture medium of a microorganism, serves to enhance or increase biosynthesis of the desired product. In one embodiment, the biosynthetic precursor or precursor is aspartate. In another embodiment, the biosynthetic precursor or precursor is β-alanine. The amount of aspartate or β-alanine added is preferably an amount that results in a concentration in the culture medium sufficient to enhance productivity of the microorganism (e.g., a concentration sufficient to enhance production of pantoate and/or pantothenate). Biosynthetic precursors of the present invention can be added in the form of a concentrated solution or suspension (e.g., in a suitable solvent such as water or buffer) or in the form of a solid (e.g., in the form of a powder). Moreover, biosynthetic precursors of the present invention can be added as a single aliquot, continuously or intermittently over a given period of time. The term "excess β-alanine" includes β-alanine levels increased or higher that those routinely utilized for culturing the microorganism in question. For example, culturing the Bacillus microorganisms described in the instant Examples is routinely done in the presence of about 0–0.01 g/L β-alanine. Accordingly, excess β-alanine levels can include levels of about 0.01–1, preferably about 1–20 g/L.

In yet another embodiment, the biosynthetic precursor is valine. In yet another embodiment, the biosynthetic precursor is α-ketoisovalerate. Preferably, valine or α-ketoisovalerate is added in an amount that results in a concentration in the medium sufficient for production of the desired product (e.g., pantoate and/or pantothenate) to occur. The term "excess α-KIV" includes α-KIV levels increased or higher that those routinely utilized for culturing the microorganism in question. For example, culturing the *Bacillus* microorganisms described in the instant Examples is routinely done in the presence of about 0–0.01 g/L α-KIV. Accordingly, excess α-KIV levels can include levels of about 0.01–1, preferably about 1–20 g/L α-KIV. The term "excess valine" includes valine levels increased or higher that those routinely utilized for culturing the microorganism in question. For example, culturing the *Bacillus* microorganisms described in the instant Examples is routinely done in the presence of about 0–0.5 g/L valine. Accordingly, excess valine levels can include levels of about 0.5–5 g/L, preferably about 5–20 g/L valine. Biosynthetic precursors are also referred to herein as "supplemental biosynthetic substrates".

Another aspect of the present invention includes biotransformation processes which feature the recombinant microorganisms described herein. The term "biotransformation process", also referred to herein as "bioconversion processes", includes biological processes which results in the production (e.g., transformation or conversion) of appropriate substrates and/or intermediate compounds into a desired product (e.g., pantoate and/or pantothenate).

The microorganism(s) and/or enzymes used in the biotransformation reactions are in a form allowing them to perform their intended function (e.g., producing a desired compound). The microorganisms can be whole cells, or can be only those portions of the cells necessary to obtain the desired end result. The microorganisms can be suspended (e.g., in an appropriate solution such as buffered solutions or media), rinsed (e.g., rinsed free of media from culturing the microorganism), acetone-dried, immobilized (e.g., with polyacrylamide gel or k-carrageenan or on synthetic supports, for example, beads, matrices and the like), fixed, cross-linked or permeablized (e.g., have permeablized membranes and/or walls such that compounds, for example, substrates, intermediates or products can more easily pass through said membrane or wall).

VI Processes for the Production of Selectively Mixed Compositions of Pantothenate and HMBPA The present invention further features processes and microorganisms for the production of selectively mixed compositions of pantothenate and HMBPA. As defined herein, the phrase "selectively mixed composition" includes a composition produced in a manner such that the ratio of pantothenate to HMBPA is a controlled feature, i.e., the ratio of pantothenate to HMBPA is selected. The selection can occur by manipulating the microorganism producing the composition (i.e., the production strain) such that one component is favored for production over the other.

In one aspect, the invention features a process for the production of a selectively mixed pantothenate:HMBPA composition that includes culturing a microorganism having a deregulated pantothenate biosynthetic pathway under conditions such that a selectively mixed pantothenate:HMBPA composition is produced. In one embodiment, the microorganism is cultured under conditions that favor pantothenate production. In another embodiment, the microorganism is cultured under conditions that favor HMBPA production. In another embodiment, the microorganism is cultured under conditions of controlled steady state glucose that favor pantothenate production. In another embodiment, the microorganism is cultured under conditions of controlled steady state glucose that favor HMBPA production. In yet another embodiment, the microorganism is cultured under conditions of controlled steady state dissolved oxygen that favor pantothenate production. In yet another embodiment, the microorganism is cultured under conditions of controlled steady state dissolved oxygen that favor HMBPA production. In yet another embodiment, the microorganism is cultured under conditions of controlled serine levels that favor pantothenate production. In one embodiment, the composition comprises pantothenate and HMBPA at a ratio of 75 mol pantothenate to 25 mol HMBPA or greater. In another embodiment, the composition comprises pantothenate and HMBPA at a ratio of 90 mol pantothenate to 10 mol HMBPA or greater. In another embodiment, the composition comprises pantothenate and HMBPA at a ratio of 75 mol HMBPA to 25 mol pantothenate or greater. In yet another embodiment, the composition comprises pantothenate and HMBPA at a ratio of 90 mol HMBPA to 10 mol pantothenate or greater. Values and ranges included and/or intermediate of the values set forth herein are also intended to be within the scope of the present invention.

This invention is further illustrated by the following examples which should not be construed as limiting. The contents of all references, patents and published patent applications cited throughout this application are incorporated herein by reference.

EXAMPLES

Example I

Discovery and Characterization of the [R]-3-(2-hydroxy-3-methyl-butyrylamino)-propionic acid (HMBPA) Biosynthetic Pathway In developing *Bacillus* strains for the production of pantothenate, various genetic manipulations are made to genes and enzymes involved in the pantothenate biosynthetic pathway and the isoleucine-valine (ilv) pathway (FIG. 1) as described in U.S. patent application Ser. No. 09/400,494 and U.S. patent application Ser. No. 09/667,569. For example, strains having a deregulated panBCD operon and/or having deregulated panE1 exhibit enhanced pantothenate production (when cultured in the presence of β-alanine and α-ketoisovalerate (α-KIV)). Strains further deregulated for ilvBNC and ilvD exhibit enhanced pantothenate production in the presence of only β-alanine. Moreover, it is possible to achieve β-alanine independence by further deregulating panD.

An exemplary strain is PA824, a tryptophan prototroph, Spec and Tet resistant, deregulated for panBCD at the panBCD locus, deregulated for panE1 at the panE1 locus (two genes in the *B. subtilis* genome are homologous to *E. coli* panE, panE1 and pan2, the former encoding the major ketopantoate reductase involved in pantothenate production, while panE2 does not contribute to pantothenate synthesis (U.S. patent application Ser. No. 09/400,494), deregulated for ilvD at the ilvD locus, overexpressing an ilvBNC cassette at the amyE locus, and overexpressing panD at the bpr locus.

Under the following fermentation conditions, PA824 routinely yields approximately 20–30 g/L pantothenate. The production of pantothenate by PA824 in this example is accomplished in 14 L fermentor vessels. The composition of the batch and feed media are as follows.

| | BATCH | |
|---|---|---|
| | MATERIAL | g/L (final) |
| 1 | Yeast extract | 10 |
| 2 | Na Glutamate | 5 |
| 3 | $(NH_4)_2SO_4$ | 8 |
| 4 | $KH_2PO_4$ | 5 |
| 5 | $K_2HPO_4$ | 7.6 |
| | Added After Sterilization and Cool Down | |
| 1 | Glucose | 2.5 |
| 2 | $CaCl_2$ | 0.1 |
| 3 | $MgCl_2$ | 1 |
| 4 | Sodium Citrate | 1 |
| 5 | $FeSO_4 \cdot 7\ H_2O$ | 0.01 |
| 5 | SM-1000X | 1 ml |

The final volume of the batch medium is 6 L. The trace element solution SM-1000X has following composition: 0.15 g $Na_2MoO_4.2\ H_2O$, 2.5 g $H_3BO_3$, 0.7 g $CoCl_2.6\ H_2O$, 0.25 g $CuSO_4.5\ H_2O$, 1.6 g $MnCl_2.4\ H_2O$, 0.3 g $ZnSO_4.7\ H_2O$ are dissolved in water (final volume 1 L).

The batch medium was inoculated with 60 ml of shake flask PA824 culture (OD=10 in SVY medium: Difco Veal Infusion broth 25 g, Difco Yeast extract 5 g, Sodium Glutamate 5 g, $(NH_4)_2SO_4$ 2.7 g in 740 ml $H_2O$, autoclave; add 200 ml sterile 1 M $K_2HPO_4$ (pH 7) and 60 ml sterile 50% Glucose solution (final volume 1L)). The fermentation was run at 43° C. at an air flow rate of 12 L/min as a glucose limited fed batch. The initial batched glucose (2.5 g/L) was consumed during exponential growth. Afterwards glucose concentrations were maintained between 0.2–1 g/L by continuous feeding of FEED solution as follows.

| | FEED | |
|---|---|---|
| | MATERIAL | g/L (final) |
| 1 | Glucose | 550 |
| 2 | $CaCl_2$ | 0.1 |
| 3 | SM-1000X | 3 ml |

The variable feed rate pump was computer controlled and linked to the glucose concentration in the tank by an algorithm. In this example the total feeding was 6 L.

During fermentation the pH was set at 7.2. Control was achieved by pH measurements linked to computer control. The pH value was maintained by feeding either a 25% $NH_3$-solution or a 20% $H_3PO_4$-solution. $NH_3$ acts simultaneously as a N-source for the fermentation. The dissolved oxygen concentration [$pO_2$] was set at 30% by regulation of the agitation and aeration rate. Foaming was controlled by addition of silicone oil. After the stop of the addition of the feed solution, in this example after 48 hours, the fermentation was continued until the [$pO_2$] value reached 95%. Then the fermentation was stopped by killing the microorganism through sterilization for 30 min. The successful sterilization was proven by plating a sample of the fermentation broth on agar plates. The pantothenate titer in the fermentation broth was 21.7 g/L after sterilization and removal of the cells by centrifugation (determined by HPLC analysis).

For HPLC analysis the fermentation broth sample was diluted with sterile water (1:40). 5 µl of this dilution was injected into a HPLC column (Aqua C18, 5 µm, 150×2.0 mm, Phenomenex™). Temperature of the column was held at 40° C. Mobile phase A was 14.8 mM $H_3PO_3$, mobile phase B 100% Acetonitrile. Flow rate was constant at 0.5 mL/min. A gradient was applied:

| start: | 2% mobile phase B |
|---|---|
| 0–3 min | linear increase to 3% mobile phase B |
| 3–3.5 min | linear increase to 20% mobile phase B |

Figure 4:
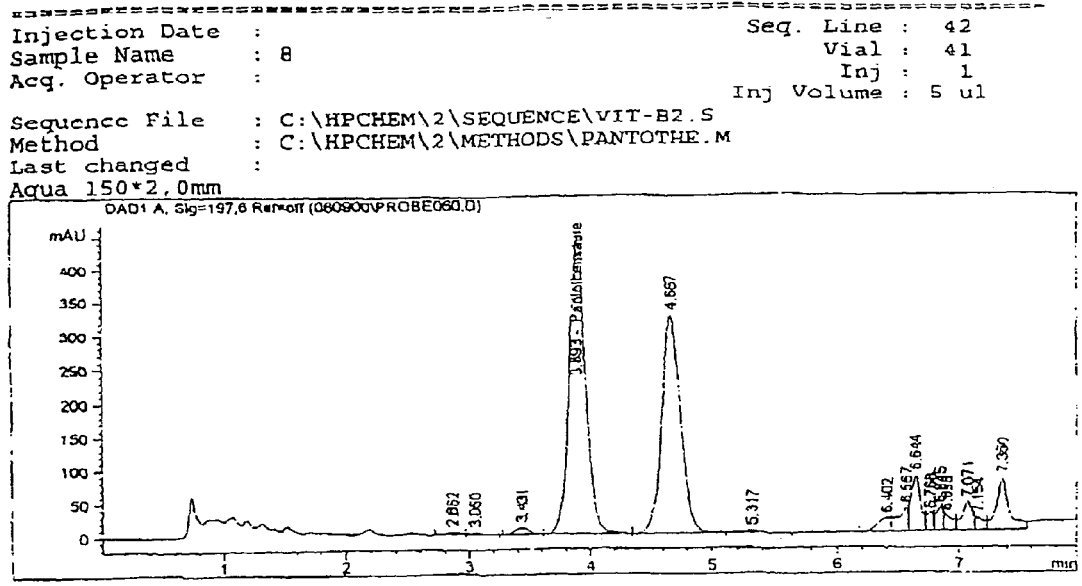
FIG. 4 is a HPLC chromatogram of a sample of medium from a 14 L fermentation of PAS24.

The detection was carried out by an UV-detector (210 nm). Run time was 7 min with an additional 3 min posttime. The retention time for pantothenic acid is 3.9 minutes. The HPLC chromatogram for the above mentioned sample is given in FIG. 4.

Identification of a Compound Related to the Peak with Retention Time 4.7 Minutes In addition to producing significant quantities of pantothenate, it was discovered a second compound eluted with an approximate retention time of 4.7 minutes in this system. The second prominent product formed in the fermentation was shown to be 3-(2-hydroxy-3-methyl-butyrylamino)-propionic acid (HMBPA) (also referred to herein as "β-alanine 2-(R)-hydroxyisolvalerate", "β-alanine 2-hydroxyisolvalerate", "β-alanyl-α-hydroxyisovalarate" and/or "fantothenate"). It was identified by its mass spectrum (FIG. 5; relative monoisotopic mass 189), and by $^1$- and 13C-NMR after chromatographic purification by reverse phase flash chromatography (mobile phase 10 mM $KH_2PO_4$, with increasing contents of acetonitrile (1–50%)) (data not shown). The compound was presumed to have the R configuration at the assymetric carbon by analogy with [R]-pantothenate.

In order to verify the identity of the compound, deliberate synthesis of racemic β-alanine 2-hydroxyisolvalerate was preformed as follows. β-alanine (2.73 g/30 mmol) and sodium methoxide (5.67 g of a 30% solution in methanol/ 31.5 mmol) were dissolved in methanol (40 mL). Methyl 2-hydroxyisovalerate (2-hydroxy-3-methylbutyric acid methyl ester) (3.96 g/30 mmol) was added and refluxed for 18 hours. Methanol was then removed by rotavap and replaced by tert-butanol (50 mL). Potassium tert-butoxide was added (50 mg) and refluxed for 26 hours. The solvent was removed in vacuo, the residue dissolved in water (50 mL) and passed through a strongly acidic ion-exchange resin (H+-form Lewatite™ S 100 G1; 100 mL). More water is used to rinse the ion exchanger. The aqueous eluates are combined and the water removed in vacuo. The residue is subjected to flash chromatography (silica gel; 2% acetic acid in ethyl acetate as eluent) and the product fractions evaporated to give a solid residue. The residue was recrystallized from ethyl acetate/toluene (10 mL/20 mL, respectively) and analytically pure HMBPA (β-alanine 2-hydroxyisolvalerate) was obtained, which showed a relative monoisotopic mass of 190 (189+H$^+$) in the mass spectrometer and the same $^1$H-NMR resonances as the product obtained from fermentation.

Figure 2:
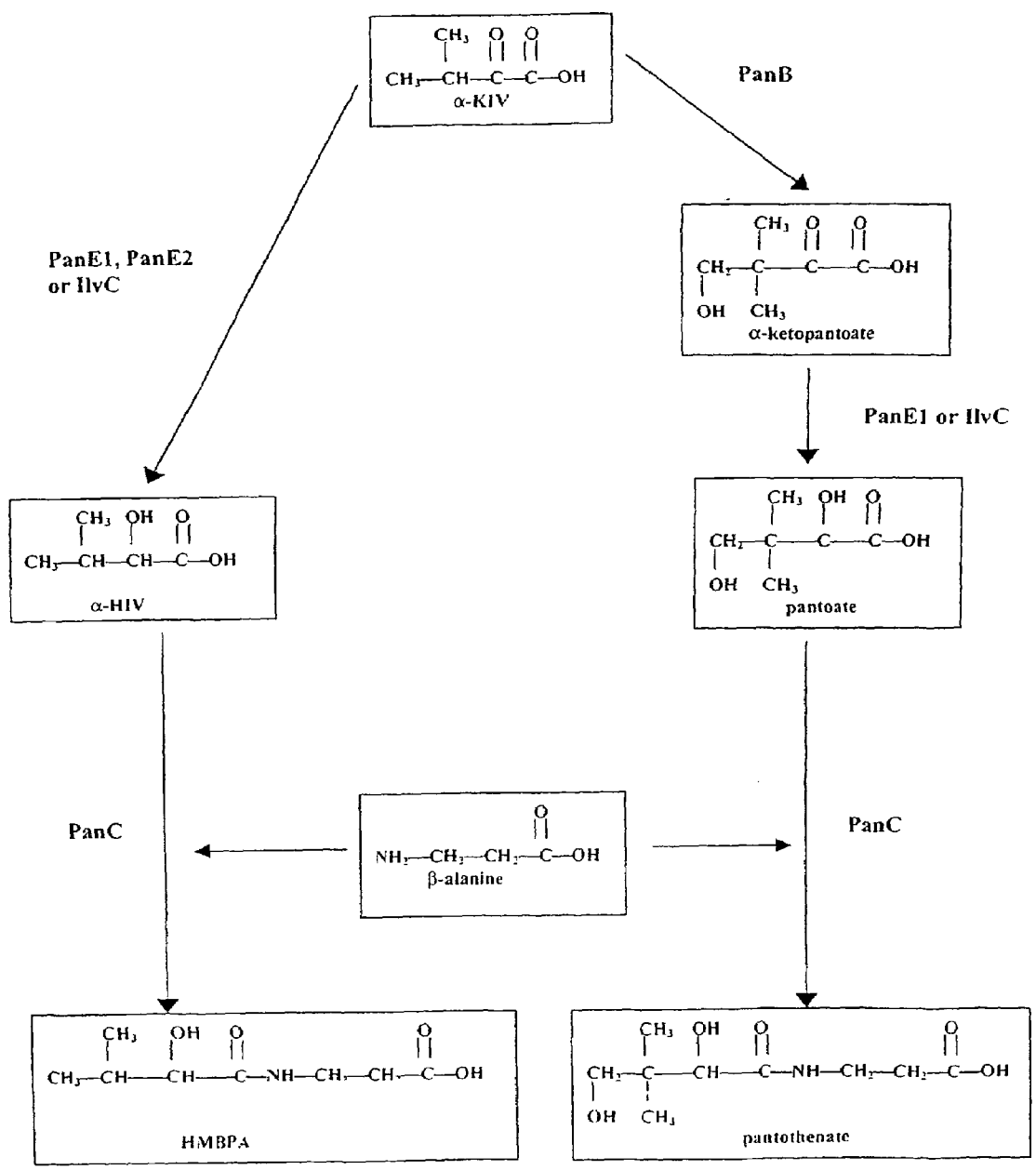
FIG. 2 is a schematic representation of the biosynthetic pathway leading to the formation [R]-3-(2-hydroxy-3-methyl-butyrylamino)-propionic acid ("HMBPA") in *B. subtilis*.
Figure 3:
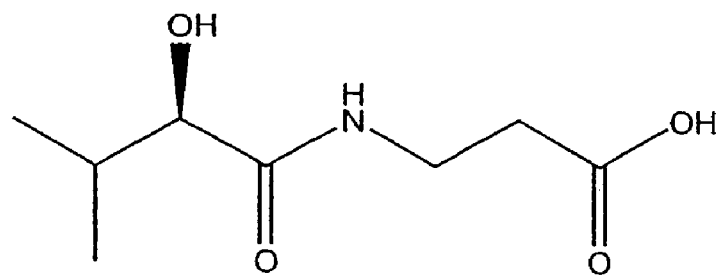
FIG. 3 is a schematic depiction of the structure of [R]-3-(2-hydroxy-3-methyl-butyrylamino)-propionic acid ("HMBPA").

The biosynthetic pathway resulting in HMBPA production is set forth in FIG. 2. The chemical structure of [R]-3-(2-hydroxy-3-methyl-butyrylamino)-propionic acid (HMBPA) is depicted in FIG. 3. As depicted in FIG. 2, HMBPA is the condensation product of [R]-α-hydroxyisovaleric acid (α-HIV) and β-alanine, catalyzed by the PanC enzyme. α-HIV is generated by reduction of α-KIV, a reaction that is catalyzed by the α-keto reductases PanE (e.g., PanE1 and/or PanE2) and/or IlvC.

Based on the chemical structure and biosynthetic pathway leading to HMBPA production, the present inventors have formulated the following model to describe the interaction between the previously known pantothenate and isoleucine-valine (ilv) pathways and the newly characterized HMBPA biosynthetic pathway. In at least one aspect, the model states that there exist at least two pathways in microorganisms that compete for α-KIV, the substrate for the biosynthetic enzyme PanB, namely the pantothenate biosynthetic pathway and the HMBPA biosynthetic pathway. (A third and fourth pathway competing for α-KIV are those resulting in the production of valine or leucine from α-KIV, see e.g., FIG. 1). At least the pantothenate biosynthetic pathway and the HMBPA biosynthetic pathway further produce competitive substrates for the enzyme PanC, namely α-HIV and pantoate. Production of HMBPA hassignificant effects on pantothenate production. Most importantly, the HMBPA pathway competes with the pantothenate pathway for precursors (α-KIV and β-alanine) and for some of the enzymes (PanC, PanD, PanE1, and/or IlvC). In addition, because the structure of HMBPA is similar to that of pantothenate, it may have the undesirable property of negatively regulating one or more steps in the pantothenate pathway. The model predicts that production of pantothenate can be improved or optimized by any means which favor use of substrates (α-KIV and β-alanine) and/or enzymes (PanC, PanD, PanE1, and/or IlvC) in pantothenate biosynthetic processes as compared to HMBPA biosynthetic processes.

A preferred approach to maximize pantoate and/or pantothenate production while minimizing HMBPA production is to increase the activity of PanB in the cells because this will decrease the availability of α-KIV for α-HIV synthesis while promoting the synthesis of ketopantoate and pantoate. Methods of increasing activity include overexpressing the panB gene, increasing the copy number of the gene, increasing the specific activity of the enzyme and/or relieving inhibition of the enzyme by mutation or by lowering Coenzyme A levels. Higher pantoate levels in turn increase pantothenate synthesis and decrease HMBPA synthesis by out competing α-HIV for PanC.

Another approach to maximize pantothenate synthesis is to optimize the level of panE1 expression. It is demonstrated herein that increasing production of PanE1 increases the synthesis of HMBPA at the expense of pantothenate. Accordingly, effecting a moderate decrease in the level of panE1 expression in PA824 or PA668 (i e., precisely regulating the level of panE1 expression) will result in a decrease in HMBPA synthesis and an increase in pantothenate synthesis. Moreover, as shown in Example II, deletion of panE2 significantly decreases HMBPA synthesis.

Other approaches to increasing pantoate and/or pantothenate synthesis versus HMBPA synthesis include optimizing α-KIV production levels in the cells and/or isolating a modified PanC protein with increased preference for pantoate as a substrate.

The following examples provide experimental support for the model described herein and further exemplify processes for increasing the production of pantoate and/or pantothenate (relative to HMBPA levels) based on the model.

Examples II–VIII

For Examples II–VI, quantitation of pantothenate and/or HMBPA was performed as follows. Aliquots of fermentation media were diluted 1:100 and aliquots of test tube cultures were diluted 1:10 in water or 5% acetonitrile prior to injection on a Phenomenex Aqua™ 5 μC18 HPLC column (250×4.60 mm, 125A). Mobile phases were A=5% acetonitrile, 50 mM monosodium phosphate buffer adjusted to pH 2.5 with phosphoric acid; and B=95% acetonitrile, 5% $H_2O$.

Linear gradients were as follows.

| Minutes | Solvent A | Solvent B |
|---|---|---|
| 0 | 100% | 0% |
| 16 | 100% | 0% |
| 17 | 0% | 100% |
| 20 | 0% | 100% |
| 21 | 100% | 0% |

Additional parameters and apparatus were as follows: Flow rate=1.0 ml/min; Injection volume=20 μl; Detector=Hewlett Packard 1090 series DAD UV detector-3014, Signal A=197 nm, ref.=450 nm, Firmware revision E; Column heater=Oven temperature 40° C.; Hardware=Hewlett Packard Kayak™ XA; and Software=Hewlett Packard Chemstation Plus™ family revision A.06.03[509].

HMBPA elutes at approximately 13 minutes in this system.

Example II

Decreasing HMBPA Synthesis by Deleting PanE2 from Pantothenate Production Strains As described in Example I, HMBPA production was first observed in microorganisms overexpressing panE1 indicating that ketopantoate reductase is capable of catalyzing not only the reduction of ketopantoate to pantoate but also the reduction of α-ketoisovalerate to 2-hydroxyisovalerate. As mentioned previously, two genes in the B. subtilis genome are homologous to the E. coli panE gene encoding ketopantoate reductase and have been named panE1 and panE2. In Bacillus, it has been demonstrated that the panE1 gene encodes the major ketopantoate reductase involved in pantothenate production, whereas panE2 does not contribute to pantothenate synthesis. Moreover, overexpression of panE2 from a $P_{26}$panE2 cassette in pAN238 (SEQ ID NO:25) leads to a reduction in pantothenate titer (see e.g., U.S. patent application Ser. No. 09/400,494). Given the homology between the panE2 and panE1 gene products and the fact that overexpression of panE2 shifted production away from pantoate/pantothenate, it was tested whether panE2 contributed in any significant manner to the production of HMBPA. It was hypothesized that the panE2 gene product is an enzyme capable of reducing α-KIV to α-HIV, but incapable of significantly reducing ketopantoate to pantoate.

To test the hypothesis, panE2 was deleted from pantothenate production strain PA824 (described in Example I) by transforming with a ΔpanE2::cat cassette from chromosomal DNA of strain PA248 (ΔpanE2::cat) (set forth as SEQ ID NO:24, for construction see e.g., U.S. patent application Ser. No. 09/400,494) to give strain PA919. Three isolates of PA919 were compared to PA824 for pantothenate and HMBPA production in test tube cultures grown in SVY plus β-alanine.

TABLE 1

Production of pantothenate and HMBPA by derivatives of PA824 and PA880 grown at 43° C. in 48 hour test tube cultures of SVY glucose + β-alanine[5].

| Strain | new trait | parent | $OD_{600}$ | [pan] g/l | [HMBPA] g/l |
|---|---|---|---|---|---|
| PA824 | — | | 13.9 | 4.3 | 0.64 |
| PA880 | ΔcoaX | PA824 | 16.4 | 5.1 | 0.48 |
| PA894 | ΔcoaX, coaA(S151L), cat | PA880 | 14.9 | 4.9 | 0.47 |
| PA911-5 | $P_{26}$panB @ vpr, ΔcoaX | PA880 | 13.4 | 5.3 | 0.40 |
| PA911-8 | $P_{26}$panB @ panB, ΔcoaX | " | 13.8 | 6.1 | 0.45 |
| PA919-1 | ΔpanE2::cat | PA824 | 13.2 | 4.2 | 0.15 |
| PA919-2 | " | " | 14.8 | 3.8 | 0.13 |
| PA919-3 | " | " | 18.0 | 5.5 | 0.14 |

As indicated by the data in Table 1, all three isolates of PA919 produced about four-fold lower HMBPA than PA824 demonstrating that the panE2 gene product contributed to HMBPA production and demonstrating that HMBPA production can be at least partially eliminated by simply deleting panE2, without sacrificing pantothenate production.

Example III

HMBPA Production and Pantothenate Production are Inversely Correlated

Strains derived from PA365 (the RL-1 lineage equivalent of PA377, described in U.S. patent appleation Ser. No. 09/667,569) which are deleted for the $P_{26}$ panBCD cassette and which contain a $P_{26}$panC*D cassette amplified at the vpr locus and either the wild type $P_{26}$panB cassette (PA666) or a $P_{26}$ ΔpanB cassette (PA664) amplified at the bpr locus were constructed as follows. An alignment of the C-terminal amino acids of known or suspected PanB proteins is shown in FIG. 6. Three regions called 1, 2 and 3 were identified having conserved or semi-conserved amino acid residues that are indicated by arrows at the top of the figure. The *B. subtilis* PanB protein (RBS02239) is underlined. Two of the PanB proteins (RCY14036 and CAB56202.1) are missing region 3 while the latter PanB protein is also missing region 2 and has non-conserved amino acid residues occupying region 1.

*B. subtilis* PanB variants were created that were missing regions 1, 2 and 3. The desired variants were created by designing 3' PCR primers to amplify the *B. subtilis* pan B gene such that region 3, regions 2 and 3, or all three regions would be missing from the final product. The PCR products were generated and cloned into *E. coli* expression vector pASK-1BA3, creating plasmids pAN446, pAN447, and pAN448, respectively. The plasmids were then transformed into *E. coli* strain SJ2 that contains the panB6 mutation to test for complementation. Only pAN446, which is missing region 3, was able to complement. This indicates that region 3 is not essential for *B. subtilis* PanB activity but that region 2 is required for activity or stability.

The next step in this analysis was to transfer the panB gene from pAN446 to a *B. subtilis* expression vector and then introduce it into a strain appropriate for testing activity of the encoded PanB protein in *B. subtilis*. To do this, a strain that is deleted for the $P_{26}$panBCD operon was first created. This was accomplished by first inserting a cat gene between the BseRI site located just upstream of the panB RBS and the Bg/II site located in panD, creating plasmid pAN624, SEQ ID NO:20 (FIG. 7).

The resulting deletion-substitution mutation (ΔpanBCD::cat624), which removes all of panB and panC, was crossed into PA354 by transformation, with selection for resistance to chloramphenicol on plates supplemented with 1 mM pantothenate. One of the transformants was saved and named PA644. Chromosomal DNA isolated from PA644 was analyzed by PCR and was shown to contain the deletion-substitution mutation. As expected, PA644 requires pantothenate for growth but retains the engineered ilv genes ($P_{26}$ilvBNC $P_{26}$ilvD) as well as the $P_{26}$pan E1 gene originally present in PA354. Thus, it has all the enzymes involved in pantoate synthesis overproduced except PanB. The gene containing the shortest panB deletion was inserted into *B. subtilis* expression vector pOTP61 (described in U.S. patent application Ser. No. 09/667,569), creating plasmid pAN627. At the same time, a wild-type panB control gene was inserted into pOTP61, creating plasmid pAN630. The NotI fragments of each plasmid, lacking *E. coli* vector sequences, were ligated and transformed into PA644, with selection for resistance to tetracycline.

One transformant from each transformation was saved and further transformed with chromosomal DNA from PA628 with selection for Pan⁺. PA628 contains a multicopy $P_{26}$panC*D expression plasnmid (pAN620) integrated at the vpr locus. In order to determine the effects of the panB gene mutation directly on pantothenate production, plasmid pAN620 SEQ ID NO:21, which is illustrated in FIG. 8, provides the remaining two enzymes required for pantothenate synthesis (PanC and PanD). Four transformants from each transformation were isolated, grown in SVY medium containing 10 g/L aspartate for 48 hours, then assayed for pantothenate production. Transformants with the 3' deleted panB gene were named PA664 and those containing the wild-type gene were called PA666. The data showed that the 3' deleted panB gene in PA664 encodes a PanB protein with greatly reduced activity. To test for HMBPA production, test tube cultures of PA365, PA666, and PA664 were grown in SVY+aspartate medium with and without added α-KIV or pantoate for 48 hours and then assayed for HMBPA and pantothenate as described previously.

TABLE 2

Effect of PanB activity and addition of precursors on HMBPA and pantothenate production, 48 hour test tube culture data, SVY + aspartate (10 g/L) medium.

| Strain | pan operon | panC*D plasmid | panB plasmid | no additions | | +α-KIV (5 g/L) | | +pantoate (5 g/L) | |
|---|---|---|---|---|---|---|---|---|---|
| | | | | [pan] (g/L) | HMBPA peak* | [pan] (g/L) | HMBPA peak | [pan] (g/L) | HMBPA peak |
| PA365 | $P_{26}$panBCD | NONE | NONE | 3.0 | 0.71 | 3.2 | 1.28 | 4.8 | 0.38 |
| PA666 | ΔpanBCD::cat | pAN620 | pAN630 | 3.7 | 0.55 | 3.3 | 1.70 | 5.2 | 0.26 |
| PA664 | ΔpanBCD::cat | pAN620 | pAN627 | 0.3 | 1.39 | 0.6 | 1.76 | 2.5 | 0.74 |

*HMBPA peak = peak area X $10^{-3}$

The data presented in Table 2 demonstrate that in the absence of supplements, PA666 produced the least HMBPA whereas PA664 produced the most, indicating an inverse correlation between PanB activity and HMBPA production. This is consistent with the model which predicts that the two pathways compete for α-KIV, the substrate for PanB, and produce competitive substrates for PanC; lowering PanB activity would be expected to increase α-KIV availability for α-HIV synthesis and correspondingly decrease the amount of pantoate synthesized. When α-KIV is added to the medium, all three strains produced significantly more HMBPA. This result implies that α-KIV is a precursor to HMBPA, as described in FIG. 2, anid that excess α-KIV favors HMBPA production. This result also suggests that synthesis of HMBPA is at least partially due to an overflow effect of excess α-KIV production. When pantoate was added to the medium, HMBPA was reduced by roughly 50 percent in all three strains. Conversely, the strains each produced significantly more pantothenate. This result is also consistent with the model that the two pathways produce competing substrates for PanC (α-HIV and pantoate). Taken together the above results further indicate that increasing pantoate synthesis should be beneficial in promoting pantothenate production as well as reducing HMBPA levels. Moreover, factors that decrease pantoate synthesis negatively affect pantothenate synthesis.

Example IV

Effect of Increasing PanB and/or Regulating PanE1 on Production of Pantothenate

PA668 is a derivative of PA824 that contains extra copies of $P_{26}$panB amplified at the vpr or panB locus. PA668 was constructed using the panB expression vector (pAN636, SEQ ID NO:22) which allows for selection of multiple copies using chloramphenicol (FIG. 9). The pAN636 NotI restriction fragment, missing the *E. coli* vector sequences, was ligated and then used to transform PA824 with selection on plates containing 5 μg/ml chloramphenicol. Transformants resistant to 30 μg/ml chloramphenicol were isolated and screened for pantothenate production in 48 hour test tube cultures. The isolates shown produce less HMBPA that PA824 (conversely producing about 10 percent more pantothenate than PA824). A second strain, called PA669, was constructed which is PA824 with extra copies of $P_{26}$panE1 amplified at the vpr or panE1 locus. Strain PA669 was constructed by transforming PA824 with the self-ligated NotI fragment of plasmid pAN637, SEQ ID NO:23 (FIG. 10) with selection for resistance to chloramphenicol. Two isolates of PA669 were chosen for further study; PA669-5 produces less PanE1 than PA669-7 as judged by SDS-PAGE analysis of total cell extracts made from the two strains.

Test tube cultures of strains PA824, PA668-2, PA668-24, and the two isolates of PA669 (PA669-5 and PA669-7) were grown in three different media (SVY, SVY+aspartate, and SVY+aspartate+pantoate) for 48 hours and then assayed for pantothenate, HMBPA, and β-alanine (Table 3).

that the strain that produces the most PanE1 (PA669-7) produced the most HMBPA (and the least pantothenate). This suggests that high levels of PanE1 favor the production of HMBPA at the expense of lower pantothenate synthesis. It is also interesting that PA668-24 produced more HMBPA than PA668-2, even though SDS-PAGE analysis of extracts from the two strains showed that they produce roughly equivalent levels of PanB. The SDS-PAGE analysis also showed that PA668-24 makes much more IlvC than PA668-2. Based on these data, it is proposed that IlvC influences HMBPA synthesis by increasing steady state levels of α-KIV and/or by catalyzing α-HIV formation from α-KIV, thereby accounting for the observed shift towards production of HMBPA.

The final set of data in Table 3 shows that adding pantoate to the growth medium decreased HMBPA production by all strains that had previously produced detectable levels, e.g., by shifting synthesis towards pantothenate. This further supports the model that α-HIV and pantoate are competitive substrates for PanC.

Example V

Increasing Pantothenate Synthesis by Reduction of Pantothenate Kinase in Production Strains One strategy to increase pantothenate production is to reduce the amount of pantothenate kinase activity in production strains. Pantothenate kinase is the first enzyme in the pathway from pantothenate to Coenzyme A. It was hypothesized that lower pantothenate kinase activity would lead to lower steady state levels of Coenzyme A, which could in turn lead to higher PanB enzyme activity and higher titers of pantothenate. As described in U.S. patent application Ser. No. 09/667,569, two unlinked genes have been identified in *B. subtilis* that both encode pantothenate kinase, 1) coaA, which is homologous to the essential *E. coli* pantothenate kinase gene, and 2) coaX, which represents a novel class of bacterial pantothenate kinase genes.

TABLE 3

Effect of extra copies of panB and panE1 on pantothenate and HMBPA production by PA824, 48 hour test tube culture data, SVY medium.

| Strain | panB plasmid | panE plasmid | no additions | | | +aspartate (10 g/L) | | | +aspartate (10 g/L) & pantoate (5 g/L) | | |
|---|---|---|---|---|---|---|---|---|---|---|---|
| | | | [pan] (g/L) | [β-ala] (g/L) | HMBPA * | [pan] (g/L) | [β-ala] (g/L) | HMBPA | [pan] (g/L) | [β-ala] (g/L) | HMBPA |
| PA824 | NONE | NONE | 1.8 | 0.05 | <0.1 | 4.7 | 2.5 | 0.53 | 5.6 | 2.5 | <0.10 |
| PA668-2 | pAN636 | NONE | 1.5 | <0.04 | <0.1 | 5.0 | 1.6 | <0.10 | 4.9 | 1.2 | <0.10 |
| PA668-24 | pAN636 | NONE | 1.8 | 0.05 | <0.1 | 4.9 | 2.8 | 0.34 | 6.1 | 2.6 | <0.10 |
| PA669-5 | NONE | pAN637 | 1.8 | 0.04 | <0.1 | 4.2 | 3.1 | 0.74 | 5.8 | 2.6 | 0.30 |
| PA669-7 | NONE | pAN637 | 1.8 | 0.06 | <0.1 | 3.7 | 3.2 | 1.41 | 5.2 | 2.5 | 0.75 |

*HMBPA = peak area X $10^{-3}$

None of the strains produced detectable quantities of HMBPA in SVY medium. All strains produced roughly equivalent amounts of pantothenate and low amounts of β-alanine indicating that β-alanine is limiting for both pantothenate and HMBPA synthesis in these cultures and that β-alanine is a precursor for both compounds. When grown in SVY+aspartate medium, the two PA669 isolates produced more HMBPA than PA824 whereas both PA668 isolates produced less HMBPA than PA824. It is noteworthy Either coaA or coaX can be deleted from a wild type *B. subtilis* strain without any apparent effect on growth on rich or minimal medium. However, it is not possible to generate strains having a deletion in both genes, suggesting that one or the other is necessary for viability. Therefore, a strain was constructed having a deleted coaX and then coaA was mutated to reduce the specific activity of the CoaA enzyme. Although the phenotypes of the ΔcoaX, mutated coaA strains are subtle, the data is consistent with the hypothesis that PanB activity can be increased by restricting pantothenate kinase activity. This in turn decreases HMBPA production and increases pantothenate production.

Installation of ΔcoaX and Mutated coaA Alleles into PA824.

Deletion of coaX from PA824 was accomplished in a single step by transforming PA824 to kanamycin resistance with chromosomal DNA from PA876 (PY79 ΔcoaX::kan), described in U.S. patent application Ser. No. 09/667,569, to give PA880. The caaX deletion in PA880 and PA876 was derived ultimately from plasmid pAN336 (SEQ ID NO:26, see U.S. patent application Ser. No. 09/667,569). Next, a control version of a wild type coaA gene and two mutated alleles of coaA were introduced as follows. The control and two mutated alleles were first introduced into the chromosome of wild type strain $PY_{79}$ using transformation to chloramphenicol resistance by plasmids, and then chromosomal DNA from these intermediate strains was used to transform PA880 to chloramphenicol resistance. The plasmids used to integrate the control and mutant alleles were pAN294 (SEQ ID NO:27, see U.S. patent application Ser. No. 09/667,569), pAN34A, and pAN344. pAN343 is almost identical to pAN294, except that it contains a T to C base change at base number 3228 of pAN294. Similarly, pAN344 has a CC to TA change at base numbers 3217 and 3218 of pAN294. All three plasmids have a chloramphenicol resistance gene (cat) substituting for the dispensable gene of unkown funtion, yqjT, that lies just downstrean from coaA. The intermediate strains derived from PY79 by double crossovers of pAN294 (wild type coaA, yqjT::cat), pAN343 (coaA2 Y155H, yqjT::cat), and pAN344 (coaA2 S151L, yqjT::cat), are named PA886, PA887, and PA888, repectively. Next, PA880 was transformed to chloramphenicol resistance with chromosomal DNA from PA886, PA887, or PA888, to give strains PA892 (wild type coaA, cat), PA893 (coaA Y155H, cat), and PA894 (coaA S151 L, cat), respectively. Eight candidates for PA893 were checked for acquisition of the Y155H mutation by PCR of the coaA gene and NlaIII digestion, and all eight were correct.

Several candidates for each new strain, including PA880, were assayed for pantothenate production at 43° in standard test tube cultures grown in SVY medium plus 5 g/l β-alanine (see Table 4).

TABLE 4

Production of pantothenate and fantothenate by derivatives of PA824 that have been deleted for coaX and mutated for coaA, grown at 43° C. in 48 hour test tube cultures of SVY glucose + β-alanine.

| Strain | coaA | coaX | $OD_{600}$ | [pan] g/l | [HMBPA] g/l |
|---|---|---|---|---|---|
| PA824 | wt | wt | 11.1 | 4.4 | 0.77 |
| PA824 | wt | wt | 11.4 | 4.1 | 0.70 |
| PA880 | wt | Δ | 11.6 | 5.5 | 0.33 |
| PA880 | wt | Δ | 12.7 | 5.1 | 0.33 |
| PA892-1 | wt, cat | Δ | 11.7 | 4.5 | 0.26 |
| PA892-2 | wt, cat | Δ | 13.4 | 4.5 | 0.26 |
| PA892-3 | wt, cat | Δ | 12.9 | 4.8 | 0.25 |
| PA893-1 | Y155H, cat | Δ | 10.7 | 4.3 | 0.24 |
| PA893-2 | Y155H, cat | Δ | 12.0 | 4.5 | 0.25 |
| PA893-3 | Y155H, cat | Δ | 11.9 | 4.7 | 0.23 |
| PA893-4 | Y155H, cat | Δ | 12.8 | 4.3 | 0.20 |
| PA893-5 | Y155H, cat | Δ | 11.6 | 4.7 | 0.28 |
| PA893-8 | Y155H, cat | Δ | 10.0 | 4.7 | 0.25 |
| PA894-1 | S151L ?, cat | Δ | 11.6 | 4.6 | 0.29 |
| PA894-2 | S151L ?, cat | Δ | 15.6 | 4.5 | 0.27 |
| PA894-3 | S151L ?, cat | Δ | 12.3 | 5.0 | 0.31 |
| PA894-4 | S151L ?, cat | Δ | 12.2 | 5.0 | 0.27 |
| PA894-5 | S151L ?, cat | Δ | 11.8 | 4.5 | 0.26 |
| PA894-6 | S151L ?, cat | Δ | 11.2 | 4.7 | 0.27 |
| PA894-7 | S151L ?, cat | Δ | 13.1 | 4.7 | 0.26 |
| PA894-8 | S151L ?, cat | Δ | 13.2 | 4.8 | 0.32 |

In medium containing β-alanine, PA894 (S151L), but not PA893 (Y155M) gave, on average, slightly higher pantothenate levels than PA892 (the isogenic strain with wild type coaA). PA880 gave significantly higher pantothenate (5.5 and 5.1 g/l) than its isogenic parent, PA824 (4.4 and 4.1 g/l), and slightly higher pantothenate levels than PA894 (average about 4.7 g/l). It is possible that the ΔyqjT::cat insertion present in PA892, PA893, and PA894 (but not PA880) has an effect that counteracts any gain that might result from the mutated coaA alleles.

Despite the narrow range of pantothenate titers from the new strains, a highly significant pattern was observed for production of HMBPA. In all strains where coaX was deleted, the HMBPA titer was two- to three-fold lower than for PA824. This is consistent with the principle that HMBPA production results in part from a limitation in PanB activity. Consequently, ΔcoaX leads to increased PanB activity.

Example VI

Increasing Pantothenate Synthesis by Combined Increase in PanB and Reduction of Pantothenate Kinase in Production Strains PA668, which contains an extra PanB expression cassette that is designed to be amplified by chloramphenicol (see Example IV), produces more pantothenate and less HMBPA than its predecessor, PA824. Since deletion of coaX from PA824 also reduces HMBPA production and moderately improves pantothenate production PA880), a strain combining the two modifications was constructed and tested for pantothenate production. Plasmid pAN636 (FIG. 9) was digested with NotI, ligated into circles, and used to transform PA880 to chloramphenicol resistance to give strain PA911. Several isolates of PA911 were tested by PCR to determine whether the plasmid had integrated at vpr as intended, or at panB, where it can also integrate. Both types were found. One isolate of each type of PA911, PA911-5 and PA911-8, were amplified on tetracycline (panD cassette) and chloramphenicol panB cassette) and tested for pantothenate production in test tube cultures grown in SVY plus β-alanine (see Table 1). Both isolates produced more pantothenate, and slightly less HMBPA than their parent, PA880. Moreover, consistent with the PA668 isolates, PA911-8, which has the panB cassette integrated at panB, produced the highest level of pantothenate.

Example VII

Increasing Pantothenate Production by Increasing Serine Availability

It was hypothesized that the ratio of pantothenate to HMBPA production could also be controlled by regulating the availability of serine in the microorganism cultures. In particular, it was proposed that increasing the availability of serine could increase pantothenate production relative to HMBPA production, whereas decreasing the availability of serine would decrease the production of pantothenate relative to HMBPA production. This method is based on the understanding that the PanB substrate, methylenetetrahydrofolate, is derived from serine. Thus, regulating serine levels should effectively regulate PanB substrate levels. To test this hypothesis, PA824 was grown in test tube cultures of SVY glucose plus 5 g/L β-alanine and ±5 g/L serine for 48 hours and 43° C.

TABLE 5

Production of pantothenate and HMBPA by PA824 with and without the addition of serine

| serine added at 5 g/L | OD$_{600}$ | [pan] g/L | [HMBPA] g/L |
|---|---|---|---|
| − | 16.3 | 4.9 | 0.84 |
| − | 14.0 | 4.5 | 0.80 |
| + | 13.1 | 6.4 | 0.56 |
| + | 12.9 | 6.0 | 0.62 |

As demonstrated by the data presented in Table 5, addition of serine increases the level of production of pantothenate while conversely decreasing HMBPA production. As an alternative to feeding serine, another method of increasing serine and methylenetetrahydrofolate levels in order to regulate pantothenate production levels is to increase synthesis or the activity of 3-phosphoglycerate dehydrogenase or of serine hydroxymethyl transferase (the serA and glyA gene products, respectively), thereby increasing serine and methylenetetrahydrofolate biosynthesis in appropriately engineered microorganisms.

Example VIII

Pantothenate Production with Strains PA668-2A and PA668-24 in 10-Liter Fermentors with Soy Flour Based Medium Stains PA668-2A and PA668-24 were each grown twice in 10 liter fermentors. The medium was PFM-155 and the composition is as follows.

| | MATERIAL | g/L (final) |
|---|---|---|
| | BATCH | |
| 1 | Amberex 1003 | 5 |
| 2 | Cargill 200/20 (soy flour) | 40 |
| 3 | Na Glutamate | 5 |

-continued

| | MATERIAL | g/L (final) |
|---|---|---|
| 4 | (NH$_4$)$_2$SO$_4$ | 8 |
| 5 | MgSO$_4$.7H$_2$O | 1 |
| 6 | MAZU DF204C | 1 |
| 7 | H$_2$O | qs to 4 L |
| Added After Sterilization and Cool Down | | |
| 1 | KH$_2$PO$_4$ | 10 |
| 2 | K$_2$HPO$_4$.3H$_2$O | 20 |
| 3 | H$_2$O | qs to 400 ml |
| 1 | 80% Glucose | 20 |
| 2 | CaCl$_2$.2H$_2$O | 0.1 |
| 1 | Sodium Citrate | 1 |
| 2 | FeSO$_4$.7H$_2$O | 0.01 |
| 3 | SM-1000X | 1 X |
| FEED | | |
| 1 | 80% Glucose | 800 |
| 2 | CaCl$_2$.2H$_2$O | 0.8 |
| 3 | H$_2$O | qs to 3500 ml |
| Added After Sterilization and Cool Down | | |
| 1 | Sodium Citrate | 2.0 |
| 2 | FeSO$_4$.7H$_2$O | 0.02 |
| 3 | SM-1000X | 2 X |
| 4 | Glutamate Na | 5.0 |
| 5 | H$_2$O | qs to 500 ml |

The pantothenate production by PA668-2A was 45 g/L and 51 g/L at 36 hours, similar to routine PA824 fermentations in the same medium. After 36 hours, when pantothenate production routinely begins to slow with PA824, both PA668-2A fermentations continued production to yield 63 g/l pantothenate at 48 hours. Most significantly, the production of HMPBA at 48 hours was reduced to 3–5 g/L, and was less than 5% of the pantothenate during most of the earlier fermentation. Clear benefits to pantothenate synthesis are evident from the increased levels of PanB in strain PA668. Strain PA668-24 produced pantothenate at an even faster rate with the two fermentations averaging 58 g/L after 36 hours.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A process for the production of a 3-(2-hydroxy-3-methyl-butyrylamino)-propionic acid- (HMBPA)-free pantothenate composition, comprising:
   transforming a *Bacillus subtilis* cell with a recombinant vector as set forth in SEQ ID NO:24;
   selecting chlormaphenicol resistant recombinant cells having reduced PanE2 activity, thereby producing a recombinant microorganism; and
   culturing said recombinant microorganism under suitable conditions such that an HMBPA-free pantothenate composition is produced, wherein said HMBPA-free pantothenate composition has an HMBPA to pantothenate ratio of less than 10 to 100.

2. The process of claim 1, wherein said microorganism is further modified such that at least one biosynthetic enzyme selected from the group consisting of ketopantoate hydroxymethyltransferase, ketopantoate reductase, pantothenate synthetase and aspartate-α-decarboxylase, is overexpressed.

3. The process of claim 1, wherein said microorganism is cultured under conditions of reduced steady state glucose.

4. The process of 1, wherein said microorganism is cultured under conditions of increased steady state dissolved oxygen.

5. The process of claim 1, wherein said microorganism further overexpresses the panD gene such that pantothenate production is independent of β-alanine feed.

6. The process of claim 1, wherein said HMBPA-free pantothenate composition has an HMBPA to pantothenate ratio of less than 5 to 100.

7. The process of claim 1, wherein said HMBPA-free pantothenate composition has an HMBPA to pantothenate ratio of less than 1 to 100.

8. The process of claim 1, wherein said HMBPA-free pantothenate composition has an HMBPA to pantothenate ratio of less than 0.5 to 100.

9. The process of claim 1, wherein said culturing is for about 12–24 hours.

10. The process of claim 1, wherein said culturing is for about 24–36 hours.

11. The process of claim 1, wherein said culturing is for about 26–48 hours.

12. The process of claim 1, wherein said culturing is for about 48–72 hours.

13. The process of claim 1, further comprising isolating the HMBPA-free pantothenate composition from the culture medium.

* * * * *